US010364422B2

(12) United States Patent
Scott et al.

(10) Patent No.: US 10,364,422 B2
(45) **Date of Patent: *Jul. 30, 2019**

(54) CELLULASE ENZYMES HAVING A MODIFIED LINKER AND REDUCED LIGNIN BINDING

(71) Applicant: Iogen Energy Corporation, Ottawa (CA)

(72) Inventors: Brian R. Scott, Richmond (CA); Patrick St-Pierre, Gatineau (CA); James Lavigne, Ottawa (CA); Nabil Masri, Gatineau (CA); Theresa C. White, Ottawa (CA); John J. Tomashek, Ottawa (CA)

(73) Assignee: IOGEN ENERGY CORPORATION, Ottawa (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/005,309

(22) Filed: Jan. 25, 2016

(65) Prior Publication Data

US 2016/0201043 A1 Jul. 14, 2016

Related U.S. Application Data

(63) Continuation of application No. 12/713,516, filed on Feb. 26, 2010, now Pat. No. 9,279,112.

(60) Provisional application No. 61/156,337, filed on Feb. 27, 2009.

(51) Int. Cl.
*C12N 9/42* (2006.01)
*C12P 19/14* (2006.01)
*C12P 19/02* (2006.01)

(52) U.S. Cl.
CPC ............ *C12N 9/2437* (2013.01); *C12P 19/02* (2013.01); *C12P 19/14* (2013.01)

(58) Field of Classification Search
None
See application file for complete search history.

(56) References Cited

U.S. PATENT DOCUMENTS 4,237,226 A 12/1980 Grethlein
4,356,196 A 10/1982 Hultquist
4,409,032 A 10/1983 Paszner et al.
4,461,648 A 7/1984 Foody
4,556,430 A 12/1985 Converse et al.
4,600,590 A 7/1986 Dale
5,037,663 A 8/1991 Dale
5,171,592 A 12/1992 Holtzapple et al.
5,536,325 A 7/1996 Brink
5,916,780 A 6/1999 Foody et al.
5,939,544 A 8/1999 Karstens et al.
6,043,392 A 3/2000 Holtzapple et al.
6,090,595 A 7/2000 Foody et al.
6,106,888 A 8/2000 Dale et al.
6,114,296 A 9/2000 Schülein et al.
6,176,176 B1 1/2001 Dale et al.
7,348,168 B2 3/2008 Wu et al.
7,354,743 B2 4/2008 Vlasenko et al.
7,375,197 B2 5/2008 Adney et al.
9,206,406 B2 * 12/2015 Tomashek ................. C12P 7/06
9,279,112 B2 * 3/2016 Scott ....................... C12P 19/14
9,885,028 B2 * 2/2018 Tomashek ................. C12P 7/06
2004/0185542 A1 9/2004 Yang et al.
2006/0088922 A1 4/2006 Yang et al.
2006/0205042 A1 9/2006 Aehle et al.
2007/0173431 A1 7/2007 Day et al.
2008/0076152 A1 * 3/2008 St-Pierre ........ C12Y 302/01091 435/69.1
2008/0167214 A1 7/2008 Teter et al.
2009/0162916 A1 6/2009 Adney et al.
2009/0186381 A1 7/2009 Lavigne et al.
2010/0041104 A1 2/2010 Cascao-Pereira et al.

FOREIGN PATENT DOCUMENTS

WO 94/07998 A1 4/1994
WO 99/01544 A1 1/1999
WO 2005/028636 A1 3/2005
WO 2005024037 A2 3/2005
WO 2005/093072 A1 10/2005
WO 2006/074005 A2 7/2006
(Continued)

OTHER PUBLICATIONS

Schultz et al., Proteins Structure and Function, pp. 521-528, Plenum Press, New York, 1987.*
Clarke, A.J., "Biodegradation of Cellulose, Enzymology and Biotechnology", Technomic Publishing Co., Lancaster, Pennsylvania, 1997, p. 55 (Year: 1997).*
Gilkes et al., "Domains in Microbial β-1,4-Glycanases: Sequence Conservation, Function and Enzyme Families", Microbiolological Reviews, vol. 55, No. 2 (1991) 303-15.
Berlin et al., "Weak Lignin-Binding Enzymes", Applied Biochemistry and Biotechnology, vol. 121-124 (2005) 163-70.
Dashtban et al., "Fungal Bioconversion of Lignocellulosic Residues; Opportunities and Perspectives", Int. J. Biol. Sci., vol. 5, No. 6 (2009) 578-95.
(Continued)

*Primary Examiner* — David Steadman
(74) *Attorney, Agent, or Firm* — Venable LLP

(57) ABSTRACT

Provided are modified cellulase enzymes exhibiting increase cellulose-hydrolyzing activity in the presence of lignin and/or reduced binding to lignin comprising modified linker peptides comprising one or more amino acid substitutions, insertions, or deletions that result in (a) a decrease in the calculated isoelectric point of the linker peptide and/or (b) an increase in the ratio of threonine:serine in the linker peptide relative to a parental linker peptide from which said modified linker peptide is derived. Also provided are genetic constructs comprising nucleic acid sequences encoding for modified cellulase enzymes, methods for the production of the modified cellulase enzymes from host strains and a process for hydrolysing cellulose with the modified cellulases in the presence of lignin.

11 Claims, 16 Drawing Sheets

Specification includes a Sequence Listing.

(56) References Cited

FOREIGN PATENT DOCUMENTS

| | | | |
|---|---|---|---|
| WO | 2006/128304 | A1 | 12/2006 |
| WO | 2008025164 | A1 | 3/2008 |
| WO | 2008153925 | A2 | 12/2008 |
| WO | 2009149202 | A2 | 12/2009 |
| WO | 2010/012102 | A1 | 2/2010 |

OTHER PUBLICATIONS

Bae et al., "Prediction of Protein Interdomain Linker Regions by a Nonstationary Hidden Markov Model", Journal of the American Statistical Association, vol. 103, No. 483 (2008) 1085-99.
Yang, et al., "BSA Treatment to Enhance Enzymatic Hydrolysis of Cellulose in Lignin Containing Substrates", Biotechnology and Bioengineering, vol. 94, No. 4 (2006) 611-17.
Bhikhabhai et al., "Isolation of Cellulolytic Enzymes from Trichoderma Reesei QM 9414", Journal of Applied Biochemistry, vol. 6 (1984) 336-45.
Boisset et al., "Dynamic light scattering study of a two-domain structure of Humicola insolens endoglucanase V", FEBS Letters, vol. 376 (1995) 49-52.
Chernoglazov et al., "Adsorption of high-purity endo-1,4- β-glucanases from Trichoderma reesei on components of lignocellulosic materials: cellulose, lignin, and xylan", Enzyme and Microbial Technology, vol. 10 (1988) 503-7.
Davies, et al., "Structures and mechanisms of glycosyl hydrolases", Structure, vol. 3, No. 9 (1995) 853-59.
Escoffier et al., "Saccharification of Steam-Exploded Poplar Wood", Biotechnology and Bioengineering, vol. 38, (1991) 1308-17.
Fägerstam et al., "The primary structure of a 1,4-β-glucan cellobiohydrolase from the fungus *Trichoderma reesei* QM 9414", FEBS Letters, vol. 167, No. 2 (1984) 309-15.
Foreman et al., "Transcriptional Regulation of Biomass-degrading Enzymes in the Filamentous Fungus *Trichoderma reesei*", Journal of Biological Chemistry, vol. 278, No. 34 (2003) 31988-97.
Goto, "Protein O-Glycosylation in Fungi: Diverse Structures and Multiple Functions", Biosci. Biotechnol. Biochem., vol. 71, No. 6 (2007) 1415-1427.
Kaya et al., "Influence of lignin and its degradation products on enzymatic hydrolysis of xylan", Journal of Biotechnology, vol. 80 (2000) 241-47.
Kong et al. "Effects of Cell-Wall Acetate, Xylan Backbone, and Lignin on Enzymatic Hydrolysis of Aspen Wood", Applied Biochemistry and Biotechnology, vol. 34/35 (1992) 23-5.
Kraulis et al., "Determination of the Three-Dimensional Solution Structure of the C-Terminal Domain of Cellobiohydrolase I from Trichoderma reesei. A Study Using Nuclear Magnetic Resonance and Hybrid Distance Geometry-Dynamical Simulated Annealing", Biochemistry, vol. 28, No. 18 (1989) 7241-57.
Mattinen et al., "Interaction between cellohexaose and cellulose binding domains from Trichoderma reesei cellulases", FEBS Letters, vol. 407 (1997) 291-96.
Meunier-Goddik, et al., "Enzyme-Catalyzed Saccharification of Model Celluloses in the Presence of Lignacious Residues", J. Agric. Chem., vol. 47, No. 1 (1999) 346-51.
Mooney et al., "The effect of Initial Pore Volume and Lignin Content on the Enzymatic Hydrolysis of Softwoods", Bioresource Technology, vol. 64 (1998) 113-19.
Von Ossowski et al., "Protein Disorder: Conformational Distribution of a Flexible Linker in a Chimeric Double Cellulase", Biophysical Journal, vol. 88 (2005) 2823-32.
Palonen et al., "Adsorption of Trichoderma reesei CBH I and EG II and their catalytic domains on steam pretreated softwood and isolated lignin", Journal of Biotechnology, vol. 107 (2004) 65-72.
Saloheimo et al., "Swollenin, a Trichoderma reesei protein with sequence similarity to the plant expansins, exhibits disruption activity on cellulosic materials", Eur. J. of Biochem., vol. 269 (2002) 4202-211.
Receveur et al., "Dimension, Shape, and Conformational Flexibility of a Two Domain Fungal Cellulase in Solution Probed by Small Angle X-ray Scattering", Journal of Biological Chemistry, vol. 277, No. 43 (2002) 40887-892.
Reinikainen et al., "Investigation of the Function of Mutated Cellulose-Binding Domains of Trichoderma reesei Cellobiohydrolase I", Proteins, vol. 14, No. 4 (1992) 475-82.
Shen et al., "Deletion of the Linker Connecting the Catalytic and Cellulose-binding Domains of Endoglucanase A (CenA) of Cellulomonas fimi Alters Its Conformation and Catalytic Activity", Journal of Biological Chemistry, vol. 266, No. 17 (1991) 11335-340.
Srisodsuk et al., "Role of the Interdomain Linker Peptide of Trichoderma reesei Cellobiohydrolase I in Its Interaction with Crystalline Cellulose", The Journal of Biological Chemistry, vol. 268, No. 28 (1993) 20756-761.
Suyama, et al., "DomCut: prediction of inter-domain linker regions in amino acid sequences", Bioinformatics, vol. 19, No. 5 (2003) 673-74.
Piyachomkwan et al., "Aryl Thioglycoside-Based Affinity Purification of Exo-Acting Cellulases", Analytical Biochemistry, vol. 255 (1998) 223-35.
Piyachomkwan et al., "p-Aminophenyl 1-thio-β-D cellobioside: Synthesis and application in affinity chromatography of exo-type cellulases", Carbohydrate Research, vol. 303 (1997) 255-59.
Tu et al., "Evaluating the Distribution of Cellulases and the Recycling of Free Cellulases during the Hydrolysis of Lignocellulosic Substrates", Biotech. Prog., vol. 23, No. 2 (2007) 398-406.
EMBL Accession No. P07987, Jan. 2008, 3 pages.
Mingardon et al., "Incorporation of Fungal Cellulases in Bacterial Minicellulosomes Yields Viable, Synergistically Acting Cellulolytic Complexes", Applied and Environmental Microbiology, vol. 73, No. 12 (2007) 3822-3832.
Airaksinen et al., "Modified base compositions at degenerate positions of a mutagenic oligonucleotide enhance randomness in site-saturation mutagenesis", Nucleic Acids Research, vol. 26, No. 2 (1998) 576-581.
Holtzapple, M.T., et al., "The ammonia freeze explosion (AFEX) process: A practical lignocellulosic pretreatment.," Applied Biochemistry and Biotechnology, 28, pp. 29:59-74 (1991).
Montenecourt , B.S. and Eveleigh, D.E., "Selective screening methods for the isolation of high yielding cellulase mutants of Trichoderma reesei," Adv. Chem. Ser., 181, pp. 289-301 (1979).
Ossowski, I. et al., "Protein Disorder: Conformational distribution of a flexible linker in a chimeric double cellulose," Biophysical Journal, 88, pp. 2823-2832 (2005).
Tormo, J., et al., "Crystal structure of a bacterial family-III cellulose-binding domain: a general mechanism for attachment to cellulose," EMBO Journal, 15(21), pp. 5739-5751 (1996).

* cited by examiner

Assay 1

Assay 2

Linker (amino acids 39-82)

Wt 1 QACSSVWGQCGGQNWSGPTCCASGSTCVYSNDYYSQCLPGAASSSSSTRAASTTSRVSPTTSRSSSATPPPGSTTTRVPPVGSGTATYSGNPFVGVTPW 99

Aggregate QACSSVWGQCGGQNWSGPTCCASGSTCVYSNDYYFQCLPDAASSNSSTRAASTTSRVSPTTSLSSSATPPTDSTTARVPPDGSGTATYSGNPFVGVTPW R→E QACSSVWGQCGGQNWSGPTCCASGSTCVYSNDYYSQCLPGAASSSSSTEAASTTSEVSPTTSESSSATPPPGSTTTEVPPVGSGTATYSGNPFVGVTPW R→E/S→T QACSSVWGQCGGQNWSGPTCCASGSTCVYSNDYYSQCLPGAATTTTTTEAATTTTEVTPTTTETTTATPPPGTTTTEVPPVGSGTATYSGNPFVGVTPW Δ1 QACSSVWGQCGGQNWSGPTCCASGSTCVYSNDYYSQCLPGAASSSSSTRAASTTSRVSPTTS--------------------SGTATYSGNPFVGVTPW Δ2 QACSSVWGQCGGQNWSGPTCCASGSTCVYSNDYYSQCL--------------------PTTSRSSSATPPPGSTTTRVPPVGSGTATYSGNPFVGVTPW

Fig. 7

SDS-PAGE

IEF-PAGE

SEQUENCE LISTING

```
<160> NUMBER OF SEQ ID NOS: 83

<210> SEQ ID NO 1
<211> LENGTH: 447
<212> TYPE: PRT
<213> ORGANISM: Trichoderma reesei

<400> SEQUENCE: 1

Gln Ala Cys Ser Ser Val Trp Gly Gln Cys Gly Gly Gln Asn Trp Ser
```

-continued

```
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Ser His Cys Ala
                405                 410                 415

Leu Pro Asp Ala Leu Gln Pro Ala Pro Gln Ala Gly Ala Trp Phe Gln
            420                 425                 430
```

```
Ala Tyr Phe Val Gln Leu Leu Thr Asn Ala Asn Pro Ser Phe Leu
        435                 440                 445


<210> SEQ ID NO 2
<211> LENGTH: 397
<212> TYPE: PRT
<213> ORGANISM: Trichoderma reesei

<400> SEQUENCE: 2

Gln Gln Thr Val Trp Gly Gln Cys Gly Gly Ile Gly Trp Ser Gly Pro
1               5                   10                  15

Thr Asn Cys Ala Pro Gly Ser Ala Cys Ser Thr Leu Asn Pro Tyr Tyr
            20                  25                  30

Ala Gln Cys Ile Pro Gly Ala Thr Thr Ile Thr Thr Ser Thr Arg Pro
        35                  40                  45

Pro Ser Gly Pro Thr Thr Thr Thr Arg Ala Thr Ser Thr Ser Ser Ser
    50                  55                  60

Thr Pro Pro Thr Ser Ser Gly Val Arg Phe Ala Gly Val Asn Ile Ala
65                  70                  75                  80

Gly Phe Asp Phe Gly Cys Thr Thr Asp Gly Thr Cys Val Thr Ser Lys
                85                  90                  95

Val Tyr Pro Pro Leu Lys Asn Phe Thr Gly Ser Asn Asn Tyr Pro Asp
            100                 105                 110

Gly Ile Gly Gln Met Gln His Phe Val Asn Asp Asp Gly Met Thr Ile
        115                 120                 125

Phe Arg Leu Pro Val Gly Trp Gln Tyr Leu Val Asn Asn Asn Leu Gly
    130                 135                 140

Gly Asn Leu Asp Ser Thr Ser Ile Ser Lys Tyr Asp Gln Leu Val Gln
145                 150                 155                 160

Gly Cys Leu Ser Leu Gly Ala Tyr Cys Ile Val Asp Ile His Asn Tyr
                165                 170                 175

Ala Arg Trp Asn Gly Gly Ile Ile Gly Gln Gly Gly Pro Thr Asn Ala
            180                 185                 190

Gln Phe Thr Ser Leu Trp Ser Gln Leu Ala Ser Lys Tyr Ala Ser Gln
        195                 200                 205

Ser Arg Val Trp Phe Gly Ile Met Asn Glu Pro His Asp Val Asn Ile
    210                 215                 220

Asn Thr Trp Ala Ala Thr Val Gln Glu Val Val Thr Ala Ile Arg Asn
225                 230                 235                 240

Ala Gly Ala Thr Ser Gln Phe Ile Ser Leu Pro Gly Asn Asp Trp Gln
                245                 250                 255

Ser Ala Gly Ala Phe Ile Ser Asp Gly Ser Ala Ala Ala Leu Ser Gln
            260                 265                 270

Val Thr Asn Pro Asp Gly Ser Thr Thr Asn Leu Ile Phe Asp Val His
        275                 280                 285

Lys Tyr Leu Asp Ser Asp Asn Ser Gly Thr His Ala Glu Cys Thr Thr
    290                 295                 300

Asn Asn Ile Asp Gly Ala Phe Ser Pro Leu Ala Thr Trp Leu Arg Gln
305                 310                 315                 320

Asn Asn Arg Gln Ala Ile Leu Thr Glu Thr Gly Gly Gly Asn Val Gln
                325                 330                 335

Ser Cys Ile Gln Asp Met Cys Gln Gln Ile Gln Tyr Leu Asn Gln Asn
            340                 345                 350

Ser Asp Val Tyr Leu Gly Tyr Val Gly Trp Gly Ala Gly Ser Phe Asp
```

```
        355                 360                 365

Ser Thr Tyr Val Leu Thr Glu Thr Pro Thr Gly Ser Gly Asn Ser Trp
    370                 375                 380

Thr Asp Thr Ser Leu Val Ser Ser Cys Leu Ala Arg Lys
385                 390                 395


<210> SEQ ID NO 3
<211> LENGTH: 497
<212> TYPE: PRT
<213> ORGANISM: Trichoderma reesei

<400> SEQUENCE: 3

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335
```

```
Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
        355                 360                 365

Asp Tyr Tyr Ala Asn Met Leu Trp Leu Asp Ser Thr Tyr Pro Thr Asn
    370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
            420                 425                 430

Ser Gly Gly Asn Pro Pro Gly Gly Asn Pro Pro Gly Thr Thr Thr Thr
        435                 440                 445

Arg Arg Pro Ala Thr Thr Thr Gly Ser Ser Pro Gly Pro Thr Gln Ser
    450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495

Leu


<210> SEQ ID NO 4
<211> LENGTH: 437
<212> TYPE: PRT
<213> ORGANISM: Trichoderma reesei

<400> SEQUENCE: 4

Gln Gln Pro Gly Thr Ser Thr Pro Glu Val His Pro Lys Leu Thr Thr
1               5                   10                  15

Tyr Lys Cys Thr Lys Ser Gly Gly Cys Val Ala Gln Asp Thr Ser Val
            20                  25                  30

Val Leu Asp Trp Asn Tyr Arg Trp Met His Asp Ala Asn Tyr Asn Ser
        35                  40                  45

Cys Thr Val Asn Gly Gly Val Asn Thr Thr Leu Cys Pro Asp Glu Ala
    50                  55                  60

Thr Cys Gly Lys Asn Cys Phe Ile Glu Gly Val Asp Tyr Ala Ala Ser
65                  70                  75                  80

Gly Val Thr Thr Ser Gly Ser Ser Leu Thr Met Asn Gln Tyr Met Pro
                85                  90                  95

Ser Ser Ser Gly Gly Tyr Ser Ser Val Ser Pro Arg Leu Tyr Leu Leu
            100                 105                 110

Asp Ser Asp Gly Glu Tyr Val Met Leu Lys Leu Asn Gly Gln Glu Leu
        115                 120                 125

Ser Phe Asp Val Asp Leu Ser Ala Leu Pro Cys Gly Glu Asn Gly Ser
    130                 135                 140

Leu Tyr Leu Ser Gln Met Asp Glu Asn Gly Gly Ala Asn Gln Tyr Asn
145                 150                 155                 160

Thr Ala Gly Ala Asn Tyr Gly Ser Gly Tyr Cys Asp Ala Gln Cys Pro
                165                 170                 175

Val Gln Thr Trp Arg Asn Gly Thr Leu Asn Thr Ser His Gln Gly Phe
            180                 185                 190

Cys Cys Asn Glu Met Asp Ile Leu Glu Gly Asn Ser Arg Ala Asn Ala
        195                 200                 205
```

```
Leu Thr Pro His Ser Cys Thr Ala Thr Ala Cys Asp Ser Ala Gly Cys
    210                 215                 220

Gly Phe Asn Pro Tyr Gly Ser Gly Tyr Lys Ser Tyr Tyr Gly Pro Gly
225                 230                 235                 240

Asp Thr Val Asp Thr Ser Lys Thr Phe Thr Ile Ile Thr Gln Phe Asn
                245                 250                 255

Thr Asp Asn Gly Ser Pro Ser Gly Asn Leu Val Ser Ile Thr Arg Lys
            260                 265                 270

Tyr Gln Gln Asn Gly Val Asp Ile Pro Ser Ala Gln Pro Gly Gly Asp
        275                 280                 285

Thr Ile Ser Ser Cys Pro Ser Ala Ser Ala Tyr Gly Gly Leu Ala Thr
    290                 295                 300

Met Gly Lys Ala Leu Ser Ser Gly Met Val Leu Val Phe Ser Ile Trp
305                 310                 315                 320

Asn Asp Asn Ser Gln Tyr Met Asn Trp Leu Asp Ser Gly Asn Ala Gly
                325                 330                 335

Pro Cys Ser Ser Thr Glu Gly Asn Pro Ser Asn Ile Leu Ala Asn Asn
            340                 345                 350

Pro Asn Thr His Val Val Phe Ser Asn Ile Arg Trp Gly Asp Ile Gly
        355                 360                 365

Ser Thr Thr Asn Ser Thr Ala Pro Pro Pro Pro Pro Ala Ser Ser Thr
    370                 375                 380

Thr Phe Ser Thr Thr Arg Arg Ser Ser Thr Thr Ser Ser Ser Pro Ser
385                 390                 395                 400

Cys Thr Gln Thr His Trp Gly Gln Cys Gly Gly Ile Gly Tyr Ser Gly
                405                 410                 415

Cys Lys Thr Cys Thr Ser Gly Thr Thr Cys Gln Tyr Ser Asn Asp Tyr
            420                 425                 430

Tyr Ser Gln Cys Leu
        435


<210> SEQ ID NO 5
<211> LENGTH: 225
<212> TYPE: PRT
<213> ORGANISM: Trichoderma reesei

<400> SEQUENCE: 5

Tyr Lys Ala Thr Thr Thr Arg Tyr Tyr Asp Gly Gln Glu Gly Ala Cys
1               5                   10                  15

Gly Cys Gly Ser Ser Ser Gly Ala Phe Pro Trp Gln Leu Gly Ile Gly
            20                  25                  30

Asn Gly Val Tyr Thr Ala Ala Gly Ser Gln Ala Leu Phe Asp Thr Ala
        35                  40                  45

Gly Ala Ser Trp Cys Gly Ala Gly Cys Gly Lys Cys Tyr Gln Leu Thr
    50                  55                  60

Ser Thr Gly Gln Ala Pro Cys Ser Ser Cys Gly Thr Gly Gly Ala Ala
65                  70                  75                  80

Gly Gln Ser Ile Ile Val Met Val Thr Asn Leu Cys Pro Asn Asn Gly
                85                  90                  95

Asn Ala Gln Trp Cys Pro Val Val Gly Gly Thr Asn Gln Tyr Gly Tyr
            100                 105                 110

Ser Tyr His Phe Asp Ile Met Ala Gln Asn Glu Ile Phe Gly Asp Asn
        115                 120                 125

Val Val Val Asp Phe Glu Pro Ile Ala Cys Pro Gly Gln Ala Ala Ser
    130                 135                 140
```

```
Asp Trp Gly Thr Cys Leu Cys Val Gly Gln Gln Glu Thr Asp Pro Thr
145                 150                 155                 160

Pro Val Leu Gly Asn Asp Thr Gly Ser Thr Pro Pro Gly Ser Ser Pro
                165                 170                 175

Pro Ala Thr Ser Ser Ser Pro Pro Ser Gly Gly Gly Gln Gln Thr Leu
            180                 185                 190

Tyr Gly Gln Cys Gly Gly Ala Gly Trp Thr Gly Pro Thr Thr Cys Gln
        195                 200                 205

Ala Pro Gly Thr Cys Lys Val Gln Asn Gln Trp Tyr Ser Gln Cys Leu
    210                 215                 220

Pro
225


<210> SEQ ID NO 6
<211> LENGTH: 323
<212> TYPE: PRT
<213> ORGANISM: Trichoderma reesei

<400> SEQUENCE: 6

His Gly His Ile Asn Asp Ile Val Ile Asn Gly Val Trp Tyr Gln Ala
1               5                   10                  15

Tyr Asp Pro Thr Thr Phe Pro Tyr Glu Ser Asn Pro Pro Ile Val Val
            20                  25                  30

Gly Trp Thr Ala Ala Asp Leu Asp Asn Gly Phe Val Ser Pro Asp Ala
        35                  40                  45

Tyr Gln Asn Pro Asp Ile Ile Cys His Lys Asn Ala Thr Asn Ala Lys
    50                  55                  60

Gly His Ala Ser Val Lys Ala Gly Asp Thr Ile Leu Phe Gln Trp Val
65                  70                  75                  80

Pro Val Pro Trp Pro His Pro Gly Pro Ile Val Asp Tyr Leu Ala Asn
                85                  90                  95

Cys Asn Gly Asp Cys Glu Thr Val Asp Lys Thr Thr Leu Glu Phe Phe
            100                 105                 110

Lys Ile Asp Gly Val Gly Leu Leu Ser Gly Gly Asp Pro Gly Thr Trp
        115                 120                 125

Ala Ser Asp Val Leu Ile Ser Asn Asn Asn Thr Trp Val Val Lys Ile
    130                 135                 140

Pro Asp Asn Leu Ala Pro Gly Asn Tyr Val Leu Arg His Glu Ile Ile
145                 150                 155                 160

Ala Leu His Ser Ala Gly Gln Ala Asn Gly Ala Gln Asn Tyr Pro Gln
                165                 170                 175

Cys Phe Asn Ile Ala Val Ser Gly Ser Gly Ser Leu Gln Pro Ser Gly
            180                 185                 190

Val Leu Gly Thr Asp Leu Tyr His Ala Thr Asp Pro Gly Val Leu Ile
        195                 200                 205

Asn Ile Tyr Thr Ser Pro Leu Asn Tyr Ile Ile Pro Gly Pro Thr Val
    210                 215                 220

Val Ser Gly Leu Pro Thr Ser Val Ala Gln Gly Ser Ser Ala Ala Thr
225                 230                 235                 240

Ala Thr Ala Ser Ala Thr Val Pro Gly Gly Gly Ser Gly Pro Thr Ser
                245                 250                 255

Arg Thr Thr Thr Thr Ala Arg Thr Thr Gln Ala Ser Ser Arg Pro Ser
            260                 265                 270

Ser Thr Pro Pro Ala Thr Thr Ser Ala Pro Ala Gly Gly Pro Thr Gln
```

```
        275                 280                 285

Thr Leu Tyr Gly Gln Cys Gly Gly Ser Gly Tyr Ser Gly Pro Thr Arg
    290                 295                 300

Cys Ala Pro Pro Ala Thr Cys Ser Thr Leu Asn Pro Tyr Tyr Ala Gln
305                 310                 315                 320

Cys Leu Asn


<210> SEQ ID NO 7
<211> LENGTH: 297
<212> TYPE: PRT
<213> ORGANISM: Trichoderma reesei

<400> SEQUENCE: 7

Gln Ile Ser Asp Asp Phe Glu Ser Gly Trp Asp Gln Thr Lys Trp Pro
1               5                   10                  15

Ile Ser Ala Pro Asp Cys Asn Gln Gly Gly Thr Val Ser Leu Asp Thr
            20                  25                  30

Thr Val Ala His Ser Gly Ser Asn Ser Met Lys Val Val Gly Gly Pro
        35                  40                  45

Asn Gly Tyr Cys Gly His Ile Phe Phe Gly Thr Thr Gln Val Pro Thr
    50                  55                  60

Gly Asp Val Tyr Val Arg Ala Trp Ile Arg Leu Gln Thr Ala Leu Gly
65                  70                  75                  80

Ser Asn His Val Thr Phe Ile Ile Met Pro Asp Thr Ala Gln Gly Gly
                85                  90                  95

Lys His Leu Arg Ile Gly Gly Gln Ser Gln Val Leu Asp Tyr Asn Arg
            100                 105                 110

Glu Ser Asp Asp Ala Thr Leu Pro Asp Leu Ser Pro Asn Gly Ile Ala
        115                 120                 125

Ser Thr Val Thr Leu Pro Thr Gly Ala Phe Gln Cys Phe Glu Tyr His
    130                 135                 140

Leu Gly Thr Asp Gly Thr Ile Glu Thr Trp Leu Asn Gly Ser Leu Ile
145                 150                 155                 160

Pro Gly Met Thr Val Gly Pro Gly Val Asp Asn Pro Asn Asp Ala Gly
                165                 170                 175

Trp Thr Arg Ala Ser Tyr Ile Pro Glu Ile Thr Gly Val Asn Phe Gly
            180                 185                 190

Trp Glu Ala Tyr Ser Gly Asp Val Asn Thr Val Trp Phe Asp Asp Ile
        195                 200                 205

Ser Ile Ala Ser Thr Arg Val Gly Cys Gly Pro Gly Ser Pro Gly Gly
    210                 215                 220

Pro Gly Ser Ser Thr Thr Gly Arg Ser Ser Thr Ser Gly Pro Thr Ser
225                 230                 235                 240

Thr Ser Arg Pro Ser Thr Thr Ile Pro Pro Pro Thr Ser Arg Thr Thr
                245                 250                 255

Thr Ala Thr Gly Pro Thr Gln Thr His Tyr Gly Gln Cys Gly Gly Ile
            260                 265                 270

Gly Tyr Ser Gly Pro Thr Val Cys Ala Ser Gly Thr Thr Cys Gln Val
        275                 280                 285

Leu Asn Pro Tyr Tyr Ser Gln Cys Leu
    290                 295


<210> SEQ ID NO 8
<211> LENGTH: 475
<212> TYPE: PRT
```

<213> ORGANISM: Trichoderma reesei

<400> SEQUENCE: 8

```
Gln Gln Asn Cys Ala Ala Leu Phe Gly Gln Cys Gly Gly Ile Gly Trp
1               5                   10                  15

Ser Gly Thr Thr Cys Cys Val Ala Gly Ala Gln Cys Ser Phe Val Asn
            20                  25                  30

Asp Trp Tyr Ser Gln Cys Leu Ala Ser Thr Gly Gly Asn Pro Pro Asn
        35                  40                  45

Gly Thr Thr Ser Ser Ser Leu Val Ser Arg Thr Ser Ser Ala Ser Ser
    50                  55                  60

Ser Val Gly Ser Ser Ser Pro Gly Gly Asn Ser Pro Thr Gly Ser Ala
65                  70                  75                  80

Ser Thr Tyr Thr Thr Thr Asp Thr Ala Thr Val Ala Pro His Ser Gln
                85                  90                  95

Ser Pro Tyr Pro Ser Ile Ala Ala Ser Ser Cys Gly Ser Trp Thr Leu
            100                 105                 110

Val Asp Asn Val Cys Cys Pro Ser Tyr Cys Ala Asn Asp Asp Thr Ser
        115                 120                 125

Glu Ser Cys Ser Gly Cys Gly Thr Cys Thr Thr Pro Pro Ser Ala Asp
    130                 135                 140

Cys Lys Ser Gly Thr Met Tyr Pro Glu Val His His Val Ser Ser Asn
145                 150                 155                 160

Glu Ser Trp His Tyr Ser Arg Ser Thr His Phe Gly Leu Thr Ser Gly
                165                 170                 175

Gly Ala Cys Gly Phe Gly Leu Tyr Gly Leu Cys Thr Lys Gly Ser Val
            180                 185                 190

Thr Ala Ser Trp Thr Asp Pro Met Leu Gly Ala Thr Cys Asp Ala Phe
        195                 200                 205

Cys Thr Ala Tyr Pro Leu Leu Cys Lys Asp Pro Thr Gly Thr Thr Leu
    210                 215                 220

Arg Gly Asn Phe Ala Ala Pro Asn Gly Asp Tyr Tyr Thr Gln Phe Trp
225                 230                 235                 240

Ser Ser Leu Pro Gly Ala Leu Asp Asn Tyr Leu Ser Cys Gly Glu Cys
                245                 250                 255

Ile Glu Leu Ile Gln Thr Lys Pro Asp Gly Thr Asp Tyr Ala Val Gly
            260                 265                 270

Glu Ala Gly Tyr Thr Asp Pro Ile Thr Leu Glu Ile Val Asp Ser Cys
        275                 280                 285

Pro Cys Ser Ala Asn Ser Lys Trp Cys Cys Gly Pro Gly Ala Asp His
    290                 295                 300

Cys Gly Glu Ile Asp Phe Lys Tyr Gly Cys Pro Leu Pro Ala Asp Ser
305                 310                 315                 320

Ile His Leu Asp Leu Ser Asp Ile Ala Met Gly Arg Leu Gln Gly Asn
                325                 330                 335

Gly Ser Leu Thr Asn Gly Val Ile Pro Thr Arg Tyr Arg Arg Val Gln
            340                 345                 350

Cys Pro Lys Val Gly Asn Ala Tyr Ile Trp Leu Arg Asn Gly Gly Gly
        355                 360                 365

Pro Tyr Tyr Phe Ala Leu Thr Ala Val Asn Thr Asn Gly Pro Gly Ser
    370                 375                 380

Val Thr Lys Ile Glu Ile Lys Gly Ala Asp Thr Asp Asn Trp Val Ala
385                 390                 395                 400
```

```
Leu Val His Asp Pro Asn Tyr Thr Ser Ser Arg Pro Gln Glu Arg Tyr
                405                 410                 415

Gly Ser Trp Val Ile Pro Gln Gly Ser Gly Pro Phe Asn Leu Pro Val
            420                 425                 430

Gly Ile Arg Leu Thr Ser Pro Thr Gly Glu Gln Ile Val Asn Glu Gln
        435                 440                 445

Ala Ile Lys Thr Phe Thr Pro Pro Ala Thr Gly Asp Pro Asn Phe Tyr
    450                 455                 460

Tyr Ile Asp Ile Gly Val Gln Phe Ser Gln Asn
465                 470                 475


<210> SEQ ID NO 9
<211> LENGTH: 447
<212> TYPE: PRT
<213> ORGANISM: Trichoderma reesei

<400> SEQUENCE: 9

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300
```

```
Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445


<210> SEQ ID NO 10
<211> LENGTH: 447
<212> TYPE: PRT
<213> ORGANISM: Trichoderma reesei

<400> SEQUENCE: 10

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Phe Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
```

```
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445


<210> SEQ ID NO 11
<211> LENGTH: 447
<212> TYPE: PRT
<213> ORGANISM: Trichoderma reesei

<400> SEQUENCE: 11

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Asp Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160
```

```
Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445


<210> SEQ ID NO 12
<211> LENGTH: 447
<212> TYPE: PRT
<213> ORGANISM: Trichoderma reesei

<400> SEQUENCE: 12

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Asn Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95
```

```
Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445


<210> SEQ ID NO 13
<211> LENGTH: 447
<212> TYPE: PRT
<213> ORGANISM: Trichoderma reesei

<400> SEQUENCE: 13

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
```

```
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Leu Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445
```

<210> SEQ ID NO 14
<211> LENGTH: 447
<212> TYPE: PRT
<213> ORGANISM: Trichoderma reesei

<400> SEQUENCE: 14

```
Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Thr Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
```

```
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445


<210> SEQ ID NO 15
<211> LENGTH: 447
<212> TYPE: PRT
<213> ORGANISM: Trichoderma reesei

<400> SEQUENCE: 15

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Ala Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300
```

-continued

Asn Tyr Asn Gly Trp Asn Ile Thr Ser Pro Pro Ser Tyr Thr Gln Gly
305 310 315 320

Asn Ala Val Tyr Asn Glu Lys Leu Tyr Ile His Ala Ile Gly Pro Leu
325 330 335

Leu Ala Asn His Gly Trp Ser Asn Ala Phe Phe Ile Thr Asp Gln Gly
340 345 350

Arg Ser Gly Lys Gln Pro Thr Gly Gln Gln Gln Trp Gly Asp Trp Cys
355 360 365

Asn Val Ile Gly Thr Gly Phe Gly Ile Arg Pro Ser Ala Asn Thr Gly
370 375 380

Asp Ser Leu Leu Asp Ser Phe Val Trp Val Lys Pro Gly Gly Glu Cys
385 390 395 400

Asp Gly Thr Ser Asp Ser Ser Ala Pro Arg Phe Asp Pro His Cys Ala
405 410 415

Leu Pro Asp Ala Leu Gln Pro Ala Pro Gln Ala Gly Ala Trp Phe Gln
420 425 430

Ala Tyr Phe Val Gln Leu Leu Thr Asn Ala Asn Pro Ser Phe Leu
435 440 445

<210> SEQ ID NO 16
<211> LENGTH: 447
<212> TYPE: PRT
<213> ORGANISM: Trichoderma reesei

<400> SEQUENCE: 16

Gln Ala Cys Ser Ser Val Trp Gly Gln Cys Gly Gly Gln Asn Trp Ser
1 5 10 15

Gly Pro Thr Cys Cys Ala Ser Gly Ser Thr Cys Val Tyr Ser Asn Asp
20 25 30

Tyr Tyr Ser Gln Cys Leu Pro Gly Ala Ala Ser Ser Ser Ser Ser Thr
35 40 45

Arg Ala Ala Ser Thr Thr Ser Arg Val Ser Pro Thr Thr Ser Arg Ser
50 55 60

Ser Ser Ala Thr Pro Pro Pro Asp Ser Thr Thr Thr Arg Val Pro Pro
65 70 75 80

Val Gly Ser Gly Thr Ala Thr Tyr Ser Gly Asn Pro Phe Val Gly Val
85 90 95

Thr Pro Trp Ala Asn Ala Tyr Tyr Ala Ser Glu Val Ser Ser Leu Ala
100 105 110

Ile Pro Ser Leu Thr Gly Ala Met Ala Thr Ala Ala Ala Ala Val Ala
115 120 125

Lys Val Pro Ser Phe Met Trp Leu Asp Thr Leu Asp Lys Thr Pro Leu
130 135 140

Met Glu Gln Thr Leu Ala Asp Ile Arg Thr Ala Asn Lys Asn Gly Gly
145 150 155 160

Asn Tyr Ala Gly Gln Phe Val Val Tyr Asp Leu Pro Asp Arg Asp Cys
165 170 175

Ala Ala Leu Ala Ser Asn Gly Glu Tyr Ser Ile Ala Asp Gly Gly Val
180 185 190

Ala Lys Tyr Lys Asn Tyr Ile Asp Thr Ile Arg Gln Ile Val Val Glu
195 200 205

Tyr Ser Asp Ile Arg Thr Leu Leu Val Ile Glu Pro Asp Ser Leu Ala
210 215 220

Asn Leu Val Thr Asn Leu Asp Thr Pro Lys Cys Ala Asn Ala Gln Ser
225 230 235 240

```
Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445


<210> SEQ ID NO 17
<211> LENGTH: 447
<212> TYPE: PRT
<213> ORGANISM: Trichoderma reesei

<400> SEQUENCE: 17

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Asp Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
```

```
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Lys Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445


<210> SEQ ID NO 18
<211> LENGTH: 447
<212> TYPE: PRT
<213> ORGANISM: Trichoderma reesei

<400> SEQUENCE: 18

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Phe Gln Cys Leu Pro Asp Ala Ala Ser Ser Asn Ser Ser Thr
        35                  40                  45

Arg Ala Ala Ser Thr Thr Ser Arg Val Ser Pro Thr Thr Ser Leu Ser
    50                  55                  60

Ser Ser Ala Thr Pro Pro Thr Asp Ser Thr Thr Ala Arg Val Pro Pro
65                  70                  75                  80

Asp Gly Ser Gly Thr Ala Thr Tyr Ser Gly Asn Pro Phe Val Gly Val
                85                  90                  95
```

```
Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445


<210> SEQ ID NO 19
<211> LENGTH: 427
<212> TYPE: PRT
<213> ORGANISM: Trichoderma reesei

<400> SEQUENCE: 19

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30
```

```
Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Ser Gly
    50                  55                  60

Thr Ala Thr Tyr Ser Gly Asn Pro Phe Val Gly Val Thr Pro Trp Ala
65                  70                  75                  80

Asn Ala Tyr Tyr Ala Ser Glu Val Ser Ser Leu Ala Ile Pro Ser Leu
                85                  90                  95

Thr Gly Ala Met Ala Thr Ala Ala Ala Ala Val Ala Lys Val Pro Ser
            100                 105                 110

Phe Met Trp Leu Asp Thr Leu Asp Lys Thr Pro Leu Met Glu Gln Thr
        115                 120                 125

Leu Ala Asp Ile Arg Thr Ala Asn Lys Asn Gly Gly Asn Tyr Ala Gly
    130                 135                 140

Gln Phe Val Val Tyr Asp Leu Pro Asp Arg Asp Cys Ala Ala Leu Ala
145                 150                 155                 160

Ser Asn Gly Glu Tyr Ser Ile Ala Asp Gly Gly Val Ala Lys Tyr Lys
                165                 170                 175

Asn Tyr Ile Asp Thr Ile Arg Gln Ile Val Val Glu Tyr Ser Asp Ile
            180                 185                 190

Arg Thr Leu Leu Val Ile Glu Pro Asp Ser Leu Ala Asn Leu Val Thr
        195                 200                 205

Asn Leu Gly Thr Pro Lys Cys Ala Asn Ala Gln Ser Ala Tyr Leu Glu
    210                 215                 220

Cys Ile Asn Tyr Ala Val Thr Gln Leu Asn Leu Pro Asn Val Ala Met
225                 230                 235                 240

Tyr Leu Asp Ala Gly His Ala Gly Trp Leu Gly Trp Pro Ala Asn Gln
                245                 250                 255

Asp Pro Ala Ala Gln Leu Phe Ala Asn Val Tyr Lys Asn Ala Ser Ser
            260                 265                 270

Pro Arg Ala Leu Arg Gly Leu Ala Thr Asn Val Ala Asn Tyr Asn Gly
        275                 280                 285

Trp Asn Ile Thr Ser Pro Pro Ser Tyr Thr Gln Gly Asn Ala Val Tyr
    290                 295                 300

Asn Glu Lys Leu Tyr Ile His Ala Ile Gly Pro Leu Leu Ala Asn His
305                 310                 315                 320

Gly Trp Ser Asn Ala Phe Phe Ile Thr Asp Gln Gly Arg Ser Gly Lys
                325                 330                 335

Gln Pro Thr Gly Gln Gln Gln Trp Gly Asp Trp Cys Asn Val Ile Gly
            340                 345                 350

Thr Gly Phe Gly Ile Arg Pro Ser Ala Asn Thr Gly Asp Ser Leu Leu
        355                 360                 365

Asp Ser Phe Val Trp Val Lys Pro Gly Gly Glu Cys Asp Gly Thr Ser
    370                 375                 380

Asp Ser Ser Ala Pro Arg Phe Asp Pro His Cys Ala Leu Pro Asp Ala
385                 390                 395                 400

Leu Gln Pro Ala Pro Gln Ala Gly Ala Trp Phe Gln Ala Tyr Phe Val
                405                 410                 415

Gln Leu Leu Thr Asn Ala Asn Pro Ser Phe Leu
            420                 425
```

<210> SEQ ID NO 20
<211> LENGTH: 427

```
<212> TYPE: PRT
<213> ORGANISM: Trichoderma reesei

<400> SEQUENCE: 20

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Thr Thr Ser Arg Ser Ser Ala Thr
        35                  40                  45

Pro Pro Pro Gly Ser Thr Thr Thr Arg Val Pro Pro Val Gly Ser Gly
    50                  55                  60

Thr Ala Thr Tyr Ser Gly Asn Pro Phe Val Gly Val Thr Pro Trp Ala
65                  70                  75                  80

Asn Ala Tyr Tyr Ala Ser Glu Val Ser Ser Leu Ala Ile Pro Ser Leu
                85                  90                  95

Thr Gly Ala Met Ala Thr Ala Ala Ala Ala Val Ala Lys Val Pro Ser
            100                 105                 110

Phe Met Trp Leu Asp Thr Leu Asp Lys Thr Pro Leu Met Glu Gln Thr
        115                 120                 125

Leu Ala Asp Ile Arg Thr Ala Asn Lys Asn Gly Gly Asn Tyr Ala Gly
    130                 135                 140

Gln Phe Val Val Tyr Asp Leu Pro Asp Arg Asp Cys Ala Ala Leu Ala
145                 150                 155                 160

Ser Asn Gly Glu Tyr Ser Ile Ala Asp Gly Gly Val Ala Lys Tyr Lys
                165                 170                 175

Asn Tyr Ile Asp Thr Ile Arg Gln Ile Val Val Glu Tyr Ser Asp Ile
            180                 185                 190

Arg Thr Leu Leu Val Ile Glu Pro Asp Ser Leu Ala Asn Leu Val Thr
        195                 200                 205

Asn Leu Gly Thr Pro Lys Cys Ala Asn Ala Gln Ser Ala Tyr Leu Glu
    210                 215                 220

Cys Ile Asn Tyr Ala Val Thr Gln Leu Asn Leu Pro Asn Val Ala Met
225                 230                 235                 240

Tyr Leu Asp Ala Gly His Ala Gly Trp Leu Gly Trp Pro Ala Asn Gln
                245                 250                 255

Asp Pro Ala Ala Gln Leu Phe Ala Asn Val Tyr Lys Asn Ala Ser Ser
            260                 265                 270

Pro Arg Ala Leu Arg Gly Leu Ala Thr Asn Val Ala Asn Tyr Asn Gly
        275                 280                 285

Trp Asn Ile Thr Ser Pro Pro Ser Tyr Thr Gln Gly Asn Ala Val Tyr
    290                 295                 300

Asn Glu Lys Leu Tyr Ile His Ala Ile Gly Pro Leu Leu Ala Asn His
305                 310                 315                 320

Gly Trp Ser Asn Ala Phe Phe Ile Thr Asp Gln Gly Arg Ser Gly Lys
                325                 330                 335

Gln Pro Thr Gly Gln Gln Gln Trp Gly Asp Trp Cys Asn Val Ile Gly
            340                 345                 350

Thr Gly Phe Gly Ile Arg Pro Ser Ala Asn Thr Gly Asp Ser Leu Leu
        355                 360                 365

Asp Ser Phe Val Trp Val Lys Pro Gly Gly Glu Cys Asp Gly Thr Ser
    370                 375                 380

Asp Ser Ser Ala Pro Arg Phe Asp Pro His Cys Ala Leu Pro Asp Ala
385                 390                 395                 400
```

```
Leu Gln Pro Ala Pro Gln Ala Gly Ala Trp Phe Gln Ala Tyr Phe Val
                405                 410                 415

Gln Leu Leu Thr Asn Ala Asn Pro Ser Phe Leu
            420                 425


<210> SEQ ID NO 21
<211> LENGTH: 447
<212> TYPE: PRT
<213> ORGANISM: Trichoderma reesei

<400> SEQUENCE: 21

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Glu Ala Ala Ser Thr Thr Ser Glu Val Ser Pro Thr Thr Ser Glu Ser
    50                  55                  60

Ser Ser Ala Thr Pro Pro Pro Gly Ser Thr Thr Thr Glu Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
```

```
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445


<210> SEQ ID NO 22
<211> LENGTH: 447
<212> TYPE: PRT
<213> ORGANISM: Trichoderma reesei

<400> SEQUENCE: 22

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Thr Thr Thr Thr Thr Thr
        35                  40                  45

Arg Ala Ala Thr Thr Thr Thr Arg Val Thr Pro Thr Thr Thr Arg Thr
    50                  55                  60

Thr Thr Ala Thr Pro Pro Pro Gly Thr Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270
```

```
Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445


<210> SEQ ID NO 23
<211> LENGTH: 447
<212> TYPE: PRT
<213> ORGANISM: Trichoderma reesei

<400> SEQUENCE: 23

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Thr Thr Thr Thr Thr Thr
        35                  40                  45

Glu Ala Ala Thr Thr Thr Thr Glu Val Thr Pro Thr Thr Thr Glu Thr
    50                  55                  60

Thr Thr Ala Thr Pro Pro Pro Gly Thr Thr Thr Thr Glu Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205
```

```
Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445


<210> SEQ ID NO 24
<211> LENGTH: 497
<212> TYPE: PRT
<213> ORGANISM: Trichoderma reesei

<400> SEQUENCE: 24

Gln Ser Ala Cys Thr Leu Gln Ser Glu Thr His Pro Pro Leu Thr Trp
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
```

```
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
        355                 360                 365

Asp Tyr Tyr Ala Asn Met Leu Trp Leu Asp Ser Thr Tyr Pro Thr Asn
    370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
            420                 425                 430

Ser Gly Gly Asn Pro Pro Gly Gly Asn Pro Pro Gly Thr Thr Thr Thr
        435                 440                 445

Glu Glu Pro Ala Thr Thr Thr Gly Ser Ser Pro Gly Pro Thr Gln Ser
    450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495

Leu


<210> SEQ ID NO 25
<211> LENGTH: 497
<212> TYPE: PRT
<213> ORGANISM: Trichoderma reesei

<400> SEQUENCE: 25

Gln Ser Ala Cys Thr Leu Gln Ser Glu Thr His Pro Pro Leu Thr Trp
```

```
1               5                   10                  15

Gln Lys Cys Ser Ser Gly Gly Thr Cys Thr Gln Gln Thr Gly Ser Val
            20                  25                  30

Val Ile Asp Ala Asn Trp Arg Trp Thr His Ala Thr Asn Ser Ser Thr
        35                  40                  45

Asn Cys Tyr Asp Gly Asn Thr Trp Ser Ser Thr Leu Cys Pro Asp Asn
    50                  55                  60

Glu Thr Cys Ala Lys Asn Cys Cys Leu Asp Gly Ala Ala Tyr Ala Ser
65                  70                  75                  80

Thr Tyr Gly Val Thr Thr Ser Gly Asn Ser Leu Ser Ile Gly Phe Val
                85                  90                  95

Thr Gln Ser Ala Gln Lys Asn Val Gly Ala Arg Leu Tyr Leu Met Ala
            100                 105                 110

Ser Asp Thr Thr Tyr Gln Glu Phe Thr Leu Leu Gly Asn Glu Phe Ser
        115                 120                 125

Phe Asp Val Asp Val Ser Gln Leu Pro Cys Gly Leu Asn Gly Ala Leu
    130                 135                 140

Tyr Phe Val Ser Met Asp Ala Asp Gly Gly Val Ser Lys Tyr Pro Thr
145                 150                 155                 160

Asn Thr Ala Gly Ala Lys Tyr Gly Thr Gly Tyr Cys Asp Ser Gln Cys
                165                 170                 175

Pro Arg Asp Leu Lys Phe Ile Asn Gly Gln Ala Asn Val Glu Gly Trp
            180                 185                 190

Glu Pro Ser Ser Asn Asn Ala Asn Thr Gly Ile Gly Gly His Gly Ser
        195                 200                 205

Cys Cys Ser Glu Met Asp Ile Trp Glu Ala Asn Ser Ile Ser Glu Ala
    210                 215                 220

Leu Thr Pro His Pro Cys Thr Thr Val Gly Gln Glu Ile Cys Glu Gly
225                 230                 235                 240

Asp Gly Cys Gly Gly Thr Tyr Ser Asp Asn Arg Tyr Gly Gly Thr Cys
                245                 250                 255

Asp Pro Asp Gly Cys Asp Trp Asn Pro Tyr Arg Leu Gly Asn Thr Ser
            260                 265                 270

Phe Tyr Gly Pro Gly Ser Ser Phe Thr Leu Asp Thr Thr Lys Lys Leu
        275                 280                 285

Thr Val Val Thr Gln Phe Glu Thr Ser Gly Ala Ile Asn Arg Tyr Tyr
    290                 295                 300

Val Gln Asn Gly Val Thr Phe Gln Gln Pro Asn Ala Glu Leu Gly Ser
305                 310                 315                 320

Tyr Ser Gly Asn Glu Leu Asn Asp Asp Tyr Cys Thr Ala Glu Glu Ala
                325                 330                 335

Glu Phe Gly Gly Ser Ser Phe Ser Asp Lys Gly Gly Leu Thr Gln Phe
            340                 345                 350

Lys Lys Ala Thr Ser Gly Gly Met Val Leu Val Met Ser Leu Trp Asp
        355                 360                 365

Asp Tyr Tyr Ala Asn Met Leu Trp Leu Asp Ser Thr Tyr Pro Thr Asn
    370                 375                 380

Glu Thr Ser Ser Thr Pro Gly Ala Val Arg Gly Ser Cys Ser Thr Ser
385                 390                 395                 400

Ser Gly Val Pro Ala Gln Val Glu Ser Gln Ser Pro Asn Ala Lys Val
                405                 410                 415

Thr Phe Ser Asn Ile Lys Phe Gly Pro Ile Gly Ser Thr Gly Asn Pro
            420                 425                 430
```

```
Ser Gly Gly Asn Pro Pro Gly Gly Asn Pro Pro Gly Thr Thr Thr Thr
        435                 440                 445

Glu Glu Pro Ala Thr Thr Thr Gly Thr Thr Pro Gly Pro Thr Gln Ser
    450                 455                 460

His Tyr Gly Gln Cys Gly Gly Ile Gly Tyr Ser Gly Pro Thr Val Cys
465                 470                 475                 480

Ala Ser Gly Thr Thr Cys Gln Val Leu Asn Pro Tyr Tyr Ser Gln Cys
                485                 490                 495

Leu


<210> SEQ ID NO 26
<211> LENGTH: 44
<212> TYPE: PRT
<213> ORGANISM: Trichoderma reesei

<400> SEQUENCE: 26

Pro Asp Ala Ala Ser Ser Ser Ser Ser Thr Arg Ala Ala Ser Thr Thr
1               5                   10                  15

Ser Arg Val Ser Pro Thr Thr Ser Arg Ser Ser Ser Ala Thr Pro Pro
            20                  25                  30

Pro Gly Ser Thr Thr Thr Arg Val Pro Pro Val Gly
        35                  40


<210> SEQ ID NO 27
<211> LENGTH: 44
<212> TYPE: PRT
<213> ORGANISM: Trichoderma reesei

<400> SEQUENCE: 27

Pro Gly Ala Ala Ser Ser Asn Ser Ser Thr Arg Ala Ala Ser Thr Thr
1               5                   10                  15

Ser Arg Val Ser Pro Thr Thr Ser Arg Ser Ser Ser Ala Thr Pro Pro
            20                  25                  30

Pro Gly Ser Thr Thr Thr Arg Val Pro Pro Val Gly
        35                  40


<210> SEQ ID NO 28
<211> LENGTH: 44
<212> TYPE: PRT
<213> ORGANISM: Trichoderma reesei

<400> SEQUENCE: 28

Pro Gly Ala Ala Ser Ser Ser Ser Ser Thr Arg Ala Ala Ser Thr Thr
1               5                   10                  15

Ser Arg Val Ser Pro Thr Thr Ser Leu Ser Ser Ser Ala Thr Pro Pro
            20                  25                  30

Pro Gly Ser Thr Thr Thr Arg Val Pro Pro Val Gly
        35                  40


<210> SEQ ID NO 29
<211> LENGTH: 44
<212> TYPE: PRT
<213> ORGANISM: Trichoderma reesei

<400> SEQUENCE: 29

Pro Gly Ala Ala Ser Ser Ser Ser Ser Thr Arg Ala Ala Ser Thr Thr
1               5                   10                  15

Ser Arg Val Ser Pro Thr Thr Ser Arg Ser Ser Ser Ala Thr Pro Pro
            20                  25                  30
```

```
Pro Asp Ser Thr Thr Thr Arg Val Pro Pro Val Gly
        35                  40


<210> SEQ ID NO 30
<211> LENGTH: 44
<212> TYPE: PRT
<213> ORGANISM: Trichoderma reesei

<400> SEQUENCE: 30

Pro Gly Ala Ala Ser Ser Ser Ser Ser Thr Arg Ala Ala Ser Thr Thr
1               5                   10                  15

Ser Arg Val Ser Pro Thr Thr Ser Arg Ser Ser Ser Ala Thr Pro Pro
            20                  25                  30

Pro Gly Ser Thr Thr Ala Arg Val Pro Pro Val Gly
        35                  40


<210> SEQ ID NO 31
<211> LENGTH: 44
<212> TYPE: PRT
<213> ORGANISM: Trichoderma reesei

<400> SEQUENCE: 31

Pro Gly Ala Ala Ser Ser Ser Ser Ser Thr Arg Ala Ala Ser Thr Thr
1               5                   10                  15

Ser Arg Val Ser Pro Thr Thr Ser Arg Ser Ser Ser Ala Thr Pro Pro
            20                  25                  30

Pro Gly Ser Thr Thr Thr Arg Val Pro Pro Asp Gly
        35                  40


<210> SEQ ID NO 32
<211> LENGTH: 44
<212> TYPE: PRT
<213> ORGANISM: Trichoderma reesei

<400> SEQUENCE: 32

Pro Gly Ala Ala Ser Ser Ser Ser Ser Thr Arg Ala Ala Ser Thr Thr
1               5                   10                  15

Ser Arg Val Ser Pro Thr Thr Ser Arg Ser Ser Ser Ala Thr Pro Pro
            20                  25                  30

Thr Gly Ser Thr Thr Thr Arg Val Pro Pro Val Gly
        35                  40


<210> SEQ ID NO 33
<211> LENGTH: 44
<212> TYPE: PRT
<213> ORGANISM: Trichoderma reesei

<400> SEQUENCE: 33

Pro Gly Ala Ala Ser Ser Ser Ser Ser Thr Glu Ala Ala Ser Thr Thr
1               5                   10                  15

Ser Glu Val Ser Pro Thr Thr Ser Glu Ser Ser Ser Ala Thr Pro Pro
            20                  25                  30

Pro Gly Ser Thr Thr Thr Glu Val Pro Pro Val Gly
        35                  40


<210> SEQ ID NO 34
<211> LENGTH: 44
<212> TYPE: PRT
<213> ORGANISM: Trichoderma reesei

<400> SEQUENCE: 34
```

```
Pro Asp Ala Ala Ser Ser Asn Ser Ser Thr Arg Ala Ala Ser Thr Thr
1               5                   10                  15

Ser Arg Val Ser Pro Thr Thr Ser Leu Ser Ser Ser Ala Thr Pro Pro
            20                  25                  30

Thr Asp Ser Thr Thr Ala Arg Val Pro Pro Asp Gly
        35                  40


<210> SEQ ID NO 35
<211> LENGTH: 24
<212> TYPE: PRT
<213> ORGANISM: Trichoderma reesei

<400> SEQUENCE: 35

Pro Gly Ala Ala Ser Ser Ser Ser Ser Thr Arg Ala Ala Ser Thr Thr
1               5                   10                  15

Ser Arg Val Ser Pro Thr Thr Ser
            20


<210> SEQ ID NO 36
<211> LENGTH: 24
<212> TYPE: PRT
<213> ORGANISM: Trichoderma reesei

<400> SEQUENCE: 36

Pro Thr Thr Ser Arg Ser Ser Ser Ala Thr Pro Pro Pro Gly Ser Thr
1               5                   10                  15

Thr Thr Arg Val Pro Pro Val Gly
            20


<210> SEQ ID NO 37
<211> LENGTH: 44
<212> TYPE: PRT
<213> ORGANISM: Trichoderma reesei

<400> SEQUENCE: 37

Pro Gly Ala Ala Thr Thr Thr Thr Thr Thr Arg Ala Ala Thr Thr Thr
1               5                   10                  15

Thr Arg Val Thr Pro Thr Thr Thr Arg Thr Thr Thr Ala Thr Pro Pro
            20                  25                  30

Pro Gly Thr Thr Thr Thr Arg Val Pro Pro Val Gly
        35                  40


<210> SEQ ID NO 38
<211> LENGTH: 44
<212> TYPE: PRT
<213> ORGANISM: Trichoderma reesei

<400> SEQUENCE: 38

Pro Gly Ala Ala Thr Thr Thr Thr Thr Thr Glu Ala Ala Thr Thr Thr
1               5                   10                  15

Thr Glu Val Thr Pro Thr Thr Thr Glu Thr Thr Thr Ala Thr Pro Pro
            20                  25                  30

Pro Gly Thr Thr Thr Thr Glu Val Pro Pro Val Gly
        35                  40


<210> SEQ ID NO 39
<211> LENGTH: 25
<212> TYPE: PRT
<213> ORGANISM: Trichoderma reesei

<400> SEQUENCE: 39
```

```
Pro Pro Gly Gly Asn Pro Pro Gly Thr Thr Thr Thr Arg Arg Pro Ala
1               5                   10                  15

Thr Thr Thr Gly Ser Ser Pro Gly Pro
            20                  25


<210> SEQ ID NO 40
<211> LENGTH: 25
<212> TYPE: PRT
<213> ORGANISM: Trichoderma reesei

<400> SEQUENCE: 40

Pro Pro Gly Gly Asn Pro Pro Gly Thr Thr Thr Thr Glu Glu Pro Ala
1               5                   10                  15

Thr Thr Thr Gly Ser Ser Pro Gly Pro
            20                  25


<210> SEQ ID NO 41
<211> LENGTH: 25
<212> TYPE: PRT
<213> ORGANISM: Trichoderma reesei

<400> SEQUENCE: 41

Pro Pro Gly Gly Asn Pro Pro Gly Thr Thr Thr Thr Glu Glu Pro Ala
1               5                   10                  15

Thr Thr Thr Gly Thr Thr Pro Gly Pro
            20                  25


<210> SEQ ID NO 42
<211> LENGTH: 34
<212> TYPE: PRT
<213> ORGANISM: Trichoderma reesei

<400> SEQUENCE: 42

Pro Gly Ala Thr Thr Ile Thr Thr Ser Thr Arg Pro Pro Ser Gly Pro
1               5                   10                  15

Thr Thr Thr Thr Arg Ala Thr Ser Thr Ser Ser Ser Thr Pro Pro Thr
            20                  25                  30

Ser Ser


<210> SEQ ID NO 43
<211> LENGTH: 29
<212> TYPE: PRT
<213> ORGANISM: Trichoderma reesei

<400> SEQUENCE: 43

Pro Pro Pro Pro Pro Ala Ser Ser Thr Thr Phe Ser Thr Thr Arg Arg
1               5                   10                  15

Ser Ser Thr Thr Ser Ser Ser Pro Ser Cys Thr Gln Thr
            20                  25


<210> SEQ ID NO 44
<211> LENGTH: 23
<212> TYPE: PRT
<213> ORGANISM: Trichoderma reesei

<400> SEQUENCE: 44

Asp Thr Gly Ser Thr Pro Pro Gly Ser Ser Pro Pro Ala Thr Ser Ser
1               5                   10                  15

Ser Pro Pro Ser Gly Gly Gly
            20
```

<210> SEQ ID NO 45
<211> LENGTH: 51
<212> TYPE: PRT
<213> ORGANISM: Trichoderma reesei

<400> SEQUENCE: 45

```
Ser Ser Ala Ala Thr Ala Thr Ala Ser Ala Thr Val Pro Gly Gly Gly
1               5                   10                  15

Ser Gly Pro Thr Ser Arg Thr Thr Thr Thr Ala Arg Thr Thr Gln Ala
            20                  25                  30

Ser Ser Arg Pro Ser Ser Thr Pro Pro Ala Thr Thr Ser Ala Pro Ala
        35                  40                  45

Gly Gly Pro
    50
```

<210> SEQ ID NO 46
<211> LENGTH: 43
<212> TYPE: PRT
<213> ORGANISM: Trichoderma reesei

<400> SEQUENCE: 46

```
Pro Gly Ser Pro Gly Gly Pro Gly Ser Ser Thr Thr Gly Arg Ser Ser
1               5                   10                  15

Thr Ser Gly Pro Thr Ser Thr Ser Arg Pro Ser Thr Thr Ile Pro Pro
            20                  25                  30

Pro Thr Ser Arg Thr Thr Thr Ala Thr Gly Pro
        35                  40
```

<210> SEQ ID NO 47
<211> LENGTH: 45
<212> TYPE: PRT
<213> ORGANISM: Trichoderma reesei

<400> SEQUENCE: 47

```
Pro Pro Asn Gly Thr Thr Ser Ser Ser Leu Val Ser Arg Thr Ser Ser
1               5                   10                  15

Ala Ser Ser Ser Val Gly Ser Ser Ser Pro Gly Gly Asn Ser Pro Thr
            20                  25                  30

Gly Ser Ala Ser Thr Tyr Thr Thr Thr Asp Thr Ala Thr
        35                  40                  45
```

<210> SEQ ID NO 48
<211> LENGTH: 36
<212> TYPE: PRT
<213> ORGANISM: Trichoderma reesei

<400> SEQUENCE: 48

```
Gln Gln Thr Val Trp Gly Gln Cys Gly Gly Ile Gly Trp Ser Gly Pro
1               5                   10                  15

Thr Asn Cys Ala Pro Gly Ser Ala Cys Ser Thr Leu Asn Pro Tyr Tyr
            20                  25                  30

Ala Gln Cys Ile
        35
```

<210> SEQ ID NO 49
<211> LENGTH: 36
<212> TYPE: PRT
<213> ORGANISM: Trichoderma reesei

<400> SEQUENCE: 49

```
Cys Ser Ser Val Trp Gly Gln Cys Gly Gly Gln Asn Trp Ser Gly Pro
1               5                   10                  15

Thr Cys Cys Ala Ser Gly Ser Thr Cys Val Tyr Ser Asn Asp Tyr Tyr
            20                  25                  30

Ser Gln Cys Leu
        35


<210> SEQ ID NO 50
<211> LENGTH: 36
<212> TYPE: PRT
<213> ORGANISM: Trichoderma reesei

<400> SEQUENCE: 50

Thr Gln Ser His Tyr Gly Gln Cys Gly Gly Ile Gly Tyr Ser Gly Pro
1               5                   10                  15

Thr Val Cys Ala Ser Gly Thr Thr Cys Gln Val Leu Asn Pro Tyr Tyr
            20                  25                  30

Ser Gln Cys Leu
        35


<210> SEQ ID NO 51
<211> LENGTH: 36
<212> TYPE: PRT
<213> ORGANISM: Trichoderma reesei

<400> SEQUENCE: 51

Thr Gln Thr His Trp Gly Gln Cys Gly Gly Ile Gly Tyr Ser Gly Cys
1               5                   10                  15

Lys Thr Cys Thr Ser Gly Thr Thr Cys Gln Tyr Ser Asn Asp Tyr Tyr
            20                  25                  30

Ser Gln Cys Leu
        35


<210> SEQ ID NO 52
<211> LENGTH: 36
<212> TYPE: PRT
<213> ORGANISM: Trichoderma reesei

<400> SEQUENCE: 52

Gln Gln Thr Leu Tyr Gly Gln Cys Gly Gly Ala Gly Trp Thr Gly Pro
1               5                   10                  15

Thr Thr Cys Gln Ala Pro Gly Thr Cys Lys Val Gln Asn Gln Trp Tyr
            20                  25                  30

Ser Gln Cys Leu
        35


<210> SEQ ID NO 53
<211> LENGTH: 36
<212> TYPE: PRT
<213> ORGANISM: Trichoderma reesei

<400> SEQUENCE: 53

Thr Gln Thr Leu Tyr Gly Gln Cys Gly Gly Ser Gly Tyr Ser Gly Pro
1               5                   10                  15

Thr Arg Cys Ala Pro Pro Ala Thr Cys Ser Thr Leu Asn Pro Tyr Tyr
            20                  25                  30

Ala Gln Cys Leu
        35


<210> SEQ ID NO 54
```

<211> LENGTH: 36
<212> TYPE: PRT
<213> ORGANISM: Trichoderma reesei

<400> SEQUENCE: 54

```
Thr Gln Thr His Tyr Gly Gln Cys Gly Gly Ile Gly Tyr Ser Gly Pro
1               5                   10                  15

Thr Val Cys Ala Ser Gly Thr Thr Cys Gln Val Leu Asn Pro Tyr Tyr
            20                  25                  30

Ser Gln Cys Leu
        35
```

<210> SEQ ID NO 55
<211> LENGTH: 36
<212> TYPE: PRT
<213> ORGANISM: Trichoderma reesei

<400> SEQUENCE: 55

```
Cys Ala Ala Leu Phe Gly Gln Cys Gly Gly Ile Gly Trp Ser Gly Thr
1               5                   10                  15

Thr Cys Cys Val Ala Gly Ala Gln Cys Ser Phe Val Asn Asp Trp Tyr
            20                  25                  30

Ser Gln Cys Leu
        35
```

<210> SEQ ID NO 56
<211> LENGTH: 30
<212> TYPE: DNA
<213> ORGANISM: Artificial
<220> FEATURE:
<223> OTHER INFORMATION: Primer sequence

<400> SEQUENCE: 56
accaaaagat ctatgagatt tccttcaatt 30

<210> SEQ ID NO 57
<211> LENGTH: 30
<212> TYPE: DNA
<213> ORGANISM: Artificial
<220> FEATURE:
<223> OTHER INFORMATION: Primer sequence

<400> SEQUENCE: 57
tgagcagcta gcccttttat ccaaagatac 30

<210> SEQ ID NO 58
<211> LENGTH: 30
<212> TYPE: DNA
<213> ORGANISM: Artificial
<220> FEATURE:
<223> OTHER INFORMATION: Primer sequence

<400> SEQUENCE: 58
aaaagggcta gctgctcaag cgtctggggc 30

<210> SEQ ID NO 59
<211> LENGTH: 36
<212> TYPE: DNA
<213> ORGANISM: Artificial
<220> FEATURE:
<223> OTHER INFORMATION: Primer sequence

<400> SEQUENCE: 59
gagctcagat ctggtacctt acaggaacga tgggtt 36

<210> SEQ ID NO 60
<211> LENGTH: 99
<212> TYPE: DNA
<213> ORGANISM: Artificial
<220> FEATURE:
<223> OTHER INFORMATION: Primer sequence

<400> SEQUENCE: 60
cgttgtgggg gatactcgag aagtcgtcga cgcggcgcgc gtggacgagt ttgagcttgc 60
agcatcggga agacactgaa agtaatagtc gttggagta 99

<210> SEQ ID NO 61
<211> LENGTH: 96
<212> TYPE: DNA
<213> ORGANISM: Artificial
<220> FEATURE:
<223> OTHER INFORMATION: Primer sequence

<400> SEQUENCE: 61
cgagtatccc ccacaacgtc cctgtcgagc tccgcgacgc ctccaactga ttctactact 60
gctagagtac ctccagatgg atcgggaacc gctacg 96

<210> SEQ ID NO 62
<211> LENGTH: 21
<212> TYPE: DNA
<213> ORGANISM: Artificial
<220> FEATURE:
<223> OTHER INFORMATION: Primer sequence

<400> SEQUENCE: 62
agcacaaata acgggttatt g 21

<210> SEQ ID NO 63
<211> LENGTH: 23
<212> TYPE: DNA
<213> ORGANISM: Artificial
<220> FEATURE:
<223> OTHER INFORMATION: Primer sequence

<400> SEQUENCE: 63
gcaacacctg gcaattcctt acc 23

<210> SEQ ID NO 64
<211> LENGTH: 24
<212> TYPE: DNA
<213> ORGANISM: Artificial
<220> FEATURE:
<223> OTHER INFORMATION: Primer sequence

<400> SEQUENCE: 64
ggatgttgtg ggggatactc gaga 24

<210> SEQ ID NO 65
<211> LENGTH: 39
<212> TYPE: DNA
<213> ORGANISM: Artificial
<220> FEATURE:
<223> OTHER INFORMATION: Primer sequence

<400> SEQUENCE: 65
tctcgagtat cccccacaac atcctcggga accgctacg 39

<210> SEQ ID NO 66

<211> LENGTH: 39
<212> TYPE: DNA
<213> ORGANISM: Artificial
<220> FEATURE:
<223> OTHER INFORMATION: Primer sequence

<400> SEQUENCE: 66
ggagctcgac cgggatgttg tgggaagaca ctgggagta 39

<210> SEQ ID NO 67
<211> LENGTH: 24
<212> TYPE: DNA
<213> ORGANISM: Artificial
<220> FEATURE:
<223> OTHER INFORMATION: Primer sequence

<400> SEQUENCE: 67
cccacaacat cccggtcgag ctcc 24

<210> SEQ ID NO 68
<211> LENGTH: 60
<212> TYPE: DNA
<213> ORGANISM: Artificial
<220> FEATURE:
<223> OTHER INFORMATION: Primer sequence

<400> SEQUENCE: 68
ggacgttgtg ggggatactt cagaagtcgt cgacgcggct tccgtggacg agcttgagct 60

<210> SEQ ID NO 69
<211> LENGTH: 81
<212> TYPE: DNA
<213> ORGANISM: Artificial
<220> FEATURE:
<223> OTHER INFORMATION: Primer sequence

<400> SEQUENCE: 69
gtatccccca caacgtccga atcgagctcc gcgacgcctc cacctggttc tactactacc 60
gaagtacctc cagtcggatc g 81

<210> SEQ ID NO 70
<211> LENGTH: 81
<212> TYPE: DNA
<213> ORGANISM: Artificial
<220> FEATURE:
<223> OTHER INFORMATION: Primer sequence

<400> SEQUENCE: 70
ttcagtcgtt gtgggagtta cttcagtagt cgtagtcgcg gcttccgtag tagtagtagt 60
agttgcagcg ccgggaagac a 81

<210> SEQ ID NO 71
<211> LENGTH: 78
<212> TYPE: DNA
<213> ORGANISM: Artificial
<220> FEATURE:
<223> OTHER INFORMATION: Primer sequence

<400> SEQUENCE: 71
actcccacaa cgactgaaac tactactgcg acgcctccac ctggtactac tactaccgaa 60
gtacctccag tcggatcg 78

<210> SEQ ID NO 72
<211> LENGTH: 34

<212> TYPE: DNA
<213> ORGANISM: Artificial
<220> FEATURE:
<223> OTHER INFORMATION: Primer sequence

<400> SEQUENCE: 72
ctgggtacct tacaggcact gagagtagta aggg 34

<210> SEQ ID NO 73
<211> LENGTH: 29
<212> TYPE: DNA
<213> ORGANISM: Artificial
<220> FEATURE:
<223> OTHER INFORMATION: Primer sequence

<400> SEQUENCE: 73
gtcgaattcg tcttctctag gtgccattc 29

<210> SEQ ID NO 74
<211> LENGTH: 21
<212> TYPE: DNA
<213> ORGANISM: Artificial
<220> FEATURE:
<223> OTHER INFORMATION: Primer sequence

<400> SEQUENCE: 74
cctgtaaggt acccggcttt c 21

<210> SEQ ID NO 75
<211> LENGTH: 21
<212> TYPE: DNA
<213> ORGANISM: Artificial
<220> FEATURE:
<223> OTHER INFORMATION: Primer sequence

<400> SEQUENCE: 75
cccgtggatc ctcattcaag c 21

<210> SEQ ID NO 76
<211> LENGTH: 27
<212> TYPE: DNA
<213> ORGANISM: Artificial
<220> FEATURE:
<223> OTHER INFORMATION: Primer sequence

<400> SEQUENCE: 76
gtattggctg cagcggcccc acggtct 27

<210> SEQ ID NO 77
<211> LENGTH: 27
<212> TYPE: DNA
<213> ORGANISM: Artificial
<220> FEATURE:
<223> OTHER INFORMATION: Primer sequence

<400> SEQUENCE: 77
gcccggctgc agagctcatg cgcaaag 27

<210> SEQ ID NO 78
<211> LENGTH: 18
<212> TYPE: DNA
<213> ORGANISM: Artificial
<220> FEATURE:
<223> OTHER INFORMATION: Primer sequence

<400> SEQUENCE: 78
gcctgcactc tccaatcg 18

<210> SEQ ID NO 79
<211> LENGTH: 46
<212> TYPE: DNA
<213> ORGANISM: Artificial
<220> FEATURE:
<223> OTHER INFORMATION: Primer sequence

<400> SEQUENCE: 79
gcttccagtg gtagtggctg gctcctcggt ggtggtggtg ccaggc 46

<210> SEQ ID NO 80
<211> LENGTH: 46
<212> TYPE: DNA
<213> ORGANISM: Artificial
<220> FEATURE:
<223> OTHER INFORMATION: Primer sequence

<400> SEQUENCE: 80
gcctggcacc accaccaccg aggagccagc cactaccact ggaagc 46

<210> SEQ ID NO 81
<211> LENGTH: 70
<212> TYPE: DNA
<213> ORGANISM: Artificial
<220> FEATURE:
<223> OTHER INFORMATION: Primer sequence

<400> SEQUENCE: 81
gtgagactgg gtaggtccgg gggtggttcc agtggtagtg gctggctcct cggtggtggt 60
ggtgccaggc 70

<210> SEQ ID NO 82
<211> LENGTH: 70
<212> TYPE: DNA
<213> ORGANISM: Artificial
<220> FEATURE:
<223> OTHER INFORMATION: Primer sequence

<400> SEQUENCE: 82
gcctggcacc accaccaccg aggagccagc cactaccact ggaaccaccc ccggacctac 60
ccagtctcac 70

<210> SEQ ID NO 83
<211> LENGTH: 44
<212> TYPE: PRT
<213> ORGANISM: Trichoderma reesei

<400> SEQUENCE: 83

Pro Gly Ala Ala Ser Ser Ser Ser Ser Thr Arg Ala Ala Ser Thr Thr
1 5 10 15

Ser Arg Val Ser Pro Thr Thr Ser Arg Ser Ser Ser Ala Thr Pro Pro
20 25 30

Pro Gly Ser Thr Thr Thr Arg Val Pro Pro Val Gly
35 40

CELLULASE ENZYMES HAVING A MODIFIED LINKER AND REDUCED LIGNIN BINDING

RELATED APPLICATIONS

This application is a continuation of U.S. patent application Ser. No. 12/713,516, filed Feb. 26, 2010, which claims the priority benefit of a provisional application entitled NOVEL LIGNIN-RESISTANT CELLULASE ENZYME, U.S. Provisional Application No. 61/156,337, filed Feb. 27, 2009. The entire contents of the aforementioned applications are incorporated herein by reference.

FIELD OF THE INVENTION

The present invention relates to modified cellulase enzymes. More specifically, the invention relates to cellulase enzymes with modified linker peptides that confer resistance to lignin binding to the modified cellulase enzymes. The present invention also relates to genetic constructs comprising nucleic acid sequences encoding for the modified cellulase enzymes, methods for the production of the modified cellulase enzymes from host strains and the a process for hydrolysing cellulose with the modified cellulase enzymes in the presence of lignin.

BACKGROUND OF THE INVENTION

More than 50% of organic carbon on earth is found in the cell walls of plants. Plant cell walls consist mainly of three compounds: cellulose, hemicellulose, and lignin. Collectively these compounds are called "lignocellulose," and they represent a potential source of sugars and other organic molecules for fermentation to ethanol or to other high-value products.

The conversion of lignocellulosic biomass to ethanol has become a key feature of emerging energy policies due to the environmentally favorable and sustainable nature of cellulosic ethanol. There are several technologies being developed for cellulose conversion. Of interest here is a method by which lignocellulosic biomass is subjected to a pretreatment that increases its susceptibility to hydrolytic enzymes, followed by enzymatic hydrolysis to sugars and the fermentation of those sugars to ethanol or other high-value organic molecules (e.g. butanol). Common pretreatment methods include dilute acid steam explosion (U.S. Pat. No. 4,461,648), ammonia freeze explosion (AFEX; Holtzapple et al., 1991), and organosolv extraction (U.S. Pat. No. 4,409,032). Hydrolysis and fermentation systems may be either separate (sequential hydrolysis and fermentation; SHF) or coincident (simultaneous saccharification and fermentation; SSF). In all instances, the hemicellulose and cellulose are broken down to sugars that may be fermented, while the lignin becomes separated and may be used either as a solid fuel or as a source for other organic molecules.

The choice of enzymes for conversion of pretreated lignocellulosic biomass to sugars is highly dependent upon the pretreatment method. Dilute acid steam explosion results in significant chemical hydrolysis of the hemicellulose, making enzymes for the conversion of hemicellulose to sugars less relevant to the process. In contrast, AFEX and organosolv extraction both leave hemicellulose and cellulose largely intact. Organosolv extraction, unlike dilute acid steam explosion or AFEX removes a significant portion of the lignin from substrate. In all instances, the primary target for enzymatic hydrolysis is the cellulose, which is converted to sugars using a combination of cellulase enzymes.

There are two principle types of cellulase enzymes: endoglucanases, which cleave glycosidic bonds in the middle of cellulose chains, and in doing so create new chain ends, and cellobiohydrolases, which cleave short oligosaccharides from the ends of cellulose chains. Glucosidases digest short oligosaccharides into monosaccharides. These three enzyme components thus act synergistically to create an efficient cellulolytic enzyme system. Most cellulases have a similar modular structure, which consists of a catalytic domain, linker peptide and a carbohydrate-binding module (CBM).

Fungal CBMs (Family 1) consist of a small wedge-shaped fold. Three solvent exposed hydrophobic (aromatic) residues lie on one surface of this fold and constitute the cellulose binding surface (Kraulis et al., 1989; Mattinen et al., 1997). These aromatic residues form van der Waals interactions and aromatic ring polarization interactions with glucose rings in the cellulose polymer (Mattinen et al., 1997; Reinikainen et al., 1992, Tormo et al., 1996). CBMs are reportedly involved in lignin binding. For example, removal of the CBM from *Trichoderma* Cel7A essentially eliminates binding to alkali extracted lignin and to residual lignin prepared by enzyme hydrolysis (Palonen et al., 2004).

Catalytic domains are also reportedly involved in binding lignin. Cel7B from *Humicola* sp., which does not possess a CBM, is bound extensively by lignin (Berlin et al., 2005b). Similarly *Trichoderma* Cel5A core, devoid of a CBM, binds alkali extracted lignin but to a lesser extent than does the full-length protein (Palonen et al., 2004).

Naturally-occurring linker peptides in cellulase and hemicellulase enzymes, whether from bacterial or fungal sources, vary from 6-59 amino acids in length. These peptides are similar in their chemical properties and amino acid composition, if not their specific sequences, with the amino acids serine, threonine, and proline accounting for more than 50% of the amino acids in the linker peptide (reviewed in Gilkes et al. (1991). Serine and threonine residues may be modified with O-linked glycans, which, in fungi, are predominantly mannose (Fägerstam et al., 1984). Linkers also contain several charged residues of a common type, either all negative (such as Glu or Asp) or all positive (such as Lys, Arg or His).

Linker peptides maintain the spatial orientation of the catalytic domain relative to the CBM. Shen et al. (1991) demonstrated that deleting the linker peptide altered the relative orientation of the catalytic domain and CBM of *Cellulomonas fimi* CenA without altering the tertiary structure of either domain. Effects of the linker peptide on the global conformation of Cel45A from *Humicola insolens* have been studied by small angle x-ray scattering (SAXS) (Receveur et al., 2002) and dynamic light scattering (Boisset et al., 1995). These investigators concluded that the linker peptide is an extended yet flexible structure and that glycosylation of the linker peptide favours more extended conformations, altering the relative positioning of the catalytic domain and CBM. Similarly, analysis of Cex from *Cellulomonas fimi* by NMR indicated that glycosylation of the linker peptide sterically constrains its flexibility, resulting in a more extended conformation and increasing the mean separation of the catalytic domain and CBM (Shen et al., 1991). A *Humicola* Cel6A-Cel6B chimeric double cellulase analyzed by SAXS showed that the linker peptide was flexible, adopting a compact rather than an extended conformation (von Ossowski et al., 2005). The authors suggested that the compact structure may be related to low levels of O-linked glycosylation in the Cel6A and Cel6B linker peptides.

Linker peptides modulate the binding of glycosyl hydrolases to cellulose and their enzymatic activity. Removing linker peptide from the *Cellulomonas fimi* CenA cellulase not only altered its structure, but reduced its catalytic efficiency. Although adsorption to cellulose was not affected, removal of the linker peptide impaired desorption of the bound enzyme from the crystalline cellulose substrate Avicel. Partial deletion of the linker peptide from *Trichoderma* Cel7A reportedly reduces its binding capacity on crystalline cellulose, while effects on catalytic activity were negligible (Srisodsuk et al., 1993). Complete removal of the Cel7A linker peptide reduced cellulolytic activity by 50%. These studies utilized Avicel and bacterial cellulose, essentially pure cellulosic substrates. However, these substrates do not fully represent the heterogeneity of lignocelluloses generated by commercial pretreatment processes, in particular because they do not contain lignin.

Variants of *Trichoderma reesei* Cel7A and Cel6A to improve thermostability have been reported (U.S. Pat. No. 7,375,197; WO 2005/028636; U. S. Publication No. 2007/0173431; Publication No. 2008/167214; WO 2006/074005; Publication No. 2006/0205042; U.S. Pat. No. 7,348,168; WO 2008/025164). In particular, substitution of the serine at position 413 in *T. reesei* Cel6A with a proline, or substitution of the amino acid at the equivalent to position 413 with a proline in other Family 6 cellulases confers increased thermostability (WO 2008/025164). Mutations at the equivalent of positions 103, 134, 136, 186, 365 and 410 within the catalytic domain of *T. reesei* Cel6A and other Family 6 cellulases have been shown to lead to reduce inhibition by glucose (U. S. Publication No. 2009-0186381). Variants with resistance to proteases and to surfactants for detergent formulations have been created for textile applications (WO 99/01544; WO 94/07998; and U.S. Pat. No. 6,114,296).

In most instances, mutations are specifically directed to the catalytic domain of the enzyme. In some instances the carbohydrate binding module has been targeted. Only in a few instances has the linker peptide been identified as playing a critical role or as a target for modification. The linker peptide of the *Humicola* family 45 endoglucanase was modified to reduce proteolysis (WO 94/07998; U.S. Pat. No. 6,114,296) and the linker peptide of the *Trichoderma* Cel7A was modified to promote thermostability (U.S. Pat. No. 7,375,197). Otherwise, the linker peptide region is typically ignored as a specific target for enzyme improvement.

The negative effects of lignin on cellulase enzyme systems are well documented. Removal of lignin from hardwood (aspen) was shown to increase sugar yield by enzymatic hydrolysis (Kong et al., 1992). Similarly, removal of lignin from softwood (Douglas fir) was shown to improve enzymatic hydrolysis of the cellulose, an effect attributed to improved accessibility of the enzymes to the cellulose (Mooney et al., 1998). Other groups have demonstrated that cellulases purified from *Trichoderma reesei* bind to isolated lignin (Chernoglazov et al., 1988) and have speculated on the role of the different binding domains in the enzyme-lignin interaction (Palonen et al., 2004). Binding to lignin and inactivation of *Trichoderma reesei* cellulases has been observed when lignin is added back to a pure cellulose system (Escoffier et al., 1991). Only in one instance was lignin reported to not have any significant effect on cellulases (Meunier-Goddik and Penner, 1999). Other reports suggest that some hemicellulases may be resistant to, and even activated by, lignin and lignin breakdown products (Kaya et al., 2000). Thus, it is generally recognized that lignin is a serious limitation to enzymatic hydrolysis of cellulose.

The development of lignin resistant cellulases represents a large hurdle in the commercialization of cellulose conversion to soluble sugars including glucose for the production of ethanol and other products. However, the lignin resistant enzymes must preserve their cellulose binding affinity and native cellulolytic activity. A variety of methods have been suggested to reduce the negative impact of lignin on the cellulase system. Non-specific binding proteins (e.g. bovine serum albumin; BSA) have been shown to block interactions between cellulases and lignin surfaces (Yang and Wyman, 2006; U.S. Publication No. 2004/0185542A1; U.S. Publication No. 2006/088922A1; WO2005/024037A2). Other chemical blocking agents and surfactants have been shown to have a similar effect (Tu et al., 2007; U.S. Pat. No. 7,354,743).

Recently, modified cellulases exhibiting reduced interactions with, or inactivation by, lignin have been reported. For example, WO2010/012102 reports that mutations at the equivalent of positions 129, 322, 363, 365 and 410 within the catalytic domain of *T. reesei* Cel6A (TrCel6A) and other Family 6 cellulases results in increased hydrolytic activity in the presence of lignin. Similarly, WO2009/149202 discloses cellulase variants exhibiting reduced affinity to lignin or ethanol or improved thermostability resulting from mutations at the equivalents of positions 63, 77, 129, 147, 153, 161, 194, 197, 203, 237, 247, 254, 281, 285, 289, 294, 327, 339, 344, 356, 378 and 382 in the linker peptide and catalytic domain of TrCel6A.

SUMMARY OF THE INVENTION

The present invention relates to modified cellulase enzymes. More specifically, the invention relates to modified cellulase enzymes with modified linker peptides that confer improved cellulose hydrolysing activity in the presence of lignin and/or reduced lignin binding to the modified cellulase enzymes. The present invention also relates to genetic constructs comprising nucleic acid sequences encoding for modified cellulase enzymes, methods for the production of the modified cellulase enzymes from host strains and a process for hydrolysing cellulose in the presence of lignin with the modified cellulase enzymes.

It is an object of the present invention to provide lignin-resistant cellulase enzymes. The lignin-resistant cellulase enzymes of the invention comprise linker peptides that confer decreased inactivation by lignin to the modified cellulase enzyme and thus increased cellulose hydrolyzing activity in the presence of lignin. In particular, the present invention relates to modified cellulases comprising a modified linker peptide, operably linked to a cellulase catalytic domain and a carbohydrate binding module, which modified linker peptide being from about 6 to about 60 amino acids in length, of which at least about 50% are either proline, serine or threonine, and comprising one or more amino acid substitutions, insertions, or deletions that result in (a) a decrease in the calculated isoelectric point of the linker peptide and/or (b) an increase in the ratio of threonine:serine in the linker peptide relative to a parental linker peptide from which said modified linker peptide is derived. The amino acid substitutions, insertions, or deletions in the linker peptide may result in at least a 0.2 unit decrease in the calculated isoelectric point of the linker peptide and/or at least about a 10% increase in the ratio of threonine:serine in the linker peptide A decrease in the calculated isoelectric point of the modified linker peptide may be achieved by one or more of the following modifications to the linker peptide: (a) replacement of one or more neutral or basic amino acids by acidic amino acids; (b) replacement of one or more basic amino acids by neutral amino acids; (c) insertion of one or more acidic amino acids; and (d) deletion of one or more basic amino acids. An increase in the threonine:serine ratio may be achieved by one or more of the following modifications to the linker peptide: (a) replacement of one or more non-threonine amino acids by threonine; (b) replacement of one or more serines by threonine; (c) insertion of one or more threonine residues; (d) deletion of one or more serine residues; and (e) replacement of one or more serines by non-threonine amino acid.

The modified linker peptide confers to the modified cellulase an increase in cellulose-hydrolyzing activity and/or a decrease in lignin binding relative to a parental cellulase comprising a parental linker operably linking between the same cellulase catalytic domain and same carbohydrate binding module as is present in the modified cellulase enzyme. The modified linker peptide may confer at least about a 10% increase in cellulose-hydrolyzing activity in the presence of lignin and/or at least about a 20% decrease in lignin binding relative to a parental cellulase. This reduced lignin binding and/or heightened cellulase activity in the presence of lignin has potential value in industries for the production of fermentable sugars, alcohols or sugar alcohols from lignocellulosic substrates, such as the production of ethanol from cellulose.

The cellulase catalytic domain may be any polypeptide that exhibits cellulose hydrolysing activity. In one embodiment of the modified cellulase enzyme of the present invention, the cellulase catalytic domain is a cellulase member of Glycosyl Hydrolase Family 5, 6, 7, 45, or 61. For example, the cellulase catalytic domain may be amino acids 83-447 of *Trichoderma reesei* Cel6A (SEQ ID No: 1), amino acids 1-437 of *Trichoderma reesei* Cel7A (SEQ ID NO: 3), amino acids 1 to 375 of *Trichoderma reesei* Cel7B (SEQ ID NO: 4), amino acids 71 to 397 of *Trichoderma reesei* Cel5A (SEQ ID NO: 2), amino acids 1 to 165 of *Trichoderma reesei* Cel45A (SEQ ID NO: 5), or amino acids 1 to 235 of *Trichoderma reesei* Cel61A (SEQ ID NO: 6).

The cellulase catalytic domain may exhibit from about 60% amino acid sequence identity to amino acids 83-447 of *Trichoderma reesei* Cel6A (SEQ ID NO: 1) or to amino acids 1-437 of *Trichoderma reesei* Cel7A (SEQ ID NO: 3). The cellulase catalytic domain may be amino acids 83-447 *Trichoderma reesei* Cel6A (SEQ ID NO: 1) comprising one or more amino acid substitutions selected from the group consisting of: 103H, Y103K, Y103R, Y103A, Y103V, Y103L, Y103P, K129E, M134I, M134Q, M134T, M134V, M134Y, L136V, L1361, S186K, S186T, S186Y, Q204K, G213D, A322D, Q363E, G365D, G365E, G365Q, G365S, R410A, R410F, R410L, R410Q, R410S and S413P.

In another embodiment of the cellulase enzyme of the present invention, the carbohydrate binding module is a cellulose binding domain (CBD). For example, the carbohydrate binding module may be the CBD of *Trichoderma reesei* Cel6A (SEQ ID NO: 49), *Trichoderma reesei* Cel7A (SEQ ID NO: 50) *Trichoderma reesei* Cel7B (SEQ ID NO: 51) *Trichoderma reesei* Cel5A (SEQ ID NO: 48) *Trichoderma reesei* Cel61A (SEQ ID NO: 53), *Trichoderma reesei* Cel45A (SEQ ID NO: 52), *Trichoderma reesei* Cip1 (SEQ ID NO: 54), or *Trichoderma reesei* Swollenin (SEQ ID NO: 55). For example, the CBM may exhibit from about 50% amino acid sequence identity to amino acids 3-39 of *Trichoderma reesei* Cel6A (SEQ ID NO: 1) and may comprise a substitution of the serine at position 35 by an aromatic amino acid.

Any one or all of the modified linker peptide, cellulase catalytic domain or carbohydrate binding module may be derived from one or more fungal cellulases produced by such organisms including, but not limited to, *Trichoderma* ssp., *Aspergillus* ssp., *Hypocrea* ssp., *Humicola* ssp., *Neurospora* ssp., *Orpinomyces* ssp., *Gibberella* ssp., *Emericella* ssp., *Chaetomium* ssp., *Chrysosporium* ssp., *Myceliophthora* ssp., *Fusarium* ssp., *Penicillium* ssp., *Magnaporthe* ssp., *Phanerochaete* ssp, *Trametes* ssp, *Lentinula edodes, Gleophyllum trabeiu, Ophiostoma piliferum, Corprinus cinereus, Geomyces pannorum, Cryptococcus laurentii, Aureobasidium pullulans, Amorphotheca resinae, Leucosporidium scotti, Cunninghamella elegans, Thermomyces lanuginosa*, and *Sporotrichum thermophile.*

The present invention further relates to genetic constructs comprising DNA encoding the modified cellulase enzyme as described above and to genetically modified microbes comprising such genetic constructs for the expression and secretion of the modified cellulase. The genetically modified microbe is a bacterium, yeast or filamentous fungus, such as a species of *Streptomyces, Pichia, Hansenula, Saccharomyces, Aspergillus, Fusarium, Hypocrea, Neurospora, Trichoderma, Chrysosporium* or *Myceliophthora.*

The present invention also relates to a process for producing the modified cellulase enzyme, as described above, comprising the steps of growing a genetically modified microbe comprising a genetic construct encoding the modified cellulase enzyme under conditions that induce the expression and secretion of the modified cellulase enzyme and recovering the modified cellulase enzyme from the culture medium. Such process for producing the modified cellulase enzyme as described above may include a step of transforming a host cell with a genetic construct encoding the modified cellulase enzyme.

The present invention also relates to a process for hydrolyzing a cellulose substrate comprising contacting said substrate with the modified cellulase enzyme as described above in the presence of lignin. For example, the modified cellulase enzyme of the present invention may be used for the industrial processing of lignocellulose for the production of fermentable sugars, sugar alcohols or fuel alcohol.

The present invention relates to a modified cellulase enzyme comprising a cellulase catalytic domain, CBM and a modified linker peptide selected from the group consisting of:

linkTrCel6A-G72D (SEQ ID NO: 29);
linkTrCel6A-S45N (SEQ ID NO: 27);
linkTrCel6A-T76A (SEQ ID NO: 30);
linkTrCel6A-G40D (SEQ ID NO: 26);
linkTrCel6A-V81D (SEQ ID NO: 31);
linkTrCel6A-R63L (SEQ ID NO: 28);
linkTrCel6A-P71T (SEQ ID NO: 32);
linkTrCel6A-G40D-S45N-R63L-P71T-G72D-T76A-V81D (SEQ ID NO: 34);
linkTrCel6A-Δ1 (SEQ ID NO: 35)
linkTrCel6A-Δ2 (SEQ ID NO: 36);
linkTrCel6A$^{R \rightarrow E}$ (SEQ ID NO: 33)
linkTrCel6A$^{S \rightarrow T}$ (SEQ ID NO: 37)
linkTrCel6A$^{R \rightarrow E/S \rightarrow T}$ (SEQ ID NO: 38)
linkTrCel7A$^{R \rightarrow E}$ (SEQ ID NO: 40)
linkTrCel7A$^{R \rightarrow E/S \rightarrow T}$ (SEQ ID NO: 41)

BRIEF DESCRIPTION OF THE DRAWINGS

FIG. 7 is an illustration of the amino acid substitutions introduced into the TrCel6A linker peptide sequence to produce the Novel TrCel6A Linker Variants. The figure shows an alignment of the N-terminal amino acids of several modified cellulase with amino acids 1-99 of TrCel6A ("Wt") as provided in SEQ ID NO: 1. Aggregate: TrCel6A-S35F-G40D-S45N-R63L-P71T-G72D-T76A-V81D-S413P (SEQ ID NO: 18), R→E: TrCel6A$^{R \rightarrow E}$ (SEQ ID NO: 21), R→E/S→T: TrCel6A$^{R \rightarrow E/S \rightarrow T}$ (SEQ ID NO: 23), 41: TrCel6A$^{\Delta 1}$ (SEQ ID NO: 19) and 42: TrCel6A$^{\Delta 2}$ (SEQ ID NO: 20).

DETAILED DESCRIPTION OF THE INVENTION

Figure 1A:
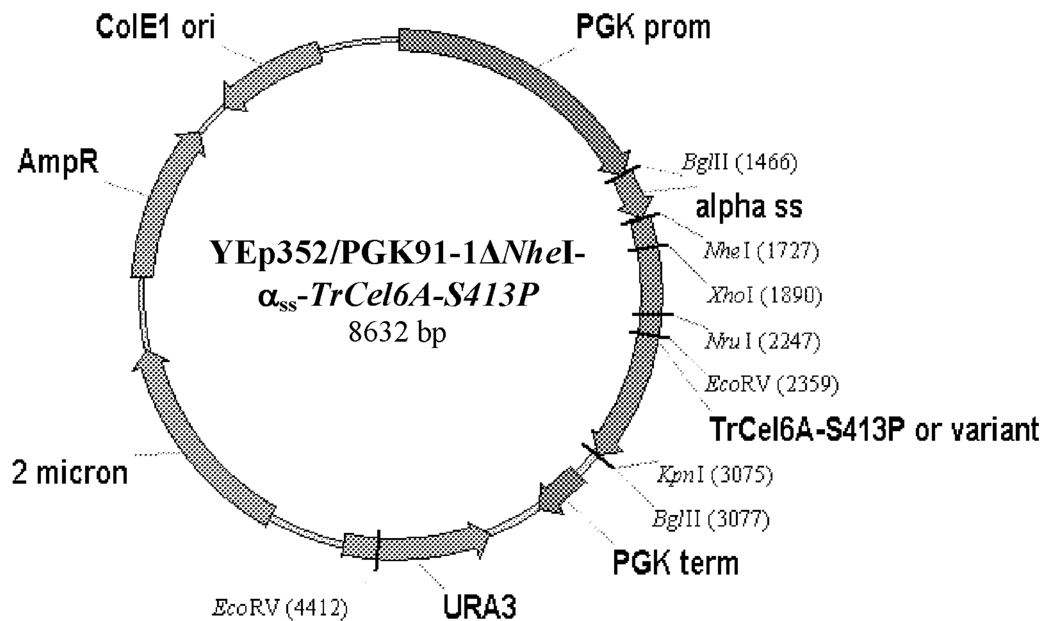
FIG. 1 depicts A. plasmid vector YEp352/PGK91-1ΔNheI-alpha$_{ss}$-TrCel6A-5413P directing the expression and secretion of parental and modified *Trichoderma* Cel6A (TrCel6A) cellulases from recombinant *Saccharomyces cerevisiae* and B. transformation vector pC/XCel6A-pyr4-TV directing the expression of secretion of parental and modified *Trichoderma* Cel6A (TrCel6A) cellulases from recombinant *Trichoderma reesei.*

The present invention relates to modified cellulase enzymes. More specifically, the invention relates to modified cellulases with modified linker peptides that confer resistance to lignin binding to the modified cellulase enzyme. The present invention also relates to genetic constructs comprising nucleic acid sequences encoding modified cellulase enzymes, methods for the production of the modified cellulase enzymes from host strains and a process for hydrolysing cellulose in the presence of lignin with the modified cellulase enzymes.

The following description is of a preferred embodiment by way of example only and without limitation to the combination of features necessary for carrying the invention into effect. The headings provided are not meant to be limiting of the various embodiments of the invention. Terms such as "comprises", "comprising", "comprise", "includes", "including" and "include" are not meant to be limiting. In addition, the use of the singular includes the plural, and "or" means "and/or" unless otherwise stated. Unless otherwise defined herein, all technical and scientific terms used herein have the same meaning as commonly understood by one of ordinary skill in the art.

Modified Cellulase Enzymes

A "cellulase enzyme" is defined as any enzyme that is capable of cleaving the beta-1,4 glycosidic linkages in a cellulose polymer. A cellulase enzyme can be an endoglucanase (EC 3.2.1.4), which cleaves internal beta-1,4 glycosidic linkages in the cellulose polymer to decrease the degree of polymerization of the polymer and/or release oligosaccharides. A cellulase enzyme can also be an exoglucanase or cellobiohydrolase (EC 3.2.1.91), which releases small oligosaccharides, primarily cellobiose, from the ends of the cellulose polymer. The definition of "cellulase enzyme" also includes proteins that interact with cellulose to facilitate its hydrolysis including, but not limited to, swollenins and expansins.

A cellulose polymer can be natural cellulose, such as that produced by plants or algae or other organisms and may be pure or be one of several constituents in plant biomass, which also comprises lignin and hemicellulse. The cellulose polylmer may also be a cellulose derivative, such as carboxymethyl cellulose or hydroxyethyl cellulose.

A cellulase enzyme, as used herein, comprises a cellulase catalytic domain and a carbohydrate binding module (CBM), and a linker peptide positioned between the catalytic domain and the CBM. The cellulase catalytic domain, CBM and linker peptide may be homologous with respect to each other—i.e., belonging to the same cellulase as isolated in nature—or heterologous with respect to at least one other domain—i.e., being isolated from two or more different naturally occurring cellulases from the same, or different, source organism(s). The amino acid sequences of the cellulase catalytic domain, CBM and linker peptide may be "native" or "wild type"—i.e., as found in unmodified cellulases produced in nature—or they may be derived from native or wild-type cellulases by modification of their amino acid sequences.

A cellulase enzyme may comprise additional functional domains, e.g., additional cellulase or hemicellulase catalytic domains, CBMs, cohesions, dockerins, or fibronectin-like (Fn3) domains and still be considered a cellulase enzyme.

Examples of cellulase enzymes from which the cellulase catalytic domain, CBM and linker peptide may be isolated or derived include cellulase enzymes from various microorganims such as *Trichoderma* ssp., *Aspergillus* ssp., *Hypocrea* ssp., *Humicola* ssp., *Neurospora* ssp., *Orpinomyces* ssp., *Gibberella* ssp., *Emericella* ssp., *Chaetomium* ssp., *Chrysosporium* ssp., *Myceliophthora* ssp., *Fusarium* ssp., *Penicillium* ssp., *Magnaporthe* ssp., *Phanerochaete* ssp, *Trametes* ssp, *Lentinula edodes, Gleophyllum trabeiu, Ophiostoma piliferum, Corprinus cinereus, Geomyces pannorum, Cryptococcus laurentii, Aureobasidium pullulans, Amorphotheca resinae, Leucosporidium scotti, Cunninghamella elegans, Thermomyces lanuginosa, Sporotrichum thermophile*, or *Thermobifida fusca*. The practice of the invention is not limited by the cellulase from which the cellulase catalytic domain, CBM and linker peptide may be derived.

A "modified cellulase enzyme" as used herein, is a cellulase enzyme comprising the same cellulase catalytic domain and CBM as a parental cellulase enzyme, and a "modified linker peptide" that has been modified by amino acid deletion, insertion, or substitution to (a) decrease the calculated isoelectric point of the linker peptide, and/or (b) increase the threonine:serine ratio of the linker peptide relative to a parental linker peptide.

The isoelectric point of a protein or peptide is the pH at which the peptide has a net zero charge, i.e., the pH at which the negative and positively charged functional groups in the protein or peptide are electrostatically balanced. Peptides and proteins with a high pI value contain more basic amino acids such as lysine, arginine and histidine, whereas peptides and proteins with low pI values have more glutamic and aspartic acid residues. The pI of a peptide, such as a linker, can be easily calculated by one of skill in the art using any one of many programs freely available on the world wide web, such as the ProtParam tool available at ExPASy Proteomics Server (see URL au.expasy.org/tools/protparam.html).

As used herein, a "parental cellulase enzyme" is a cellulase enzyme comprising a parental linker peptide, cellulase catalytic domain, a CBM and any additional functional domains that may be present in the modified cellulase enzyme. The cellulase catalytic domain, CBM and any additional functional domain are identical to the corresponding catalytic domains and CBM in the modified cellulase enzyme. Furthermore, the parental linker peptide is identical to the modified linker peptide of the modified cellulase enzyme except that it has not been modified by amino acid insertion, deletion or substitution to (a) decrease the isoelectric point of the linker peptide, and/or (b) increase the threonine:serine ratio of the linker peptide. One of skill in the art recognizes that the cellulase catalytic domain, CBM and parental linker peptide may contain amino acid substitutions, insertions or deletions relative to a naturally-occurring cellulase catalytic domain, CBM, or linker peptide provided that these amino acid substitutions are also present in the modified cellulase enzyme and, with respect to the parental linker peptide, such amino acid substitutions, insertions or deletions do not (a) decrease the isoelectric point of the linker peptide, and/or (b) increase the threonine:serine ratio of the linker peptide relative to the naturally-occurring linker peptide.

A cellulase catalytic domain is typically, though not necessarily, the larger of the two domains and is the domain which performs the hydrolysis reaction. A cellulase catalytic domain may be a member of one of many Glycosyl Hydrolase (GH) families, for example, GH Family 5, 6, 7, 45, and 61. Members of a given GH family share a common three-dimensional structure, regions of conserved amino acid homology and common catalytic mechanisms (Davies and Henrissat, 1995 and references therein). Examples of cellulase catalytic domains useful for the practice of this invention include those in GH Families 5, 6, 7, 45 and 61. For example, the cellulase catalytic domain may be acids 83-447 of *Trichoderma reesei* Cel6A (SEQ ID No: 1), amino acids 1-437 of *Trichoderma reesei* Cel7A (SEQ ID NO: 3), amino acids 1 to 375 of *Trichoderma reesei* Cel7B (SEQ ID NO: 4), amino acids 71 to 397 of *Trichoderma reesei* Cel5A (SEQ ID NO: 2), amino acids 1 to 165 of *Trichoderma reesei* Cel45A (SEQ ID NO: 5), or amino acids 1 to 235 of *Trichoderma reesei* Cel61A (SEQ ID NO: 6).

One of skill in the art recognizes that the amino acid sequence of a given cellulase catalytic domain may be modified by the addition, deletion or substitution of one or more amino acids and still be considered a cellulase catalytic domain. For the purpose of the invention described herein, a protein is a cellulase catalytic domain if it shows at least from about 60% identity in amino acid sequence to any other cellulase catalytic domain identified at the time of filing as belonging to the same GH family. For example, the protein may show from about 60%, 65%, 70%, 75%, 80%, 85%, 90%, or 95% amino acid identity to any other cellulase catalytic domain in the same GH family or any percent identity therebetween. The cellulase catalytic domain may exhibit from about 60% amino acid sequence identity to amino acids 83-447 of *Trichoderma reesei* Cel6A (SEQ ID NO: 1) or to amino acids 1-437 of *Trichoderma reesei* Cel7A (SEQ ID No: 3). The cellulase catalytic domain may be amino acids 83-447 *Trichoderma reesei* Cel6A (SEQ ID NO: 1) comprising one or more amino acid substitutions selected from the group consisting of: Y103H, Y103K, Y103R, Y103A, Y103V, Y103L, Y103P, K129E L136V, L136I, S186K, S186T, S186Y, Q204K, G231D, A322D, Q363E, G365D, G365E, G365Q, G365S, R410A, R410F, R410L, R410Q, R410S.

Sequence identity can be readily determined by alignment of the amino acids of the two sequences, either using manual alignment, or any sequence alignment algorithm as known to one of skill in the art, for example but not limited to, BLAST algorithm (BLAST and BLAST 2.0; Altschul et al., Nuc. Acids Res. 25:3389-3402, 1997; and Altschul et al., J. Mol. Biol. 215:403-410, 1990), the algorithm disclosed by Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)). In the case of conducting BLAST alignments and sequence identity determinations for cellulase enzymes, only the amino acid sequences comprising the catalytic domains are considered. Tables 1A, 1B, 1C, 1D, 1E, 1F and 1G show the percent identity of amino acid sequences results from BLAST alignment cellulase catalytic domains of GH Family 7, 6, 5, 61, and 45 to the *T. reesei* cellulases Cel7A, Cel6A, Cel7B, Cel5A, Cel61A, Cip1 and Swollenin, respectively. All of the cellulase catalytic domains share at least 40%, and many show at least 60%, identity with the entire catalytic domain or highly conserved regions in corresponding GH Family cellulase from *Trichoderma reesei*.

TABLE 1A

Sequence Identity of Family 7 Cellulase Catalytic Domains to *Trichoderma reesei* Cel7A

| Organism | Protein | GenPept Accession | % Identity with *T. reesei* Cel7A (1-437)* |
|---|---|---|---|
| *Hypocrea koningii* G-39 | Cellobiohydrolase (Cbh1) - Cel7A | CAA49596 | 100.0 |
| *Trichoderma viride* AS 3.3711 | Cellobiohydrolase I | AAQ76092 | 99.3 |
| *Trichoderma viride* | 1,4-beta-D-glucan Cellobiohydrolase | CAA37878 | 96.1 |
| *Trichoderma harzianum* | Cellobiohydrolase | AAF36391 | 81.9 |
| *Aspergillus niger* CBS 513.88 | 1,4-beta-D-glucan cellobiohydrolase A precursor | AAF04491 | 65.5 |
| *Talaromyces emersonii* | Cellobiohydrolase 1-Cel7A | AAL33603 | 65.0 |
| *Thermoascus aurantiacus* var. *levisporus* | Cellobiohydrolase Precursor | AAW27920 | 64.6 |
| *Aspergillus oryzae* KBN616 | Cellobiohydrolase C | BAC07255 | 63.8 |
| *Thermoascus aurantiacus* | Cellobiohydrolase Precursor | AAL16941 | 63.2 |
| *Penicillium occitanis* | Cellobiohydrolase I | AAT99321 | 63.2 |
| *Penicillium funiculosum* | xylanase/cellobiohydrolase | CAC85737 | 63.0 |
| *Cryphonectria parasitica* EP155 | Cellobiohydrolase | AAB00479 | 62.6 |
| *Acremonium thermophilum* ALKO4245 | Cellulose 1,4-beta-cellobiosidase | CAM98445 | 62.5 |
| *Aspergillus niger* CBS 513.88 | 1,4-beta-D-glucan cellobiohydrolase B precursor | AAF04492 | 61.8 |
| *Neurospora crassa* OR74A | Exoglucanase 1 Precursor | EAA33262 | 61.0 |
| *Penicillium chrysogenum* FS010 | Exo-cellobiohydrolase | AAV65115 | 60.8 |
| *Aspergillus oryzae* RIB 40 | Cellobiohydrolase D | BAE61042 | 60.4 |

*For *T. reesei* CBH1, ammo acid 1 is the first ammo acid of the secreted enzyme, such that the first eight amino acids are QSACTLQS . . .

TABLE 1B

Sequence Identity of Family 6 Cellulase Catalytic Domains to *Trichoderma reesei* Cel6A

| Organism | Protein | GenPept Accession | % Identity with *T. reesei* Cel6A (aa 83-447) |
|---|---|---|---|
| *Hypocrea koningii* | cellobiohydrolase II (Cbh2) | AAK01367.1 | 98.9 |
| *Trichoderma viride* CICC 13038 | cellobiohydrolase II (CbhII; Cbh2) | AAQ76094.1 | 98.9 |
| *Hypocrea koningii* 3.2774 | cellobiohydrolase II (Cbh2; CbhII) | ABF56208.1 | 98.1 |
| *Hypocrea koningii* AS3.2774 | cbh2 | ABG48766.1 | 97.8 |
| *Trichoderma parceramosum* | cellobiohydrolase II (CbhII) | AAU05379.2 | 97.8 |
| *Aspergillus nidulans* FGSC A4 | cellobiohydrolase (AN5282.2) | ABF50873.1 | 72.4 |
| *Aspergillus niger* CBS 513.88 | An12g02220 | CAK41068.1 | 72.4 |
| *Aspergillus oryzae* RIB 40 | AO090038000439 | BAE64227.1 | 67.8 |
| *Aspergillus niger* CBS 513.88 | An08g01760 | CAK39856.1 | 67.7 |
| *Acremonium cellulolyticus* Y-94 | cellobiohydrolase II (Acc2) | AAE50824 | 67.3 |
| *Talaromyces emersonii* | cellobiohydrolase II (CbhII) | AAL78165.2 | 66.8 |
| *Gibberella zeae* K59 | Cel6 - Cel6 | AAQ72468.1 | 66.1 |
| *Fusarium oxysporum* | endoglucanase B | AAA65585.1 | 66.1 |

TABLE 1B-continued

| Organism | Protein | GenPept Accession | % Identity with *T. reesei* Cel6A (aa 83-447) |
|---|---|---|---|
| *Neurospora crassa* OR74A | NCU09680.1 (64C2.180) | CAD70733.1 | 65.9 |
| *Aspergillus nidulans* FGSC A4 | AN1273.2 | EAA65866.1 | 65.5 |
| *Magnaporthe grisea* 70-15 | MG05520.4 | XP_360146.1 | 65.4 |
| *Chaetomium thermophilum* CT2 | cellobiohydrolase (Cbh2) | AAW64927.1 | 65.0 |
| *Humicola insolens* | avicelase 2 (Avi2) | BAB39154.1 | 63.7 |
| *Cochliobolus heterostrophus* C4 | cellobiohydrolase II (CEL7) | AAM76664.1 | 59.6 |
| *Agaricus bisporus* D649 | cellobiohydrolase II (Cel3; Cel3A) | AAA50607.1 | 57.7 |
| *Polyporus arcularius* 69B-8 | cellobiohydrolase II (Cel2) | BAF80327.1 | 57.1 |
| *Lentinula edodes* Stamets CS-2 | cellulase - Cel6B | AAK95564.1 | 56.3 |
| *Lentinula edodes* L54 | cellobiohydrolase (CbhII-1) | AAK28357.1 | 56.0 |
| *Malbranchea cinnamomea* | unnamed protein product | CAH05679.1 | 54.9 |
| *Phanerochaete chrysosporium* | cellobiohydrolase II | AAB32942.1 | 54.9 |
| *Volvariella volvacea* | cellobiohydrolase II-I (CbhII-I) | AAT64008.1 | 53.8 |
| *Chrysosporium lucknowense* | cellobiohydrolase (EG6; CBHII) - Cel6A | AAQ38151.1 | 49.5 |
| *Pleurotus sajor-caju* | cellobiohydrolase II | AAL15037.1 | 47.2 |
| *Trametes versicolor* | ORF | AAF35251.1 | 47.0 |
| *Neurospora crassa* OR74A | NCU03996.1 | XP_323315.1 | 46.8 |
| *Magnaporthe grisea* 70-15 | MG04499.4 | XP_362054.1 | 45.1 |

Sequence Identity of Family 6 Cellulase Catalytic Domains to *Trichoderma reesei* Cel6A

*For *T. reesei* CBH1, amino acid 1 is the first amino acid of the secreted enzyme, such that the first eight amino acids are QAACSSVWG.

TABLE 1C

Sequence Identity of Family 7 Cellulase Catalytic Domains to *Trichoderma reesei* Cel7B

| Organism | Protein | GenPept Accession | % Identity with *T. reesei* Cel7B (aa 1-374)* |
|---|---|---|---|
| *Trichoderma viride* AS 3.3711 | Endoglucanase I | AAQ21382 | 99.5 |
| *Trichoderma longibrachiatum* | Endo-1,4-glucanase I | CAA43059 | 95.5 |
| *Hypocrea pseudokoningii* | Endoglucanase I | ABM90986 | 95.2 |
| *Penicillium decumbens* 114-2 | Endoglucanase I | ABY56790 | 62.5 |
| *Aspergillus oryzae* RIB 40 | Endo-1,4-glucanase | BAE66197 | 49.1 |
| *Aspergillus oryzae* KBN616 | Endo-1,4-glucanase (CelB) | BAA22589 | 48.9 |
| *Neurospora crassa* OR74A | Endoglucanase EG-1 precursor | EAA27195 | 48.7 |
| *Aspergillus nidulans* FGSC A4 | Endo-β-1,4-glucanase | EAA63386 | 47.9 |
| *Neurospora crassa* OR74A | Hypothetical Protein | XP_324211 | 41.7 |

*For *T. reesei* EG1, amino acid 1 is the first amino acid of the secreted enzyme, such that the first eight amino acids are QQPGTSTP.

TABLE 1D

Sequence Identity of Family 5 Cellulase Catalytic Domains to *Trichoderma reesei* Cel5A

| Organism | Protein | GenPept Accession | % Identity with *T. reesei* Cel5A (aa 202-222)* |
|---|---|---|---|
| *Trichoderma viride* | Endoglucanase | ABQ95572 | 100 |
| *Trichoderma viride* AS 3.3711 | Endoglucanase III | AAQ21383 | 100 |
| *Trichoderma viride* MC300-1 | Endo-1,4-glucanase II | BAA36216 | 100 |
| *Trichoderma* sp. C-4 | Endo-1,4-glucanase | AAR29981 | 92 |
| *Phanerochaete chrysosporium* | Endoglucanase - Cel5A | AAU12275 | 72 |
| *Macrophomina phaseolina* | Endo-1,4-glucanase | AAB03889 | 64 |
| *Cryptococcus* sp. S-2 | Carboxymethylcellulase | ABP02069 | 56 |
| *Cryptococcus flavus* | Carboxymethylcellulase | AAC60541 | 50 |
| *Irpex lacteus* MC-2 | Endoglucanase | BAD67544 | 48 |
| *Hypocrea jecorina* QM6a | Cel5B | AAP57754 | 48 |
| *Macrophomina phaseolina* | Endo-1,4-glucanase | AAB51451 | 44 |
| *Thermoascus aurantiacus* IFO 9748 | EGI Precursor | AAL16412 | 44 |
| *Trametes hirsuta* | Endoglucanase | BAD01163 | 44 |
| *Aspergillis oryzae* | Endo-1,4-glucanase (CelE) | BAD72778 | 44 |
| *Talaromyces emersonii* | Endo-1,4-glucanase | AAL33630 | 40 |

TABLE 1D-continued

Sequence Identity of Family 5 Cellulase Catalytic Domains to *Trichoderma reesei* Cel5A

| Organism | Protein | GenPept Accession | % Identity with *T. reesei* Cel5A (aa 202-222)* |
|---|---|---|---|
| *Humicola grisea* var. *thermoidea* IFO9854 | Cellulase (Endo-1,4-glucanase 3) | BAA12676 | 40 |
| *Humicola insolens* | Endo-1,4-glucanase IV | CAA53631 | 40 |
| *Aspergillis kawachi* | Endoglucanase C (Cel5B) | BAB62319 | 40 |
| *Aspergillis nidulans* | Endo-β-1-4-glucanase | ABF50848 | 40 |

*For *T. reesei* EG2, amino acid 1 is the first amino acid of the secreted enzyme, such that the first eight amino acids are QQTVWGQC.

TABLE 1E

Sequence Identity of Family 61 Cellulase Catalytic Domains to *Trichoderma reesei* Cel61A

| Organism | Protein | GenPept Accession | % Identity with *T. reesei* Cel61A (aa 144-163) |
|---|---|---|---|
| *Neurospora crassa* | Endoglucanase IV (NCU07760.1) | EAA29018 | 80 |
| *Thielavia terrestris* | Cel61C | ACE10232 | 75 |
| *Gibberella zeae* | Cel61E | XP_383871 | 75 |
| *Thielavia terrestris* | Cel61D | ACE10233 | 70 |
| *Trichoderma reesei* | Cel61B | AAP57753 | 65 |
| *Phanerochaete chrysosporium* BKM-F-1767 | Cel61A | AAM22493 | 65 |
| *Thielavia terrestris* | Cel61B | ACE10231 | 60 |
| *Aspergillus kawachii* | Cel61A | BAB62318 | 52 |
| *Aspergillus nidulans* FGSC A4 | Endo-β1,4-glucanase (AN1602.2) | EAA64722 | 52 |
| *Thielavia terrestris* | Cel61E | ACE10234 | 50 |
| *Gibberella zeae* | Sequence 122805 from U.S. Pat. No. 7,214,786 | ABT35335 | 45 |
| *Thielavia terrestris* | Cel61G | ACE10235 | 40 |

TABLE 1F

Sequence Identity of Cip1 Enzymes to *Trichoderma reesei* Cip1

| Organism | Protein | GenPept Accession | % Identity with *T. reesei* Cip1 (aa 1-212)* |
|---|---|---|---|
| *Pyrenophora tritici-repentis* Pt-1C-BFP | Cip1 | XP_001937765 | 56.9 |
| *Streptomyces coelicolor* A3(2) | Putative Secreted Hydrolase | CAA18323 | 39.6 |
| *Herpetosiphon aurantiacus* ATCC 23779 | Cellulose-Binding Family II Protein | YP_001545140 | 38.8 |

*For *T. reesei* Cip1, amino acid 1 is the first amino acid of the secreted enzyme, such that the first eight amino acids are QISDDFES . . .

TABLE 1G

Sequence Identity of Swollenin Enzymes to *Trichoderma reesei* Swollenin

| Organism | Protein | GenPept Accession | % Identity with *T. reesei* Swollenin (aa 92-475)* |
|---|---|---|---|
| *Hypocrea pseudokoningii* | Swollenin | ABV57767 | 95.8 |
| *Trichoderma asperellum* | Swollenin | ACB05430 | 92.4 |
| *Neosartorya fischeri* NRRL 181 | Fungal Cellulose Binding Domain Protein | XP_001257521 | 74.0 |
| *Aspergillus fumigatus* Af293 | Swollenin | XP_747748 | 70.2 |

*For *T. reesei* Swollenin, amino acid 1 is the first amino acid of the secreted enzyme, such that the first eight amino acids are QQNCAALF.

The cellulase catalytic domain may be acids 83-447 of *Trichoderma reesei* Cel6A (SEQ ID No: 1), amino acids 1-437 of *Trichoderma reesei* Cel7A (SEQ ID NO: 3), amino acids 1 to 375 of *Trichoderma reesei* Cel7B (SEQ ID NO: 4), amino acids 71 to 397 of *Trichoderma reesei* Cel5A (SEQ ID NO: 2), amino acids 1 to 165 of *Trichoderma reesei* Cel45A (SEQ ID NO: 5), or amino acids 1 to 235 of *Trichoderma reesei* Cel61A (SEQ ID NO: 6), amino acids 1 to 219 of *Trichoderma reesei* Cip1 (SEQ ID No: 7), or amino acids 79 to 475 of *Trichoderma reesei* Swollenin (SEQ ID No: 8).

The cellulase catalytic domain may exhibit from about 60% amino acid sequence identity to amino acids 83-447 of *Trichoderma reesei* Cel6A (SEQ ID NO: 1) or to amino acids 1-436 of *Trichoderma reesei* Cel7A (SEQ ID No: 3). The cellulase catalytic domain may be amino acids 83-447 *Trichoderma reesei* Cel6A (SEQ ID NO: 1) comprising one or more amino acid substitutions selected from the group consisting of: 103H, Y103K, Y103R, Y103A, Y103V, Y103L, Y103P, K129E, M1341, M134Q, M134T, M134V, M134Y, L136V, L1361, S186K, S186T, S186Y, Q204K, G213D, A322D, Q363E, G365D, G365E, G365Q, G365S, R410A, R410F, R410L, R410Q, R410S and S413P.

Carbohydrate binding modules or CBMs are non-catalytic domains in glycoside hydrolases and other proteins that recognize and bind to polysaccharides. CBMs are often found in fungal and bacterial proteins that contain a glycoside hydrolase domain that degrades insoluble polysaccharides. However, CBMs have also been identified in proteins that do not contain a glycosyl hydrolase domain but are involved in the degradation of insoluble polysaccharides such as cellulose. These include but are not limited to Cip1 (Foreman et al., 2003) and Swollenin (Saloheimo et al., 2002). CBMs are divided into families based on amino acid sequence similarity; there are currently 59 families of CBMs (see URL afmb.cnrs-mrs.fr/CAZY/index.html). Amongst these CBMs, different members have been shown to recognize crystalline cellulose, non-crystalline cellulose, chitin, beta-glucans, xylan, mannan, galactan and starch. CBMs are sometimes referred to by the term “cellulose-binding domain” or “CBD”.

In fungi, CBMs are homologous and members of CBM Family 1 (CBM1). The sequences of CBMs from *T. reesei* cellulases, hemicellulases and related proteins that may be incorporated into the modified cellulases of the present invention are shown in Table 2. Four cysteines are highly conserved and form two disulfide bridges. Three aromatic amino acids (tryptophan, tyrosine or phenylalanine) are also conserved and form a planar surface and interact directly with the glucose units of the cellulose polymer via van der Waals’ interactions.

A CBM is defined herein as any protein sequence that is classified as a carbohydrate-binding module according to the CAZy system (see URL afmb.cnrs-mrs.fr/CAZY/index.html for reference). For example, a CBM may be a Family 1 CBM according to the CAZy system. A Family 1 CBM may exhibit from about 50% amino acid sequence identity with amino acids 460-496 of *Trichoderma reesei* CBH2 (GenPept Accession No. AAA34210). For example, the CBM may show from about 50%, 60%, 70%, 80%, 90%, or 95% amino acid identity with amino acids 3-39 of *Trichoderma reesei* CBH2 (or TrCel6A as provided in SEQ ID NO: 1). One of skill in the art recognizes that the amino acid sequence of a given CBM may be modified by the addition, deletion or substitution of one or more amino acids and still be considered a CBM.

TABLE 2

Sequence alignment of Family 1 CBMs from *Trichoderma reesei* proteins

| Enzyme | Accession | CBM Sequence | % Identity with *T. reesei* Cel6A CBM (aa 3-39) |
|---|---|---|---|
| TrCel7A | CAH10320 | TQSHYGQCGGIGYSGPTVCASGTTCQVLN PYYSQCL (SEQ ID NO: 50) | 63.9 |
| TrCel6A | AAA34210 | CSSVWGQCGGQNWSGPTCCASGSTCVYSN DYYSQCL (SEQ ID NO: 49) | 100.0 |
| TrCel7B | AAA34212 | TQTHWGQCGGIGYSGCKTCTSGTTCQYSN DYYSQCL (SEQ ID NO: 51) | 63.9 |
| TrCel5A | AAA34213 | QQTVWGQCGGIGWSGPTNCAPGSACSTLN PYYAQCI (SEQ ID NO: 48) | 61.1 |
| TrCel61A | CAA71999 | TQTLYGQCGGSGYSGPTRCAPPATCSTLN PYYAQCL (SEQ ID NO: 53) | 52.8 |
| TrCel45A | CAA83846 | QQTLYGQCGGAGWTGPTTCQAPGTCKVQN QWYSQCL (SEQ ID NO: 52) | 50.0 |
| Cip1 | AAP57751 | TQTHYGQCGGIGYSGPTVCASGTTCQVLN PYYSQCL (SEQ ID NO: 54) | 61.1 |
| Swollenin | CAB92328 | CAALFGQCGGIGWSGTTCCVAGAQCSFVN DWYSQCL (SEQ ID NO: 55) | 58.3 |

CBMs and glycosyl hydrolase domains are often separated by a linker peptide. The term "linker peptide" is intended to be understood as a stretch of amino acids located between two functional domains and comprising from about 6 to about 60 amino acids. Without intending to be limiting, examples of two such functional domains include a CBM and glycosyl hydrolase domain, a CBM and an expansin domain, two CBMs and two glycosyl hydrolase domains. Interdomain linker peptides can be identified from amino acid sequence information using models such as described by Bae et al. (2008) and Suyama et al. (2003). Gilkes et al., (1991) presents the sequences of linkers from a variety of cellulases and other bacterial and fungal proteins encompassed by this definition. Amino acid sequences of the linker peptides of eight cellulase, hemicellulase and related proteins from *Trichoderma reesei* are shown in Table 3. The calculated isoelectric point (pI) and percentage of proline and threonine/serine in each of these linkers is shown as well.

Linker peptides are typically basic peptides, particularly enriched in serine, threonine and proline, relative to non-linker sequences. As presented in Table I of Gilkes et al (1991), proline, serine and threonine account for 50% or more of the amino acids in all linker peptide sequences from bacterial and fungal glycosl hydrolases (xylanases, endoglucanases, exoglucanases). For the purposes defined herein, a linker peptide may be defined as a stretch of 6-60 amino acids, at least 50% of which are proline, serine or threonine, that is naturally found between a glycosyl hydrolase domain and a CBM, two glycosyl hydrolase domains, two CBMs, or between another functional domain and either a glycosyl hydrolase catalytic domain or a CBM. Proline, serine and threonine may account for 50%, 60%, 70%, 80% 90% or 100% of the amino acids in the linker peptide ((# proline+threonine+serine)/# amino acids in linker×100%). One of skill in the art recognizes that the amino acid sequence of a given linker may be modified by the addition, deletion or substitution of one or more amino acids and still be considered a linker peptide.

TABLE 3

Linker sequences and relative key amino acid compositions of eight *Trichoderma* proteins.

| Protein | Accession No* | Linker Sequence (SEQ ID NO) | Amino Acids | # (%) Proline +Serine + Threonine |
|---|---|---|---|---|
| TrCel7A | P62694 | PPGGNPPGTTTTRRPATTTGSS PGP (SEQ ID NO: 39) | 25 | 16(64%) |
| TrCel6A | P07987 | PGAASSSSSTRAASTTSRVSPT TSRSSSATPPPGSTTTRVPPVG (SEQ ID NO: 83) | 44 | 29(66%) |
| TrCel7B | P07981 | PPPPPASSTTFSTTRRSSTTSSSP SCTQT (SEQ ID NO: 43) | 29 | 23(79%) |
| TrCel5A | P07982 | PGATTITTSTRPPSGPTTTTRAT STSSSTPPTSS (SEQ ID NO: 42) | 34 | 27(79%) |
| TrCel61A | O14405 | SSAATATASATVPGGGSGPTS RTTTTARTTQASSRPSSTPPAT TSAPAGGP (SEQ ID NO: 45) | 51 | 30(59%) |
| TrCel45A | P43317 | DTGSTPPGSSPPATSSSPPSGGG (SEQ ID NO: 44) | 23 | 16(70%) |
| Cip1 | AAP57751 | PGSPGGPGSSTTGRSSTSGPTST SRPSTTIPPPTSRTTTATGP (SEQ ID NO: 46) | 43 | 31(72%) |
| Swollenin | CAB92328 | PPNGTTSSSLVSRTSSASSSVGS SSPGGNSPTGSAST YTTTDTAT (SEQ ID NO: 47) | 45 | 29(64%) |

*All are SwissProt accession numbers, except for Cip1 and Swollenin, which are GenPept Accession Numbers.

Decreasing the Inactivation of Modified Cellulase Enzymes by Lignin

The extent to which a parental or modified cellulase enzyme, as defined above, binds to lignin can be determined by pre-incubating the cellulase enzyme with purified lignin for a set period of time and then measuring the residual protein concentration and/or enzyme activity in solution using assay methods known to one of skill in the art. If the purified lignin is insoluble, the protein-lignin complexes can be readily separated from the bulk solution containing unbound protein by centrifugation or filtration. The lignin may be purified from a lignocellulosic feedstock (described below) by acid-extraction, alkali extraction, extraction with organic solvents, or enzymatic digestion of the lignocellulose with hydrolytic enzymes. The determination of the relative binding of parental and modified cellulase enzymes is not dependent on the method used to purify the lignin, the source of the lignin or the assay methods used to detect the unbound cellulase enzyme in solution. Methods for measuring the relative binding of parental and modified cellulase enzymes are provided in Example 9.

The decrease in the inactivation of the modified cellulase enzymes by lignin is determined by measuring the degradation of a cellulose substrate in the presence and absence of lignin and then taking the ratio of activity in the presence of lignin to the activity in the absence of lignin. The lignin present in such a cellulose hydrolysis reaction can be part of the insoluble substrate, such as in pre-treated lignocellulose, or be isolated in a soluble or insoluble form. If the lignin is isolated or purified, the inactivation of the modified or parental cellulase enzyme by lignin is determined by measuring the cellulase activity in equivalent hydrolysis reactions, wherein one of the reactions contains a sufficient amount of lignin to reduce the cellulase activity. Alternatively, isolated lignin that has been treated to be less deactivating by coating with a non-specific protein such as bovine serum albumin (BSA), a surfactant or other chemical can be added to the control reaction in the same amounts as the untreated lignin. If the lignin is part of the insoluble substrate, the inactivation of the modified or parental cellulase enzyme by lignin is determined by taking the ratio of cellulase activity on a bleached substrate (from which the lignin has been removed, for example, by an oxidant such as chlorine dioxide) and the cellulase activity on an unbleached, lignin-containing substrate. A modified cellulase enzyme with decreased inactivation by lignin will show a higher activity ratio (untreated, isolated lignin: no lignin or treated lignin) than the parental cellulase enzyme.

There are several assays for measuring cellulose-hydrolyzing activity of the modified and parental cellulase enzymes known to one of skill in the art. For example, hydrolysis of cellulose can be monitored by measuring the enzyme-dependent release of reducing sugars, which are quantified in subsequent chemical or chemienzymatic assays known to one of skill in the art, including reaction with dinitrosalisylic acid (DNS). Hydrolysis of polysaccharides can also be monitored by chromatographic methods that separate and quantify soluble mono-, di- and oligo-saccharides released by the enzyme activity. In addition, soluble colorimetric substrates may be incorporated into agar-medium on which a host microbe expressing and secreting a parental or modified cellulase enzyme is grown. In such an agar plate assay, activity of the cellulsae is detected as a colored or colorless halo around the individual microbial colony expressing and secreting an active cellulase. It will be appreciated, however, that the practice of the present invention is not limited by the method used to assess the activity of the modified cellulase enzyme. A method for the measuring cellulose-hydrolyzing activity of the modified cellulases of the present invention is provided in Example 9.

The effect of a variety of modified linker peptides with amino acid substitutions that decrease the isoelectric point or increase the threonine:serine ratio of the linker peptide on the lignin binding and cellulose-hydrolyzing activity in the presence of untreated lignin (−BSA) and treated lignin (+BSA), was determined via a comparative study of the parental and modified cellulase enzymes as described in Examples 6 and 7. Furthermore, the binding of parental and modified cellulase enzymes, comprising said modified linker peptides, to untreated lignin was determined, as described in Example 9. The results are shown in Table 4, below. All of the modified cellulase enzymes comprising modified linker peptides show at least a 20% decrease in lignin binding (20% higher $K_L$) and/or 11% higher ratio of activity in the presence of untreated lignin: activity in the presence of BSA-treated lignin (10% increase in ±BSA activity ratio).

TABLE 4

Effect of modified linker peptides with decreased pI and/or increased threonine: serine ratio on the cellulose-hydrolyzing activity of the resulting modified cellulase enzymes in the presence of lignin (±BSA ratio) and on the lignin-binding (Relative $K_L$)

| Modified Cellulase Enzyme (SEQ ID NO) | Modified Linker Peptide[a] (SEQ ID NO:) | T:S Ratio | Calculated pI | ±BSA Activity Ratio | Relative $K_L$ |
|---|---|---|---|---|---|
| TrCel6A-S413P ("TrCel6A[wt]") (SEQ ID NO: 9) | PGAASSSSSTRAASTTSRVSPTTSR SSSATPPPGSTTTRVPPVG (SEQ ID NO: 83) | 9:14 | 12.48 | 1.00[bc] | 1.0[de] |
| TrCel6A-G40D-S413P (SEQ ID NO: 11) | P**D**AASSSSSTRAASTTSRVSPTTSR SSSATPPPGSTTTRVPPVG (SEQ ID NO: 26) | 9:14 | 12.00 | 1.18[b] | 3.3[d] |
| TrCel6A-S45N-S413P (SEQ ID NO: 12) | PGAASS**N**SSTRAASTTSRVSPTTSR SSSATPPPGSTTTRVPPVG (SEQ ID NO: 27) | 9:13 | 12.48 | 1.18[b] | 4.1[d] |
| TrCel6A-R63L-S413P (SEQ ID NO: 13) | PGAASSSSSTRAASTTSRVSPTTS**L** SSSATPPPGSTTTRVPPVG (SEQ ID NO: 28) | 9:14 | 12.30 | 1.15[b] | 1.8[d] |
| TrCel6A-P71T-S413P (SEQ ID NO: 14) | PGAASSSSSTRAASTTSRVSPTTSR SSSATPP**T**GSTTTRVPPVG (SEQ ID NO: 32) | 10:14 | 12.48 | 1.11[b] | 2.6[d] |
| TrCel6A-G72D-G231D-S413P (SEQ ID NO: 16) | PGAASSSSSTRAASTTSRVSPTTSR SSSATPPP**D**STTTRVPPVG (SEQ ID NO: 29) | 9:14 | 12.00 | 1.14[b] | 4.6[d] |
| TrCel6A-T76A-S413P (SEQ ID NO: 15) | PGAASSSSSTRAASTTSRVSPTTSR SSSATPPPGSTT**A**RVPPVG (SEQ ID NO: 30) | 8:14 | 12.48 | 1.14[b] | 3.6[d] |
| TrCel6A-V81D-Q204K-S413P (SEQ ID NO: 17) | PGAASSSSSTRAASTTSRVSPTTSR SSSATPPPGSTTTRVPP**D**G (SEQ ID NO: 31) | 9:14 | 12.00 | 1.18[b] | 2.5[d] |

TABLE 4-continued

Effect of modified linker peptides with decreased pI and/or increased threonine: serine ratio on the cellulose-hydrolyzing activity of the resulting modified cellulase enzymes in the presence of lignin (±BSA ratio) and on the lignin-binding (Relative $K_L$)

| Modified Cellulase Enzyme (SEQ ID NO) | Modified Linker Peptide[a] (SEQ ID NO:) | T:S Ratio | Calculated pI | ±BSA Activity Ratio | Relative $K_L$ |
|---|---|---|---|---|---|
| TrCel6A-S35F-G40D-S45N-R63L-P71T-G72D-T76A-V81D-S413P (SEQ ID NO: 18) | PDAASS**N**SSTRAASTTSRVSPTTS**L** SSSATPP**TD**STT**A**RVPP**DG** (SEQ ID NO: 34) | 9:12 | 6.47 | 1.39[b] 1.80[c] | 3.9[d] |
| TrCel6A$^{\Delta 1}$-S413P (SEQ ID NO: 19) | PGAASSSSSTRAASTTSRVSPTTS-- ---------- (SEQ ID NO: 35) | 5:10 | 12.00 | 1.34[c] | 1.2[e] |
| TrCel6A$^{\Delta 2}$-S413P (SEQ ID NO: 20) | ----------- PTTSRSSSATPPPGSTTTRVPPVG (SEQ ID NO: 36) | 6:6 | 12.00 | 1.22[c] | 1.0[e] |
| TrCel6A R→E S413P (SEQ ID NO: 21) | PGAASSSSST**E**AASTTS**E**VSPTTS**E** SSSATPPPGSTTT**E**VPPVG (SEQ ID NO: 33) | 9:14 | 3.58 | 1.21[c] | 2.4[e] |
| TrCel6A$^{S\rightarrow T}$-S413P (SEQ ID NO: 22) | PGAA**TTTTTT**RAA**T**TTTRV**T**PTTT R**TTT**ATPPPG**T**TTTRVPPVG (SEQ ID NO: 37) | 22:1 | 12.48 | — | — |
| TrCel6A$^{R\rightarrow E/S\rightarrow T}$-S413P (SEQ ID NO: 23) | PGAA**TTTTTTE**AA**T**TTT**E**V**T**PTTT **ETTT**ATPPPG**T**TTT**E**VPPVG (SEQ ID NO: 38) | 22:1 | 3.58 | 1.22[c] | 2.2[e] |
| TrCel7A$^{Wt}$ (SEQ ID NO: 3) | PPGGNRGTTTTRRPATTTGSSPGP (SEQ ID NO: 39) | 7:2 | 12.30 | — | 1.00[e] |
| TrCel7A-R449E-R450E (SEQ ID NO: 24) | PPGGNEGTTTT**EE**PATTTGSSPGP (SEQ ID NO: 40) | 7:2 | 3.67 | — | 2.2[e] |
| TrCel7A-R449E-R450E-S457T-S458T- (SEQ ID NO: 25) | PPGGNEGTTTT**EE**PATTTG**TT**PGP (SEQ ID NO: 41) | 9:0 | 3.67 | — | 2.1[e] |

[a]Amino acid substitutions relative to the corresponding parental linker are indicated in bold.
[b]Indicates a ±BSA ratio from Assay 1 (Example 6)
[c]Indicates a ±BSA ratio from Assay 2 (Example 7)
[d]Indicates a relative $K_L$ measured for a protein secreted from *S. cerevisiae*
[e]Indicates a relative $K_L$ measured for a protein secreted from *T. reesei*

Genetic Constructs Encoding Modified Cellulase Enzymes

The present invention also relates to genetic constructs comprising nucleic acid sequences encoding the modified cellulase enzymes operably linked to regulatory nucleic acid sequences directing the expression and secretion of the modified cellulase enzymes from a host microbe. By "regulatory nucleic acid sequences" it is meant a promoter and a nucleic acid sequence encoding a secretion signal peptide. The regulatory nucleic acid sequences may be derived from genes that are highly expressed and secreted in the host microbe under industrial fermentation conditions. For example, the regulatory nucleic acid sequences are derived from any one or more of the *Trichoderma reesei* cellulase or hemicellulase genes.

The genetic construct may further comprise a selectable marker gene to enable isolation of a genetically modified microbe transformed with the construct as is commonly known to those of skill in the art. The selectable marker gene may confer resistance to an antibiotic or the ability to grow on medium lacking a specific nutrient to the host organism that otherwise could not grow under these conditions. The present invention is not limited by the choice of selectable marker gene, and one of skill in the art may readily determine an appropriate gene. For example, the selectable marker gene may confer resistance to hygromycin, phleomycin, kanamycin, geneticin, or G418, complement a deficiency of the host microbe in one of the trp, arg, leu, pyr4, pyr, ura3, ura5, his, or ade genes or confer the ability to grow on acetamide as a sole nitrogen source.

The genetic construct may further comprise other nucleic acid sequences, for example, transcriptional terminators, nucleic acid sequences encoding peptide tags, synthetic sequences to link the various nucleic acid sequences together, origins of replication, and the like. The practice of the present invention is not limited by the presence of any one or more of these other nucleic acid sequences.

Genetically Modified Microbes Producing Modified Cellulase Enzymes

The modified cellulase enzymes may be expressed and secreted from a genetically modified microbe produced by transformation of a host microbe with a genetic construct encoding the modified cellulase enzyme. The host microbe may be a bacterium, such as *Eschericia coli* or *Streptomyces lividans*, a yeast such *Saccharomyces, Pichia*, or *Hansenula*, or a filamentous fungus such as *Trichoderma, Hypocrea, Aspergillus, Fusarium, Humicola, Chrysosporium, Myceliopthora* or *Neurospora*. Typically, the host microbe is one from which the gene(s) encoding any or all parental cellulase enzymes have been deleted. In a most preferred embodiment, the host microbe is an industrial strain of *Trichoderma reesei.*

The genetic construct may be introduced into the host microbe by any number of methods known by one skilled in the art of microbial transformation, including but not limited to, treatment of cells with $CaCl_2$, electroporation, biolistic bombardment, PEG-mediated fusion of protoplasts (e.g. White et al., WO 2005/093072). After selecting the recombinant fungal strains expressing the modified cellulase enzyme, the selected recombinant strains may be cultured in submerged liquid fermentations under conditions that induce the expression of the modified cellulase enzyme. Preferably, the modified cellulase enzyme is produced in submerged liquid culture fermentation and separated from the cells at the end of the fermentation. The cells may be separated by filtration, centrifugation, or other processes familiar to those skilled in the art. The cell-free glycosidase-containing fraction may then be concentrated (for example, via ultrafiltration), preserved, and/or stabilized prior to use.

Hydrolyzing Cellulose in the Presence of Lignin with Modified Cellulase Enzymes

The modified cellulase enzymes of the present invention are used for the enzymatic hydrolysis of cellulose in a hydrolysis reaction further comprising lignin. For example, the modified cellulase enzyme of the present invention is used for the enzymatic hydrolysis of a pretreated lignocellulosic substrate, such as in industrial processes producing fermentable sugars, sugar alcohols or fuel alcohols from lignocellulose. The modified cellulase enzymes of the present invention may be part an enzyme mixture comprising other cellulase enzymes, hemicellulases, glucosidases, and non-hydrolytic proteins known to alter cellulose structure, such as swollenins and expansins.

By the term "enzymatic hydrolysis", it is meant a process by which glycosidase enzymes or mixtures, including those comprising the modified cellulase enzyme of the present invention, act on polysaccharides to convert all or a portion thereof to soluble sugars.

The modified cellulase enzyme of the invention is used in a process for enzymatic hydrolysis of a "pretreated lignocellulosic substrate." A pretreated lignocellulosic substrate is a material of plant origin that, prior to pretreatment, contains at least 20% cellulose (dry wt), more preferably greater than about 30% cellulose, even more preferably greater than 40% cellulose, for example 20, 22, 24, 26, 28, 30, 32, 34, 36, 38, 40, 42, 44, 46, 48, 50, 55, 60, 65, 70, 75, 80, 85, 90% or any % therebetween, and at least 10% lignin (dry wt), more typically at least 12% (dry wt) and that has been subjected to physical and/or chemical processes to make the fiber more accessible and/or receptive to the actions of cellulolytic enzymes.

After pretreatment, the lignocellulosic feedstock may contain higher levels of cellulose. For example, if acid pretreatment is employed, the hemicellulose component is hydrolyzed, which increases the relative level of cellulose. In this case, the pretreated feedstock may contain greater than about 20% cellulose and greater than about 10% lignin. For example, the pretreated lignocellulosic feedstock contains greater than about 20% cellulose and greater than about 12% lignin.

Lignocellulosic feedstocks that may be used in the invention include, but are not limited to, agricultural residues such as corn stover, wheat straw, barley straw, rice straw, oat straw, canola straw, and soybean stover; fiber process residues such as corn fiber, sugar beet pulp, pulp mill fines and rejects or sugar cane bagasse; forestry residues such as aspen wood, other hardwoods, softwood, and sawdust; grasses such as switch grass, *miscanthus*, cord grass, and reed canary grass; or post-consumer waste paper products.

The lignocellulosic feedstock may be first subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, a hammer mill.

Non-limiting examples of pretreatment processes include chemical treatment of a lignocellulosic feedstock with sulfuric or sulfurous acid, or other acids; ammonia, lime, ammonium hydroxide, or other alkali; ethanol, butanol, or other organic solvents; or pressurized water (See U.S. Pat. Nos. 4,461,648, 5,916,780, 6,090,595, 6,043,392, 4,600,590; which are incorporated herein by reference).

The pretreatment may be carried out to hydrolyze the hemicellulose, or a portion thereof, that is present in the lignocellulosic feedstock to monomeric sugars, for example xylose, arabinose, mannose, galactose, or a combination thereof. Preferably, the pretreatment is carried out so that nearly complete hydrolysis of the hemicellulose and a small amount of conversion of cellulose to glucose occurs. During the pretreatment, typically an acid concentration in the aqueous slurry from about 0.02% (w/w) to about 2% (w/w), or any amount therebetween, is used for the treatment of the lignocellulosic feedstock. The acid may be, but is not limited to, hydrochloric acid, nitric acid, sulfurous acid (including the addition of sulfur dioxide or sulfur dioxide and water), phosphoric acid or sulfuric acid. For example, the acid used during pretreatment may be sulfuric acid.

One method of performing acid pretreatment of the feedstock is steam explosion using the process conditions set out in U.S. Pat. No. 4,461,648 (Foody, which is herein incorporated by reference). Another method of pretreating the feedstock slurry involves continuous pretreatment, meaning that the lignocellulosic feedstock is pumped through a reactor continuously. Continuous acid pretreatment is familiar to those skilled in the art; see, for example, U.S. Pat. No. 5,536,325; WO 2006/128304 and U.S. Pat. No. 4,237,226. Additional techniques known in the art may be used as required such as the process disclosed in U.S. Pat. No. 4,556,430.

As noted above, the pretreatment may be conducted with alkali. In contrast to acid pretreatment, pretreatment with alkali may not hydrolyze the hemicellulose component of the feedstock, but rather the alkali reacts with acidic groups present on the hemicellulose to open up the surface of the substrate. The addition of alkali may also alter the crystal structure of the cellulose so that it is more amenable to hydrolysis. Examples of alkali that may be used in the pretreatment include ammonia, ammonium hydroxide, potassium hydroxide, and sodium hydroxide. The pretreatment is preferably not conducted with alkali that is insoluble in water, such as lime and magnesium hydroxide.

An example of a suitable alkali pretreatment is Ammonia Freeze Explosion, Ammonia Fiber Explosion or Ammonia Fiber Expansion ("AFEX" process). According to this process, the lignocellulosic feedstock is contacted with ammonia or ammonium hydroxide in a pressure vessel for a sufficient time to enable the ammonia or ammonium hydroxide to alter the crystal structure of the cellulose fibers. The pressure is then rapidly reduced, which allows the ammonia to flash or boil and explode the cellulose fiber structure. (See U.S. Pat. Nos. 5,171,592, 5,037,663, 4,600,590, 6,106,888, 4,356,196, 5,939,544, 6,176,176, 5,037,663 and 5,171,592, which are each incorporated herein by reference). The flashed ammonia may then be recovered according to known processes.

The pretreated lignocellulosic feedstock may be processed after pretreatment but prior to the enzymatic hydrolysis by any of several steps, such as dilution with water, washing with water, buffering, filtration, or centrifugation, or a combination of these processes, prior to enzymatic hydrolysis, as is familiar to those skilled in the art.

The pretreated lignocellulosic feedstock is next subjected to enzymatic hydrolysis. By the term "enzymatic hydrolysis", it is meant a process by which cellulase enzymes act on cellulose to convert all or a portion thereof to soluble sugars. Soluble sugars are meant to include water-soluble hexose monomers and oligomers of up to six monomer units that are derived from the cellulose portion of the pretreated lignocellulosic feedstock. Examples of soluble sugars include, but are not limited to, glucose, cellobiose, cellodextrins, or mixtures thereof. The soluble sugars may be predominantly cellobiose and glucose. The soluble sugars may predominantly be glucose.

The enzymatic hydrolysis process preferably converts about 80% to about 100% of the cellulose to soluble sugars, or any range therebetween. More preferably, the enzymatic hydrolysis process converts about 90% to about 100% of the cellulose to soluble sugars, or any range therebetween. In the most preferred embodiment, the enzymatic hydrolysis process converts about 98% to about 100% of the cellulose to soluble sugars, or any range therebetween.

The enzymatic hydrolysis using the cellulase mixture may be batch hydrolysis, continuous hydrolysis, or a combination thereof. The hydrolysis may be agitated, unmixed, or a combination thereof.

The enzymatic hydrolysis is preferably carried out at a temperature of about 45° C. to about 75° C., or any temperature therebetween, for example a temperature of 45, 50, 55, 60, 65, 70, 75° C., or any temperature therebetween, and a pH of about 3.5 to about 7.5, or any pH therebetween, for example a temperature of 3.5, 4.0, 4.5, 5.0, 5.5, 6.0, 6.5, 7.0, 7.5, or pH therebetween. The initial concentration of cellulose in the hydrolysis reactor, prior to the start of hydrolysis, is preferably about 4% (w/w) to about 15% (w/w), or any amount therebetween, for example 4, 6, 8, 10, 12, 14, 15% or any amount therebetween. The dosage of all cellulase enzymes may be about 0.1 to about 100 mg protein per gram cellulose, or any amount therebetween, for example 0.1, 0.5, 1, 5, 10, 15, 20, 25, 30, 40, 50, 60, 70, 80, 90, 100 mg protein per gram cellulose or any amount therebetween. The hydrolysis may be carried out for a time period of about 0.5 hours to about 200 hours, or any time therebetween, for example, the hydrolysis may be carried out for a period of 4 hours to 100 hours, or any time therebetween, or it may be carried out for 0.5, 1, 2, 4, 6, 8, 10, 12, 14, 15, 20, 25, 30, 35, 40, 45, 50, 55, 60, 65, 70, 75, 80, 85, 90, 95, 100, 120, 140, 160, 180, 200 or any time therebetween. It should be appreciated that the reaction conditions are not meant to limit the invention in any manner and may be adjusted as desired by those of skill in the art.

The enzymatic hydrolysis is typically carried out in a hydrolysis reactor. The enzyme mixture is added to the pretreated lignocellulosic feedstock (also referred to as the "substrate") prior to, during, or after the addition of the substrate to the hydrolysis reactor.

Preferably, the modified cellulase enzyme is produced in one or more submerged liquid culture fermentations and may be separated from the cells at the end of the fermentation by filtration, centrifugation, or other processes familiar to those skilled in the art. The cell-free cellulase-containing fraction may then be concentrated (for example, via ultrafiltration), preserved, and/or stabilized prior to use. Alternatively, the modified cellulase enzyme(s) are not separated from the cells, but are added to the enzymatic hydrolysis with the cells.

EXAMPLES

The present invention will be further illustrated in the following examples. However, it is to be understood that these examples are for illustrative purposes only and should not be used to limit the scope of the present invention in any manner.

Example 1 sets forth the strains and vectors used in the following examples. Example 2 relates to the cloning of the TrCel6A-S413P gene and transformation in yeast. Example 3 summarizes the preparation of the error prone-PCR library of TrCel6A-S413P (also referred to as TrCel6A$^{wt}$). Example 4 pertains to the expression of parental and modified TrCel6A cellulases from yeast microculture. Example 5 sets forth a method for the isolation and preparation of lignin. Examples 6 and 7 set forth methods for the high-throughput screening assays to identify modified cellulases with decreased inactivation by lignin. Examples 8 and 9 relate to the expression and characterization of modified and parental cellulases with decreased inactivation by lignin. Examples 10 and 11 set forth methods for the preparation and testing of the Aggregate TrCel6A Variant modified cellulase comprising mutations at positions 35, 40, 45, 63, 71, 72, 76, 81. The design and preparation of several constructs encoding modified TrCel6A cellulases with additional novel linker sequences is detailed in Example 12 and the expression and characterization of these modified cellulases from yeast is described in Example 13. Examples 14 and 15 relate to the expression of these modified cellulases from *Trichoderma* and their subsequent analysis, respectively. Example 16 relates to the characterization of modified and parental TrCel7A cellulases with decreased inactivation by lignin

Example 1

Strains and Vectors

*Saccharomyces cerevisiae* strain YDR483W BY4742 [14317] (MATα his3Δ1 leu2Δ0 lys2Δ0 ura3Δ0 Δkre2) was obtained from ATCC (#4014317). *Escherichia coli* strain DH5α (F$^-$ ϕ80lacZAM15 Δ(lacZY A-argF)U169 recA1 endA1 hsdR17($r_k^-$, $m_k^+$) phoA supE44 thi-1 gyrA96 relA1λ$^-$) was obtained from Invitrogen. The YEp352/PGK91-1 vector was obtained from the National Institute of Health. The YEpFLAGΔKpn10-S413P vector is described in U.S. Publication No. 2008/0076152A1. The YEpFLAG-1 vector was obtained from Sigma as a part of the Amino-Terminal Yeast FLAG Expression Kit. *Trichoderma reesei* strain P297J, a proprietary strain of Iogen Corporation, is a derivative of *T. reesei* strain BTR213 from which the genes encoding Cel7A, Cel6A and Cel7B have been deleted. Strain BTR213 is a proprietary strain of Iogen Corporation derived from *T. reesei* strain RutC30 (ATCC 56765).

Example 2

Cloning of the TrCel6A-S413 ("TrCel6A$^{wt}$") Gene into the YEp352/PGK91-1 and Transformation in Yeast In order to facilitate cloning using NheI and KpnI restriction enzymes, the unique NheI site at position 1936 of the YEp352/PGK91-1 vector was blunted using the DNA Polymerase I large (Klenow) fragment to generate YEp352/PGK91-1ΔNheI. The TrCel6A-S413P gene was amplified by PCR from YEpFLAGΔKpn10-S413P vector (U.S. Publication No. 2008/0076152A1) using primers 5'NheCel6A and 3'BglKpnCel6A. In parallel, the yeast α-factor leader sequence was amplified by PCR from the YEpFLAG-1 vector (Sigma) using primers (5'BglAlphaSS and 3'NheAlphaSS) to introduce BglII at the 5' end and a NheI site at 3' end of the amplicon.

The yeast α-factor leader sequence was isolated by BglII/NheI digestion and a three piece ligation performed with the TrCel6A-S413P gene (isolated by NheI/BglII digestion) and YEp352/PGK91-1ΔNheI vector (isolated by BglII digestion). The resulting vector YEp352/PGK91-1ΔNheI-$\alpha_{ss}$-TrCel6A-S413P (FIG. 1A) was transformed in yeast strain BY4742 using the procedure described by Gietz, R. D. and Woods, R. A. (2002). Primer sequences are listed below:

```
5'BglAlphaSS:
                                        (SEQ ID NO: 56)
5'ACC AAA AGA TCT ATG AGA TTT CCT TCA ATT

3'NheAlphaSS:
                                        (SEQ ID NO: 57)
5'TGA GCA GCT AGC CCT TTT ATC CAA AGA TAC

5'NheCel6A:
                                        (SEQ ID NO: 58)
5'AAA AGG GCT AGC TGC TCA AGC GTC TGG GGC

3'BglKpnCel6A:
                                        (SEQ ID NO: 59)
5'GAG CTC AGA TCT GGT ACC TTA CAG GAA CGA TGG GTT
```

Example 3

Making Error Prone-PCR Libraries

Random mutagenesis libraries were generated using two methods: a MUTAZYME® II DNA polymerase method and a $Mn^{2+}$/biased dNTP mix method. For the MUTAZYME® II DNA polymerase method, a series of four independent PCR were performed using 10, 20, 30, 40 ng of YEp352/PGK91-1ΔNheI-$\alpha_{ss}$-TrCel6A-S413P vector and the MUTAZYME® II DNA polymerase with primers YalphaN21 and 3'PGK-term. The amplification was done for 25 cycles. The four PCR products were pooled and diluted to 10 ng/μL. A second PCR mutagenesis step was performed using 30ng of pooled PCR product with MUTAZYME® II DNA polymerase using the same primers for 30 amplification cycles. The YEp352/PGK91-1ΔNheI-$\alpha_{ss}$-TrCel6A-S413P vector was digested with NheI and KpnI and the empty vector fragment was isolated. This linear fragment and the final amplicon were transformed simultaneously and cloned by in vivo recombination into yeast strain BY4742 (Butler et al., 2003).

Example 4

Expression and Isolation of Parental and Modified Cellulases from Microplate Cultures This example describes the selection and expression of parental and modified TrCel6A cellulases from *Saccharomyces cerevisiae* for use in the high-throughput screening assays (Example 6 and 7).

*S. cerevisiae* transformants, from Example 3, were grown on plates containing synthetic complete medium (SC: 2% agar w/v, 0.17% yeast nitrogen base w/v, 0.078%—Ura drop-out supplement w/v, 2% glucose w/v, 2% casamino acids w/v, 0.5% ammonium sulfate w/v, pH 5.5) and 0.12% Azo-barley-beta-glucan (Megazyme) for 4 days at 30° C.

Colonies showing visible clearing halos, after an overnight incubation at 45° C., were selected for liquid media pre-cultures by toothpick inoculation of 150 μL synthetic complete media (SC: 0.17% yeast nitrogen base w/v, 0.078%—Ura drop-out supplement w/v, 2% glucose w/v, 2% casamino acids w/v, 0.5% ammonium sulfate w/v, pH 5.5) in 96-well microplates. Pre-cultures were grown for 16-18 h at 30° C. and 300 rpm to stationary phase. For expression culture inoculation, 25 μL of pre-culture was used to inoculate 1 mL of SC media in deepwell microplates containing one glass bead. Expression cultures were grown for 3 days at 30° C. and 250 rpm with humidity control. Plates were centrifuged at 2800×rpm for 5 minutes to pellet cells and supernatant was aspirated for screening assays (Example 6 and 7). To the remaining pre-culture, stocks were prepared by the addition of glycerol to a final concentration of 15% and stored at −80° C.

Example 5

Preparation of Lignin

Wheat straw was pretreated using the methods described in U.S. Pat. No. 4,461,648. Following pretreatment, sodium benzoate was added at a concentration of 0.5% as a preservative. The pretreated material was then washed with six volumes of lukewarm (~35° C.) tap water using a Buchner funnel and filter paper.

A sample of pretreated wheat straw (167 g wet; 30% solids; 55% cellulose) was added to 625 mL of 82% $H_2SO_4$ with stirring in a 1 L flask, then stoppered and incubated at 50° C. with shaking for 4 hours. The remaining solids were filtered to dampness using a Buchner funnel and a glass fiber filter, resuspended in 1 L of water and adjusted to pH 4.5 with NaOH. The solids were filtered and washed with ~8 L water. Hereinafter, the solids are referred to as "lignin".

A portion of the lignin was treated with bovine serum albumin (BSA) to substantially block protein binding to the lignin (Yang and Wyman, 2006; U.S. Publication No. 2004/0185542A1; U.S. Publication No. 2006/088922A1; WO2005/024037A2; WO2009/429474A1). BSA treatment of lignin was performed by incubating equal amounts (w/w) of lignin and BSA at a concentration of 30 g/L in 50 mM citrate buffer (pH 5) containing 0.1% sodium benzoate for 5 days at 50° C. with shaking.

Example 6

High-Throughput Screening (HTS) of TrCel6A Gene Libraries for Lignin Resistant Modified Cellulases—Assay 1

This example describes the screening of modified TrCel6A cellulases with resistance to inactivation by lignin by comparison to a parental TrCel6A cellulase that had been cloned into *S. cerevisiae*.

Pre-binding of parental and modified cellulases to cellulose. An aliquot (0.175 mL) of supernatant from each variant as described in Example 4 was added to two separate microplate wells containing 0.05 mL cellulose at a concentration of 0.167% w/v, and incubated for 90 minutes at 4° C.

and 800 rpm. Microplates were then centrifuged at 2800×g for 3 min and 0.175 mL of supernatant was removed. An additional aliquot of supernatant (0.175 mL) from each variant was added to the same microplate wells and incubated for another 90 minutes under the same conditions. Microplates were again centrifuged at 2800×g for 3 min and 0.175 mL of supernatant was removed. A 0.175 mL volume of 50 mM citrate buffer (pH 5) was added to all wells and immediately the microplates were centrifuged at 2800×g for 3 min. Supernatant (0.175 mL) was removed.

Figure 2A:
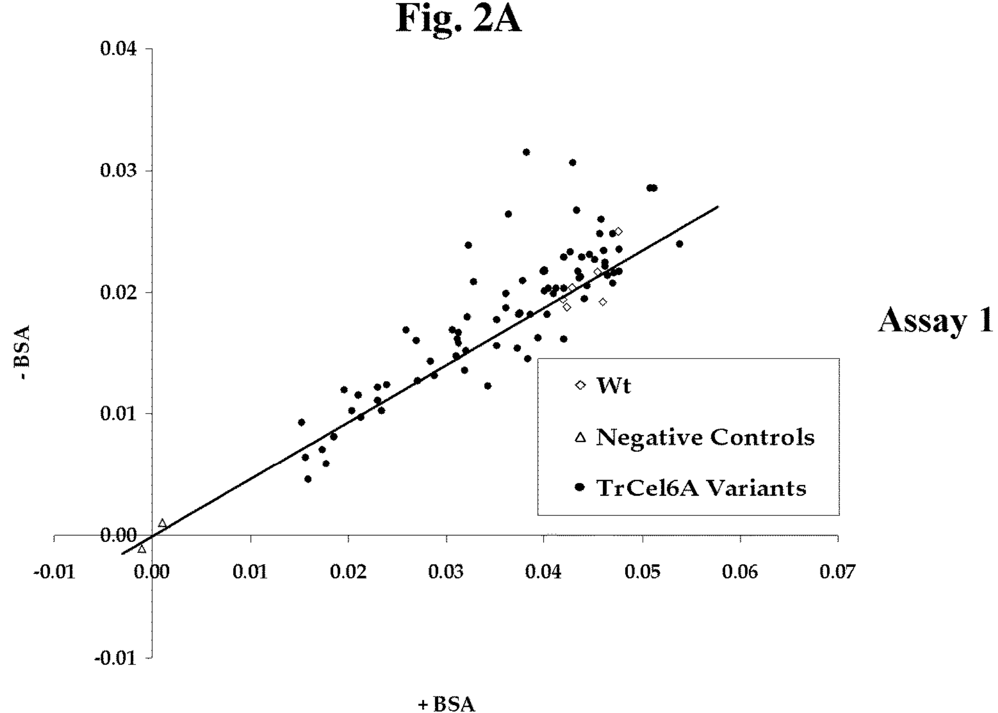
FIG. 2 contains two scatter plots "(A)" and "(B)". The data relate to the screening of one 96-well culture plate containing parental cellulase TrCel6A-S413P (Wt), filtrates from empty vector transformants (Negative Controls) and modified cellulases (TrCel6A variants). Scatter plot (A) illustrates enzyme activity in the presence of BSA-treated lignin (+BSA) versus enzyme activity in the presence of untreated lignin (−BSA) for high-throughput Assay 1 described in Example 6. Scatter plot (B) illustrates enzyme activity in the presence of BSA-treated lignin (+BSA) versus enzyme activity in the presence of untreated lignin (−BSA) for high-throughput Assay 2 described in Example 7.

Cellulose hydrolysis. Each modified and parental TrCel6A cellulase was incubated with both untreated lignin and BSA-treated lignin (0.100 mL) at a concentration of 2.68% (w/v) for 2 hours at 50° C. and 250 rpm. Following this period, *Trichoderma reesei* Cel7B and Cel5A (40 mg protein/g cellulose) and *A. niger* beta-glucosidase (125 IU/g cellulose) were added and the incubation proceeded for an additional 3 hours. Microplates were centrifuged for 3 min at 2800×g and an aliquot of supernatant was sampled for glucose. Enzyme activity was measured via the detection of glucose using a standard glucose oxidase/peroxidase coupled reaction assay (Trinder, 1969). A sample of the data from one screening plate is shown in FIG. 2A.

Figure 3:
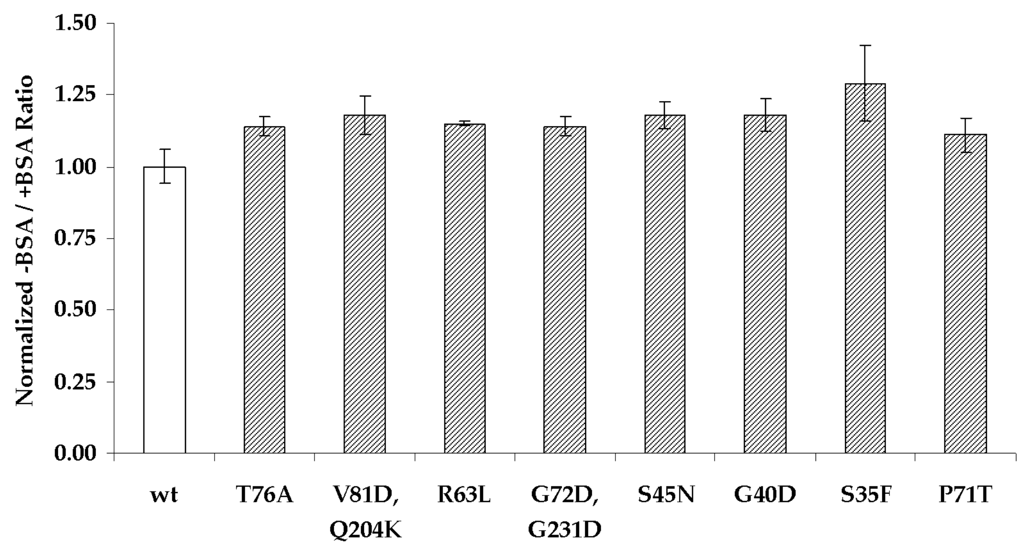
FIG. 3 is a bar graph showing −BSA: +BSA cellulase activity ratios normalized to parental cellulase TrCel6A-S413P (wt) for modified cellulases (TrCel6A variants) as measured in Assay 1.

Contained in each 96-well microplate were six parental TrCel6A-S413P cellulase controls used for comparison. A ±BSA-treated lignin ratio was calculated for all modified TrCel6A cellulases and TrCel6A-S413P by dividing the cellulase activity in the presence of lignin by the cellulase activity in the presence of BSA-treated lignin. The activity ratio for each modified TrCel6A cellulase was compared to the average of six parental TrCel6A-S413P controls on a particular microplate and positives (those having increased ratios) were selected at the 95% confidence level using a t-test (FIG. 3). All positive variants were produced again in microculture and re-screened to reduce the number of false positives.

Example 7

High-Throughput Screening of TrCel6A Libraries for Modified Cellulases—Assay 2

This example describes the screening of modified TrCel6A cellulases for resistance to lignin by comparison to the parental TrCel6A-S413P cellulase. An aliquot (150 μL) of yeast supernatant as described in Example 4 was pre-incubated with untreated lignin (1.6% w/v) in a 250 μL citrate buffered (50 mM; pH 5) reaction. An equivalent aliquot of supernatant from each modified cellulase was also pre-incubated with lignin (1.6% w/v) which was pre-treated with BSA. Pre-incubation was performed for 5.5 hours, in a 96-well microplate containing 1 glass bead, at 50° C. and 250 rpm (NB Innova 44). Contained in each 96-well microplate were six parental TrCel6A-S413P cellulase controls used for comparison. Following pre-incubation, microplates were centrifuged for 5 min at 2800 g and the supernatant was aspirated for residual activity assays.

Figure 2B:
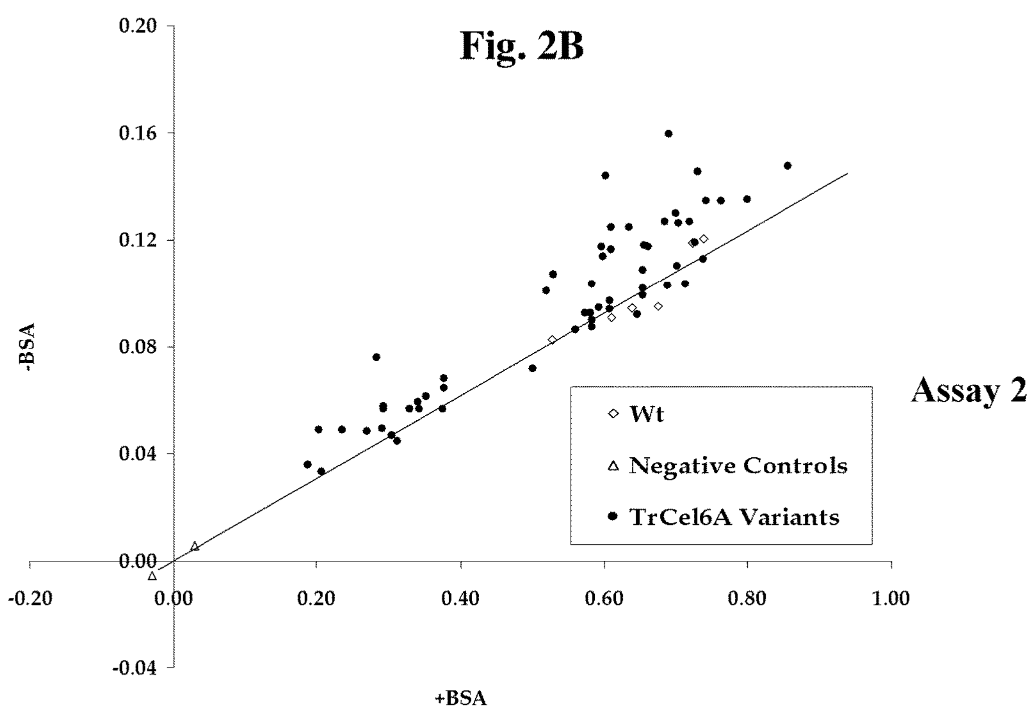

Supernatant (50 μL) was incubated with 0.5% beta-glucan in a 100 μL citrate buffered (50 mM; pH 5) reaction. Residual activity assays were performed for 16 hours for samples pre-incubated with untreated lignin and 3 hours for samples pre-incubated with BSA-treated lignin, in a PCR plate, at 50° C. A glucose standard curve was placed in the first column of the PCR ranging from 3 to 0.05 mg/mL. Following incubation, 80 μL of DNS was added to all wells and the plates were boiled for 10 min. An aliquot (150 μL) was transferred to a microplate well and the absorbance was measured at 560 nm. Residual enzyme activity was determined by converting A560 values to reducing equivalents using the glucose standard curve. A sample of the data from one screening plate is shown in FIG. 2B. An activity ratio was calculated for all modified TrCel6A cellulases and the parental TrCel6A-S413P cellulase by dividing the residual enzyme activity in the presence of untreated lignin by the residual enzyme activity in the presence of BSA-treated lignin. The activity ratio for each modified TrCel6A cellulase was compared to the average of six parental TrCel6A-S413P cellulase controls on a particular microplate and positives (those having increased ratios) were selected at the 95% confidence level using a t-test. All positive variants were produced again in microculture and re-screened to reduce the number of false positives.

DNS Reagent Contains:

| Component | g/L |
|---|---|
| 3,5-Dinitosalicylic acid (Acros) | 20 |
| Sodium hydroxide (Fisher) | 20 |
| Phenol (Sigma) | 4 |
| Sodium metabisulfate (Fisher) | 1 |

Example 8

Expression and Purification of Parental and Modified Cellulases from Large Scale Yeast Cultures 500 mL of sterile YPD medium (10 g/L yeast extract, 20 g/L peptone and 20 g/L glucose) was inoculated with 10 mL of an overnight culture of transformed *S. cerevisiae* grown from cells freshly picked from an agar plate. The 500 mL cultures were then incubated for 96 hours at 30° C. with orbital shaking at 200 rpm.

After incubation, the broth from each culture was centrifuged for 10 minutes at 9000 rpm and the pellet (containing yeast cells) discarded. The pH of the supernatant was adjusted to 5.0 and then allowed to cool to 4° C. for an hour. Subsequent to cooling, 625 g $(NH_4)_2SO_4$ was added to bring the yeast supernatant to 93% saturation. Precipitation was allowed to occur over a period of 2 hours at 4° C. with constant stirring. After centrifugation for 15 minutes at 9000 rpm, the supernatant was discarded.

The pellet was resuspended with pipetting in 20 mL of 50 mM citrate, pH 5.0. Once the pellet was resuspended, 80 mL of 0.1 M sodium acetate, 200 mM glucose and 1 mM gluconic acid lactone, pH 5.0 was added. Samples were then incubated at 4° C. for 30 min with gentle stirring. Each sample was then centrifuged at 3000 rpm for 3 minutes to pellet any insoluble material. The supernatant was removed carefully with a pipette to prevent disruption of the pellet and retained. The modified or parental TrCel6A cellulase in each sample was purified by APTC affinity chromatography as described by (Piyachomkwan et al., 1997). Purified TrCel6A cellulases were buffer exchanged into 50 mM citrate, pH 5.0 and concentrated using an Amicon stir cell and a 50 kDa NMWL polyethersulfone membrane. Protein concentrations were measured by UV absorbance (280 nm) using an extinction coefficient of $\varepsilon_{280\ nm}$=2.062 mL·mg$^{-1}$·cm.

Example 9

Enzymatic Characterization of Parental and Modified Cellulases

Purified parental and modified cellulases (0.03 mg) were incubated with untreated lignin (1.04 mg) in stoppered glass flasks in a total volume of 2 mL of 50 mM citrate buffer, pH 5.0. Incubations were done at 50° C. for up to 24 hours with orbital shaking at 250 rpm. 0.2 mL samples were collected from each flask at 0, 0.5, 1, 2, 3, 4, 6 and 24 h. Each sample was centrifuged to separate the lignin and stored at 4° C.

Upon completion of the time course, each sample was vortexed briefly to resuspend the pellet and 50 μL of slurry containing both soluble and insoluble material added to a microtitre plate containing 3 glass beads/well. To each well, 20 μL of a dilute preparation of *Trichoderma* cellulase devoid of cellobiohydrolase activity (1 μg total protein) and purified *Trichoderma* Cel3A (1.4 μg) were added to supplement cellobiohydrolase hydrolysis activity. Finally, 0.2 mL of delignified cellulose slurry (0.25% cellulose) was added to each well. The assay plate was incubated at 50° C. for 2 h with orbital shaking at 250 rpm. The plate was then centrifuged at 2000×g for 2 min and the glucose concentrations measured as described in Example 6.

Figure 4:
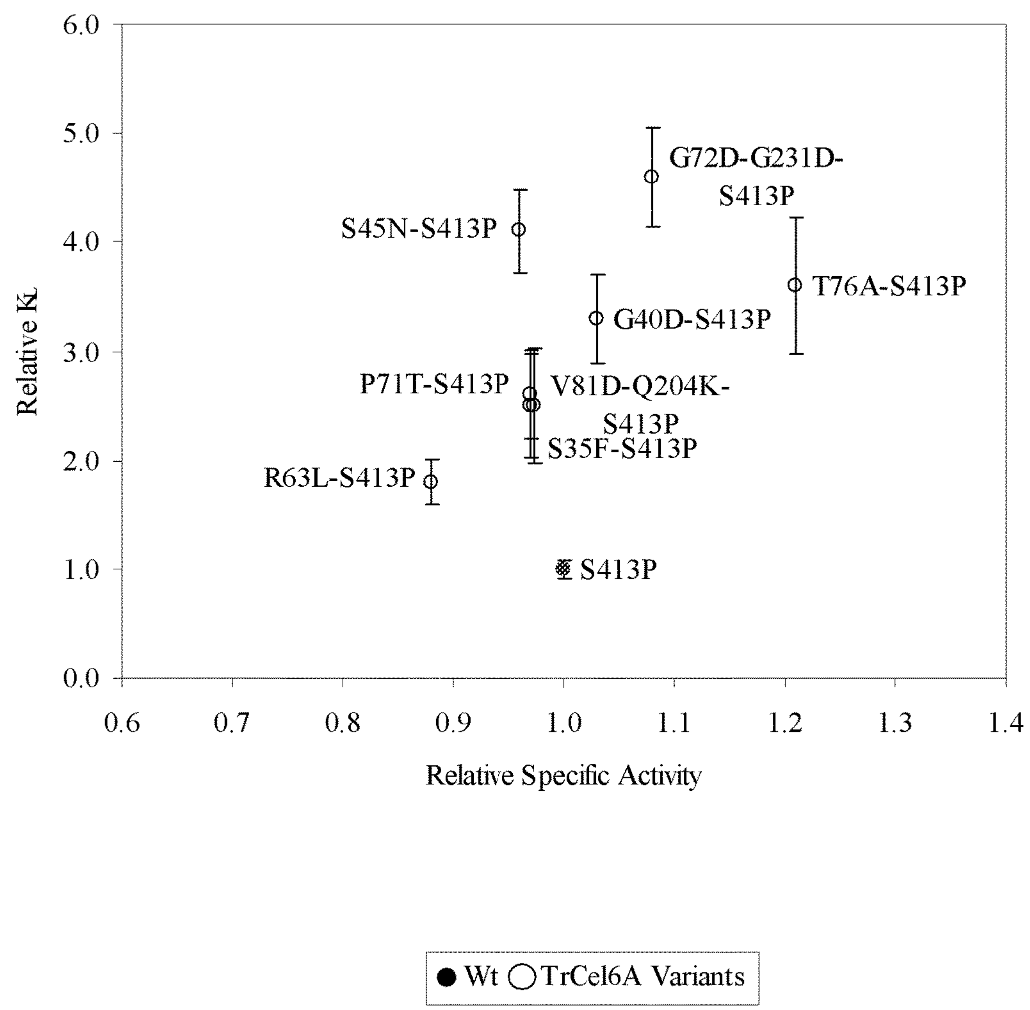
FIG. 4 is a scatter plot of relative lignin binding constants ($K_L$) and the relative specific activities of the lignin resistant TrCel6A variants and parental cellulase TrCel6A-S413P (Wt).

Glucose concentrations were converted to residual cellobiohydrolases (CBH) activity using a standard curve. Relative residual CBH activity was calculated by dividing the activity of a parental or modified CBH cellulase enzyme at t>0 hr by the activity of the corresponding CBH cellulase enzyme at t=0 hr. The relative residual CBH activity versus time data were modeled using Equation 1. A minimum of two replicate data sets for each parental and modified cellulase were fit to this model using a 4th order Runge-Kutta spreadsheet in Microsoft Excel. The $k_L$ value was fixed to 0.4 $hr^{-1}$ for all cellulases (parental and modified) and the model was fit to each data set by solving for $K_L$ using the method of least squares. A relative $K_L$ was calculated by dividing the $K_L$ for each modified CBH cellulase enzyme by the $K_L$ for the corresponding parental CBH cellulase enzyme. Therefore the relative $K_L$ for each parental CBH cellulase enzyme is 1.0. Standard errors of the cellulase activity measurements were calculated using a model comparison approach (Motulsky, H., and A. Christopoulos, 2004). A t-test was used to compare the relative $K_L$ value of each modified cellulase with that of its corresponding parental cellulase. P-values less than or equal to 0.05 were considered statistically significant. Modified cellulases with a relative $K_L$ significantly higher than that of the corresponding parental cellulase passed validation (Table 5 and FIG. 4).

$$E + L \overset{K_L}{\rightleftharpoons} EL \xrightarrow{k_L} EL^* \quad \text{Equation 1}$$

TABLE 5

Lignin binding constants ($K_L$) for lignin resistant TrCel6A variants.

| Mutation(s) | Relative $K_L$ | Standard Error | P-value | Relative Specific Activity |
|---|---|---|---|---|
| G72D, G231D | 4.6 | 0.45 | <0.001 | 1.08 |
| S45N | 4.1 | 0.38 | <0.001 | 0.96 |
| T76A | 3.6 | 0.63 | <0.001 | 1.21 |
| G40D | 3.3 | 0.41 | <0.001 | 1.03 |
| V81D, Q204K | 2.5 | 0.52 | <0.001 | 0.97 |
| R63L | 1.8 | 0.20 | <0.001 | 0.88 |
| S35F | 2.5 | 0.48 | 0.005 | 0.97 |
| P71T | 2.6 | 0.40 | <0.001 | 0.97 |
| Wt | 1.0 | 0.09 | — | 1.00 |

Example 10

Generating the Aggregate TrCel6A Variant

Based on some of the mutations identified during high-throughput screening (Example 6), an Aggregate TrCel6A Variant was designed:

Aggregate Cel6A Variant (S35F-G40D-S45N-R63L-P71T-G72D-T76A-V81D-S413P)

For the Aggregate TrCel6A Variant, the YEp352/PGK91-1-$\alpha_{ss}$-NKE TrCel6A-S413P vector was used as the template for a one step PCR reaction using QuikChange Lightning Site-Directed Mutagenesis kit from StrataGene. The Aggregate TrCel6A Variant was generated using the mutagenic primers PSP2 and PSP3. The final amplicon was transformed into yeast *Saccharomyces cerevisiae* strain BY4742 using the procedure of gap repair.

```
PSP2
                                             (SEQ ID NO: 60)
5'-CGTTGTGGGGGATACTCGAGAAGTCGTCGACGCGGCGCGCGTGGACG

AGTTTGAGCTTGCAGCATCGGGAAGACACTGAAAGTAATAGTCGTTGGAG

TA-3'

PSP3
                                             (SEQ ID NO: 61)
5'-CGAGTATCCCCCACAACGTCCCTGTCGAGCTCCGCGACGCCTCCAAC

TGATTCTACTACTGCTAGAGTACCTCCAGATGGATCGGGAACCGCTAC

G-3'
```

To perform gap repair, the vector YEp352/PGK91-1-$\alpha_{ss}$-NKE was digested with NheI and KpnI and purified on gel. *S. cerevisiae* strain BY4742 was used as the host. The digested YEp352/PGK91-1-$\alpha_{ss}$-NKE vector and the amplicons were transformed in yeast using the procedure described by Gietz, R. D. and Woods, R. A. (2002).

Example 11

Assaying the Aggregate TrCel6A Variant

Figure 5A:
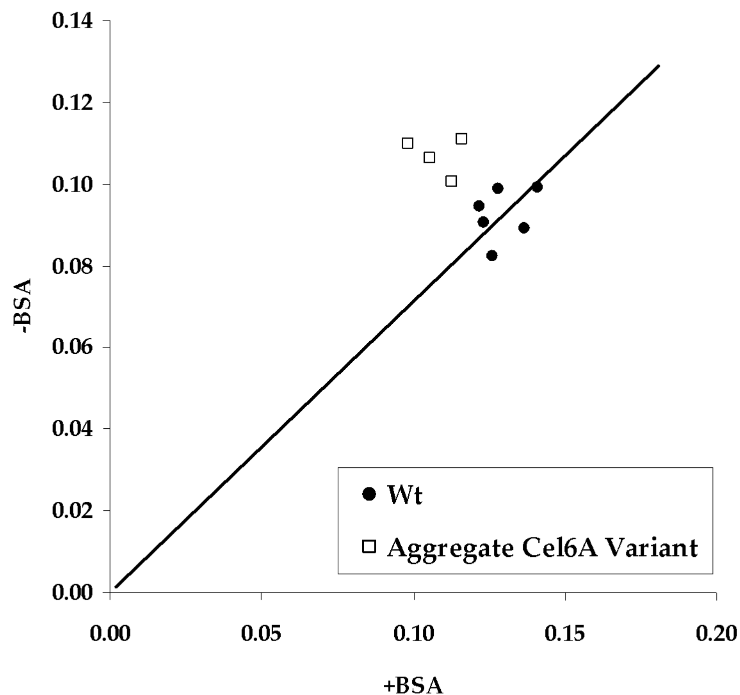
FIG. 5 contains two scatter plots "(A)" and "(B)". The data relate to the screening of the Aggregate TrCel6A Variant (TrCel6A-S35F-G40D-S45N-R63L-P71T-G72D-T76A-V81D-S413P) plus parental cellulase TrCel6A-S413P (Wt). Scatter plot (A) illustrates enzyme activity in the presence of BSA-treated lignin (+BSA) versus enzyme activity in the presence of untreated lignin (−BSA) for high-throughput Assay 1 (Example 6). Scatter plot (B) illustrates enzyme activity in the presence of BSA-treated lignin (+BSA) versus enzyme activity in the presence of untreated lignin (−BSA) for high-throughput Assay 2 (Example 7).
Figure 5B:
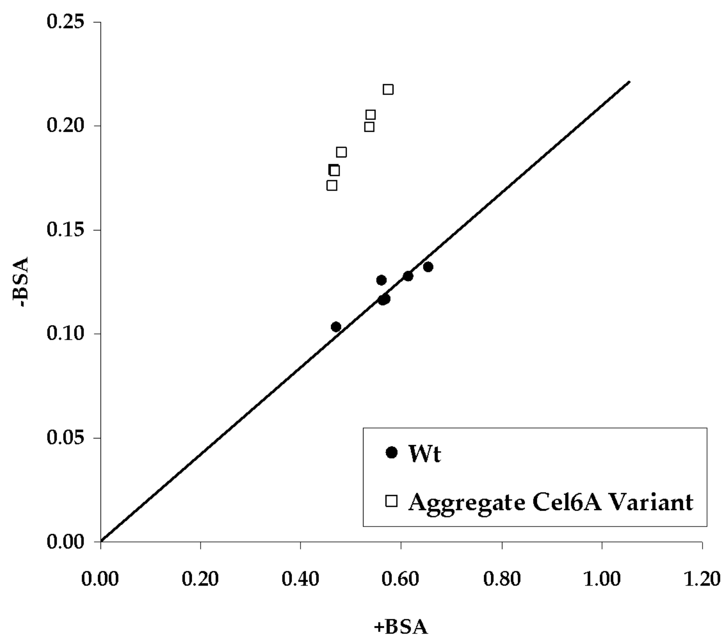

The Aggregate TrCel6A Variant (S35F-G40D-S45N-R63L-P71T-G72D-T76A-V81D-S413P) and the parental TrCel6A-S413P cellulase were expressed from yeast as described in Example 4. Aliquots of yeast filtrate, from both samples, were tested using both high-throughput screening assays (Examples 6 and 7). The ±BSA-lignin ratio was normalized to that of the parental TrCel6A-S413P cellulase and P-values were calculated for the Aggregate TrCel6A Variant (FIG. 5 and Table 6).

TABLE 6

| Normalized ±BSA-lignin ratios and P-value for the Aggregate TrCel6A Variant | | | | |
|---|---|---|---|---|
| | Assay 1 | | Assay 2 | |
| | Normalized ±BSA lignin ratio | P-value | Normalized ±BSA lignin ratio | P-value |
| TrCel6A-S413P | 1.00 | — | 1.00 | — |
| Aggregate TrCel6A Variant | 1.39 | <0.001 | 1.81 | <0.001 |

Figure 6:
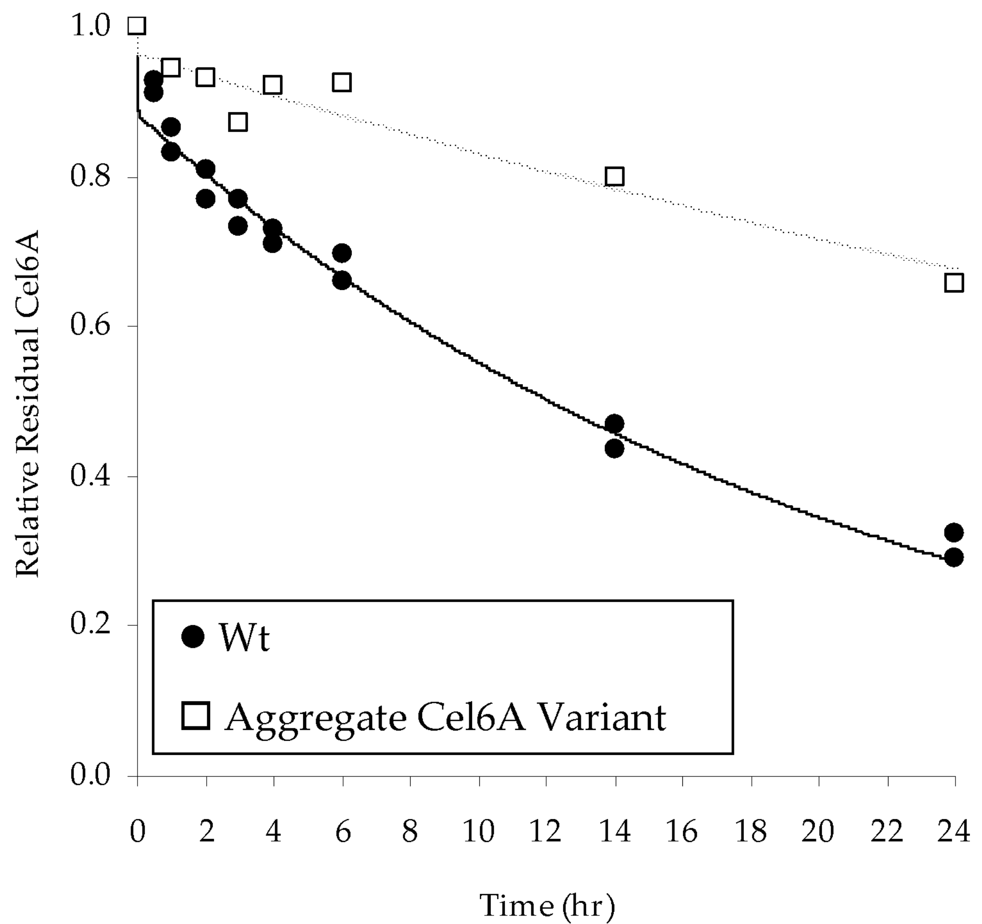
FIG. 6 is a graph of the lignin binding profiles of parental cellulase TrCel6A-S413P (TrCel6A$^{Wt}$) and the Aggregate TrCel6A Variant (TrCel6A-S35F-G40D-S45N-R63L-P71T-G72D-T76A-V81D-S413P).

The Aggregate TrCel6A Variant was further analyzed as described in Example 9. The results of this analysis are shown in Table 7 and in FIG. 6. In this case, the Aggregate TrCel6A Variant had a 3.9-fold higher $K_L$ compared to the parental TrCel6A-S413P cellulase.

TABLE 7

| Lignin binding constant of the Aggregate Cel6A Variant. | | | | |
|---|---|---|---|---|
| | Relative $K_L$ | Standard Error | P | Relative Specific Activity |
| TrCel6A$^{Wt}$ | 1.0 | 0.05 | — | 1.00 |
| Aggregate TrCel6AVariant | 3.9 | 0.78 | <0.001 | 1.01 |

Example 12

Generating Constructs Encoding Modified TrCel6A Cellulases with Novel Linker Sequences From the preceding examples, the inventors identified several mutations in the linker sequence of TrCel6A which conferred resistance to lignin binding. Therefore, the inventors conceived a broader strategy for altering the native linker sequence of TrCel6A, in a manner that reduces propensity for inactivation by lignin and can be applied to other cellulase enzymes.

A panel of Novel Linker Variants (FIG. 7) was generated. In one of these variants, TrCel6A$^{R\rightarrow E}$, arginines at amino acid 49, 56, 63 and 77 were substituted for glutamic acids. Two other variants contained deletions in the TrCel6A linker sequence. TrCel6A$^{\Delta 1}$ lacks amino acids 63-82 and TrCel6A$^{\Delta 2}$ has a deletion of amino acids 39-58. In the variant TrCel6A$^{S\rightarrow T}$, 13 serines in the linker (amino acids 43, 44, 45, 46, 47, 52, 55, 58, 62, 64, 65, 66 and 73) were changed to threonine. Finally, TrCel6A$^{R\rightarrow E/S\rightarrow T}$ contains the four arginine to glutamic acid mutations indicated above and the 13 serine to threonine mutations.

The Novel Linker Variants were generated using a two-step PCR method involving megaprimer synthesis followed by PCR-mediated overlap extension (Vallejo et al., 1994). All PCR reactions were carried out using the High Fidelity iProof Taq Polymerase (BioRad). Starting with YEp352/PGK91-1-$\alpha_{ss}$-Cel6A-S413P as the template, megaprimers upstream the mutagenesis site were amplified using external primer YαN21 with the internal reverse primer PSP16, 18, 24, and 28 to generate TrCel6A$^{\Delta 1}$, TrCel6A$^{\Delta 2}$, TrCel6A$^{R\rightarrow E}$, and TrCel6A$^{R\rightarrow E/S\rightarrow T}$, respectively. Megaprimers downstream the mutagenesis site were amplified with the external reverse primer PGKterm and the internal forward primer PSP17, 19, 25, and 29 to generate TrCel6A$^{\Delta 1}$, TrCel6A$^{\Delta 2}$, TrCel6A$^{R\rightarrow E}$, TrCel6A$^{S\rightarrow T}$ and TrCel6A$^{R\rightarrow E/S\rightarrow T}$, respectively. The internal primers were designed to introduce the desired mutations or truncations into the Novel Linker Variant constructs. The megaprimers were purified using the WIZARD® SV Gel and PCR Clean-Up System (Promega). Primer sequences are listed below:

```
YαN21
                                        (SEQ ID NO: 62)
5'AGC ACA AAT AAC GGG TTA TTG

PGKterm
                                        (SEQ ID NO: 63)
5'GCA ACA CCT GGC CCT TAC C

PSP16
                                        (SEQ ID NO: 64)
5'GGA TGT TGT GGG GGA TAC TCG AGA

PSP17
                                        (SEQ ID NO: 65)
5'TCT CGA GTA TCC CCC ACA ACA TCC TCG GGA ACC

GCT ACG

PSP18
                                        (SEQ ID NO: 66)
5'GGA GCT CGA CCG GGA TGT TGT GGG AAG ACA CTG
GGA GTA

PSP19
                                        (SEQ ID NO: 67)
5'CCC ACA ACA TCC CGG TCG AGC TCC

PSP24
                                        (SEQ ID NO: 68)
5'GGA CGT TGT GGG GGA TAC TTC AGA AGT CGT CGA

CGC GGC TTC CGT GGA CGA GCT TGA GCT

PSP25
                                        (SEQ ID NO: 69)
5'GTA TCC CCC ACA ACG TCC GAA TCG AGC TCC GCG

ACG CCT CCA CCT GGT TCT ACT ACT ACC GAA GTA

CCT CCA GTC GGA TCG

PSP28
                                        (SEQ ID NO: 70)
5'TTC AGT CGT TGT GGG AGT TAC TTC AGT AGT CGT

AGT CGC GGC TTC CGT AGT AGT AGT AGT AGT TGC

AGC GCC GGG AAG ACA

PSP29
                                        (SEQ ID NO: 71)
5'ACT CCC ACA ACG ACT GAA ACT ACT ACT GCG ACG

CCT CCA CCT GGT ACT ACT ACT ACC GAA GTA CCT

CCA GTC GGA TCG
```

In the second PCR, both megaprimers of a desired construct were allowed to anneal and extend for 10 cycles to generate the final template. The external primers YαN21 and PGKterm were then added for another 25 cycles to amplify the final product, which was subsequently purified using the WIZARD® SV Gel and PCR Clean-Up System. Both the purified PCR product and the linearized vector YEp352/PGK91-1$\alpha_{ss}$ (digested with NheI+KpnI) were transformed and cloned via in vivo recombination within the BY4742 yeast strain using the procedure described by Gietz, R. D. and Woods, R. A. (2002). For each construct, the vector was isolated from the transformed yeast using a method modified from Hoffman and Winston (1987) and transformed in *E. coli* DH5αchemically-competent cells. Plasmids were isolated from the *E. coli* cells using the WIZARD® Plus SV Minipreps DNA Purification System (Promega). The integrity of the cloned region of all variants was confirmed by DNA sequence analysis.

Example 13

Analysis of Novel Linker Variants in HTS Assay 2

Figure 8:
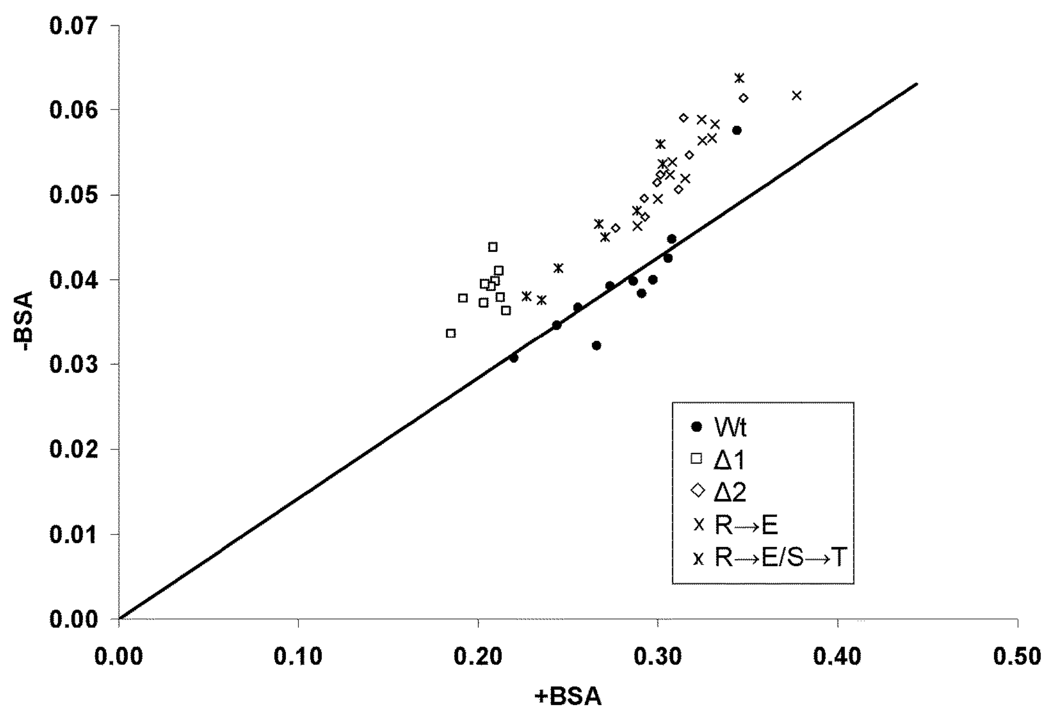
FIG. 8 is a scatter plot of enzyme activity in the presence of BSA-treated lignin (+BSA) versus enzyme activity in the presence of untreated lignin (−BSA) for high-throughput Assay 2. The data relate to the screening of the Novel Linker Variants (Δ1, Δ2, R→E, and R→E/S→T) plus parental cellulase TrCel6A-S413P (Wt). The Wt data were fit by linear regression in which the y-intercept was fixed to zero.

The Novel Linker Variants and the parental TrCel6A-S413P cellulase were expressed from *S. cerevisiae* as described in Example 4. Aliquots of yeast filtrate, from all samples, were tested using high-throughput screening Assay 2 (Example 7). The ±BSA-lignin ratio was normalized to that of the parental TrCel6A-S413P cellulase and P-values were calculated for the Novel Linker Variants (FIG. 8 and Table 8).

TABLE 8

Normalized ±BSA-lignin ratios and P-value for the Novel Linker Variants.

| Variant | Normalized ±BSA lignin ratio | P-value |
|---|---|---|
| TrCel6A-S413P | 1.00 | 1.00 |
| TrCel6A-Δ1-S413P | 1.34 | <0.001 |
| TrCel6A-Δ2-S413P | 1.22 | <0.001 |
| TrCel6A-$^{R \rightarrow E}$-S413P | 1.21 | <0.001 |
| TrCel6A-$^{R \rightarrow E/S \rightarrow T}$-S413P | 1.22 | <0.001 |

Example 14

Expression of Modified Cellulase Enzymes in *Trichoderma reesei*

14.1 Host *Trichoderma reesei* Strain Construction

The P297Jaux4 uridine auxotroph *Trichoderma reesei* strain was used for expression of modified TrCel6A and TrCel7A cellulases. This strain contains disruption of the cel7a, cel7b and cel6a genes and is deficient in production of TrCel7A, TrCel7B and TrCel6A cellulases.

The parent strain of P297Jaux, strain BTR213, is a derivative of RutC30 (ATCC #56765; Montenecourt and Eveleigh, 1979) produced by random mutagenesis and first selected for ability to produce larger clearing zones on minimal media agar containing 1% acid swollen cellulose and 4 g/L 2-deoxyglucose and then selected for the ability to grow on lactose media containing 0.2 μg/mL carbendazim. A uridine auxotroph of BTR213, BTR213aux, was obtained through selection of mutants spontaneously resistant to 0.15% w/v 5-fluoroorotic-acid (FOA).

Figure 14A:
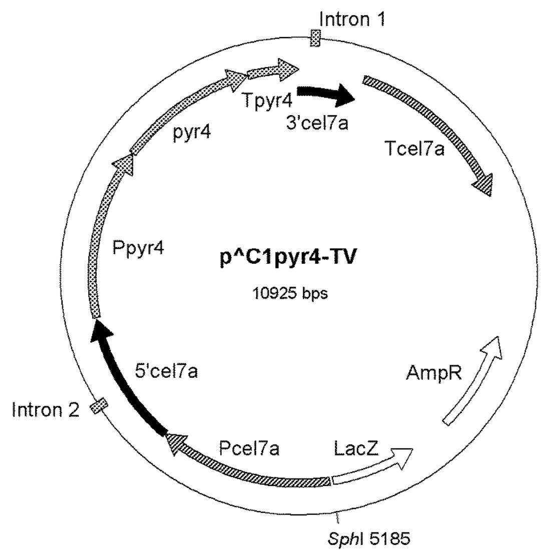
FIG. 14 shows maps of the vectors used to disrupt the cel7a (panel A), cel7b (panel B) and cel6a (panel C) genes in the *Trichoderma reesei* host strain P297J. The restriction sites used for linearization of transformation vectors are indicated on each vector map.
Figure 14B:
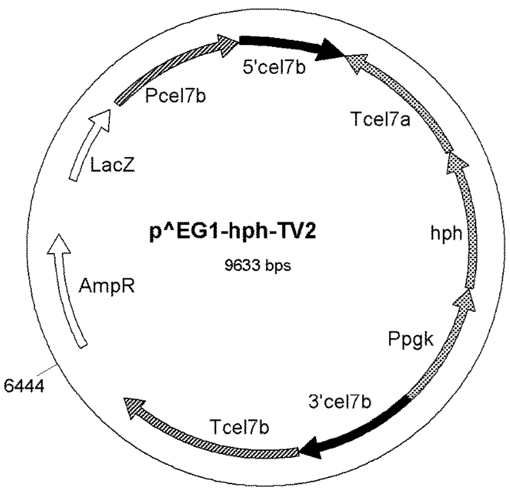
Figure 14C:
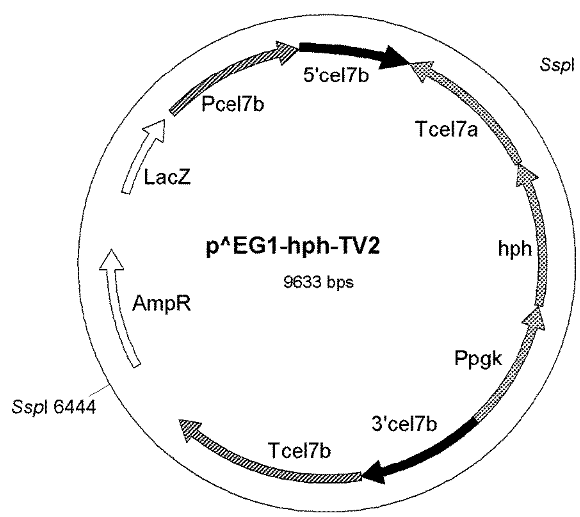

Strain P297J was generated by three consecutive steps of polyethylene glycol (PEG) mediated transformation (Example 14.3) of protoplasts and two steps of generation of uridine auxotrophs by plating on 5-FOA containing media. For deletion of the cel7a gene, a pyr4 auxotroph of strain BTR213 was transformed with p^C1pyr4-TV (FIG. 14A), a cel7a targeting vector containing the cel7a gene disrupted with a pyr4 selectable marker cassette. The isolated P54C strain possessing disruption of cel7a was then transformed with the cel7b targeting vector p^EG2-hph-TV2 containing cel7b gene disrupted with hph selectable marker cassette (FIG. 14B). The isolated P264F strain possessing disruption of both the cel7a and cel7b genes was plated on minimal media supplemented with 5 mM uridine and containing 0.15% w/v 5-FOA and uridine auxotroph P264Faux3 was isolated. Next P264Faux3 was transformed with p^C2pyr4-TV, a cel6a targeting vector containing cel6a gene disrupted with pyr4 selectable marker cassette (FIG. 14C). The resulting strain P297J, containing disruptions of the cel7a, cel7b and cel6a genes, was plated on minimal media supplemented with 5 mM of uridine and containing 0.15% w/v 5-FOA. The isolated P297Jaux4 strain is uridine auxotroph and does not produce Cel7A, Cel7B and Cel6A cellulases.

14.2 Constructs for the Expression of Modified Cellulases in *Trichoderma reesei*

Figure 1B:
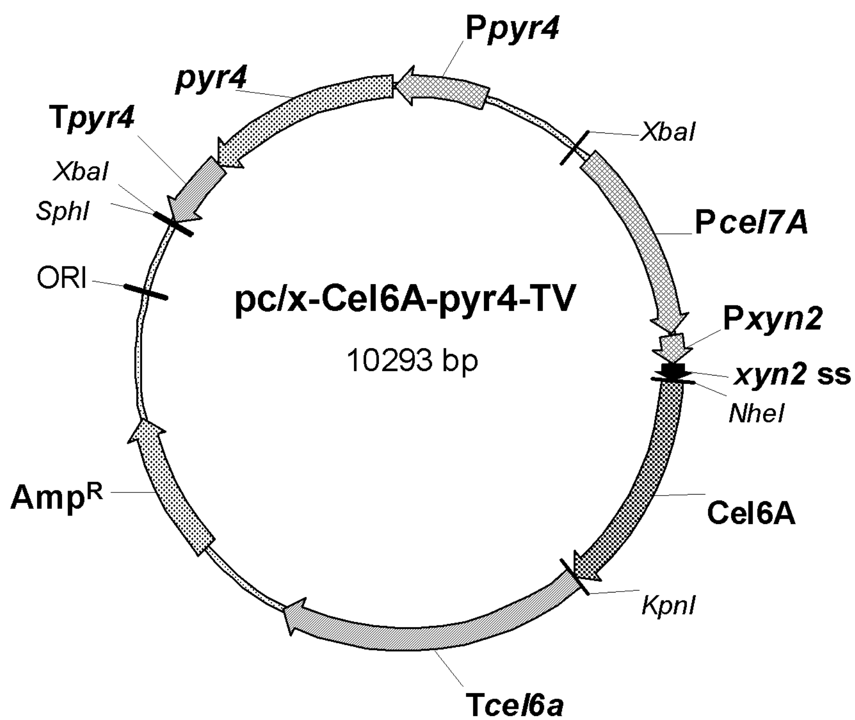

The yeast expression vectors possessing the Novel TrCel6A Linker Variants were digested with NheI and KpnI restriction enzymes. The DNA fragments were separated on agarose gels and the fragments corresponding to TrCel6A coding region were gel extracted using Wizard SV Gel and PCR clean-up System (Promega). The isolated fragments were ligated into NheI and KpnI restriction sites of *Trichoderma* transformation vector in frame with xyn2 secretion signal coding sequence, operably linked to a chimeric cel7A/xyn2 promoter (U.S. Pat. No. 6,015,703) and cel6a terminator (FIG. 1 B). The *N. crassa* pyr4 gene was used as selectable marker in *Trichoderma* transformation vector pc/x-Cel6A-pyr4-TV (FIG. 1 B). The TrCel6A coding region in the resulting transformation vectors was sequenced to verify presence of mutations in the linker peptide sequence. These constructs were transformed and cloned using chemically-competent DH5α *E. coli* cells to produce sufficient DNA for transformation into *Trichoderma*. The vectors encoding the Novel TrCel6A Linker Variants were used in subsequent transformation of *T. reesei* host strain P297Jaux (described above) by PEG transformation of protoplasts described in Example 14.3

Figure 15:
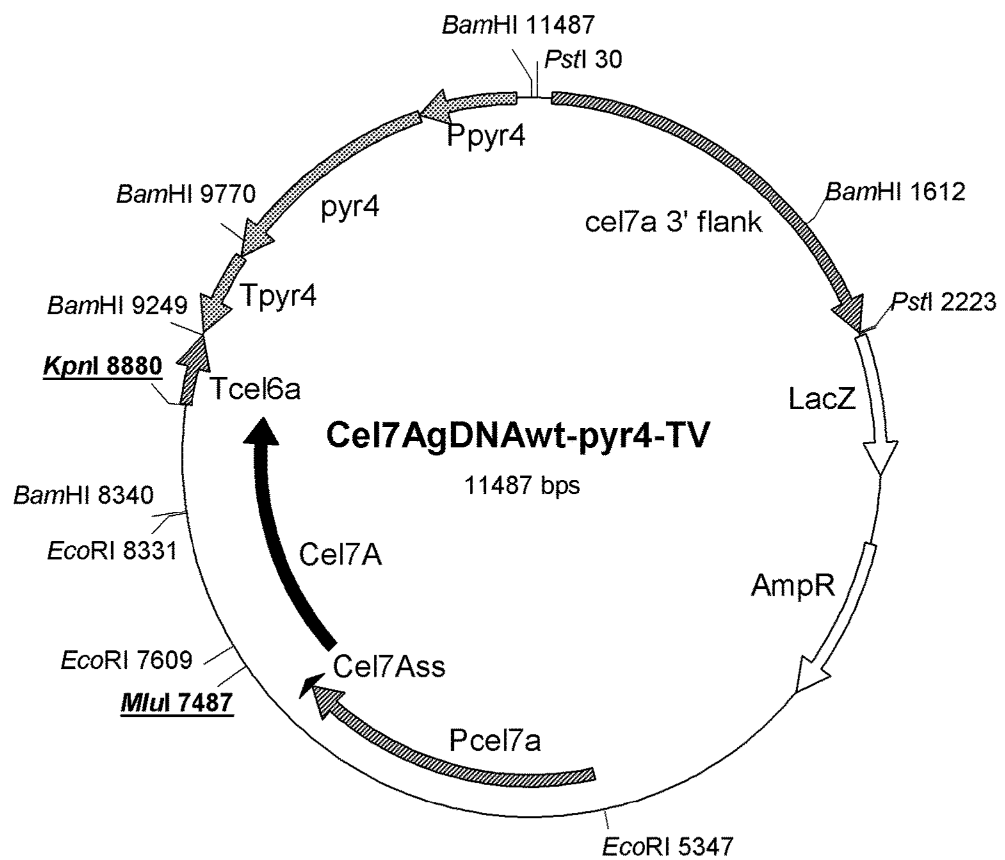
FIG. 15 shows the base vector used for the expression of parental and modified TrCel7A cellulases from *T. reesei* transformants. Restriction sites used for swapping of Cel7A variant coding sequences are indicated on the vector map in bold underlined font.

Vector pCel7AgDNAwt-pyr4-TV possessing pyr4 gene as selectable marker cassette and the wild type TrCel7A expression cassette was used as a backbone for cloning of modified TrCel7A cellulase encoding genes (FIG. 15). The selection cassette in this vector consists of the promoter, terminator, and coding sequence for orotidine-5'-phosphate decarboxylase (pyr4) from *Neurospora crassa* which allows complementation of uridine auxotrophy. The TrCel7A expression cassette consists of the native *T. reesei* cel7a promoter, cel7a coding region, and the *T. reesei* cel6a terminator sequences. The cel7a sequences were amplified as an entire fragment from *T. reesei* genomic DNA using primers FT011 and FT012 and the cel6a terminator sequence was amplified using primers KWO40 and KWO41 (Table 9). The vector pCel7AgDNAwt-pyr4-TV also contains ~2.2 kb of the *T. reesei* cel7a 3' end flanking sequence (amplified from *T. reesei* genomic DNA using primers KWO44 and KWO45) at the 5' end of selectable marker cassette (Table 9).

TABLE 9

Primers used for construction of modified Cel7A expression cassettes.

| Seq ID | Primer name | Primer sequence(5' > 3') |
|---|---|---|
| 72 | FT011 | CTGGGTACC TTACAGGCACTGAGAGTAGTAAGGG |
| 72 | FT012 | GTCGAATTCGTCTTCTCTAGGTGCCATTC |
| 74 | KW040 | CCTGTAAGGTACCCGGCTTTC |
| 75 | KW041 | CCCGTGGATCCTCATTCAAGC |
| 76 | KW044 | GTATTGGCTGCAGCGGCCCCACGGTCT |
| 77 | KW045 | GCCCGGCTGCAGAGCTCATGCGCAAAG |
| 78 | FT016 | GCCTGCACTCTCCAATCG |
| 79 | DK146 | GCTTCCAGTGGTAGTGGCTGGCTCCTCGGTGGTGGTGGTGCCAGGC |
| 80 | DK145 | GCCTGGCACCACCACCACCGAGGAGCCAGCCACTACCACTGGAAGC |
| 81 | DK148 | GTGAGACTGGGTAGGTCCGGGGGTGGTTCCAGTGGTAGTGGCTGGCT CCTCGGTGGTGGTGGTGCCAGGC |
| 82 | DK147 | GCCTGGCACCACCACCACCGAGGAGCCAGCCACTACCACTGGAACCA CCCCCGGACCTACCCAGTCTCAC |

Using pCel7AgDNAwt-pyr4-TV as a template, mutations in Cel7A linker coding sequence were introduced by a two-step PCR method involving megaprimer synthesis followed by megaprimer PCR (Table 10). The internal primers were modified to introduce the desired amino acid substitutions into the Cel7A coding region. The external plasmid primers (FT016 and FT011) were used to amplify the final product. Megaprimers and final products were purified using the WIZARD® SV Gel and PCR Clean-Up System.

TABLE 10

Mega primer PCR strategy used for site-directed mutagenesis of cel7a

| PCR | Step | Template | Primer 1 | Primer 2 | Amplicon |
|---|---|---|---|---|---|
| 1 | 1 | pCel7AgDNAwt-pyr4-TV | FT016 | DK146 | PCR 1 Step 1 |
| | 1 | pCel7AgDNAwt-pyr4-TV | DK145 | FT011 | PCR 1 Step 1 |
| | 2 | Both PCR 1 Step 1 megaprimers | FT016 | FT011 | Cel7A-LR017 (Cel7A-R449E-R450E) |
| 2 | 1 | pCel7AgDNAwt-pyr4-TV | FT016 | DK148 | PCR 2 Step 1 |
| | 1 | pCel7AgDNAwt-pyr4-TV | DK147 | FT011 | PCR 2 Step 1 |
| | 2 | Both PCR 2 Step 1 megaprimers | FT016 | FT011 | Cel7A-LR018 (Cel7A-R449E-R450E-S457T-S458T) |

The final PCR products, Cel7A-LR017 and Cel7A-LR018, were digested with MluI and KpnI restriction enzymes and ligated into backbone of vector pCel7AgDNAwt-pyr4-TV linearized with MluI and KpnI generating vectors pCel7A-LR017-pyr4-TV and pCel7A-LR018-pyr4-TV, respectively. The ligation mix was transformed into DH5α chemically-competent *E. coli* cells, plasmid extracted, and presence of introduced mutations was verified by sequencing. These vectors (pCel7A-LR017-pyr4-TV and pCel7A-LR018-pyr4-TV) were used in subsequent transformation of *T. reesei* host strain P297Jaux (described above) by biolistic transformation method described in Example 14.4.

14.3 PEG Transformation of *Trichoderma reesei* Protoplasts

5×10$^6$ spores of the appropriate host strain were plated onto sterile cellophane on Potato Dextrose agar supplemented with 5 mM uridine and were incubated for 20 hours at 30° C. to facilitate spore germination and mycelial growth. Cellophane discs with mycelia were transferred to 10 mL of a protoplasting solution containing 7.5 g/L Driselase and 4 g/L beta-glucanase (InterSpex Products Inc., Cat. Nos. 0465-1 and 0439-2, respectively) in 50 mM potassium phosphate buffer, pH 6.5 containing 0.6 M ammonium sulfate (Buffer P). The mycelial mat was digested for 5 hours with shaking at 60 rpm. Protoplasts were separated from undigested mycelia by filtration through sterile No. 30 MIRACLOTH™ and collected into a sterile 50 mL round-bottom centrifuge tube and recovered by centrifugation at 1000-1500×g for 10 min at room temperature. Protoplasts were washed with 5 mL of Buffer P and centrifuged again at 1000-1500×g for 10 min at room temperature. Protoplasts were resuspended in 1 mL of STC buffer (1.2 M sorbitol, 10 mM $CaCl_2$, 10 mM Tris-HCL, pH 7.5). For transformation, 0.1 mL of resuspended protoplasts were combined with 10 μg of vector DNA and 25 μL of PEG solution (25% PEG 3350, 50 mM $CaCl_2$, 10 mM Tris-HCl, pH 7.5). After incubation in an ice water bath for 30 min, 1 mL of PEG solution was added and the mixture incubated for 5 min at room temperature. Transformation mix was diluted with 2 mL of STC buffer and the entire mix was added to 50 mL of molten MMSS agar media (see below) cooled to about 47°

C., split in half, and poured over MMSS agar. Plates were incubated at 30° C. until colony growth was visible. Transformants were transferred to individual plates containing MM agar and allowed to sporulate. Spores were collected and plated at high dilution on MM agar to isolate homokaryon transformants, which were then plated onto PDA to allow for growth and sufficient sporulation to inoculate the screening cultures described below.

Minimal medium (MM) agar contains:

| Component* | Per L |
|---|---|
| $KH_2PO_4$ | 10 g |
| $(NH_4)_2SO_4$ | 6 g |
| $Na_3Citrate•2H_2O$ | 3 g |
| $FeSO_4•7H_2O$ | 5 mg |
| $MnSO_4•H_2O$ | 1.6 mg |
| $ZnSO_4•7H_2O$ | 1.4 mg |
| $CaCl_2•2H_2O$ | 2 mg |
| Agar | 20 g |
| 20% Glucose f.s. | 50 mL |
| 1M MgSO4—$7H_2O$ f.s. | 4 mL |
| | pH to 5.5 |

*MMSS agar contains the same components as MM agar plus 1.2M sorbitol, 6.6 g/L YNB (Yeast Nitrogen Base w/o Amino Acids from DIFCO Cat. No. 291940) and 1.92 g/L amino acids (-Ura DO Supplement from Sigma Cat. No. Y1501-20G).

14.4 Biolistic Transformation of *Trichoderma reesei* Spores

To generate strains expressing modified TrCel7A proteins, vectors pCel7A-LR017-pyr4-TV and pCel7A-LR018-pyr4-TV were transformed into a P297Jaux4 by biolistic gold particle bombardment using PDS-1000/He system (BioRad; E.I. DuPont de Nemours and Company). Gold particles (median diameter of 0.6 μm, BioRad Cat. No. 1652262) were used as microcarriers. The following parameters were used for the transformation: a rupture pressure of 1350 psi, a helium pressure of 29 mm Hg, a gap distance of 0.6 cm, a macrocarrier travel distance of 16 mm, and a target distance of 6 cm. The spore suspension was prepared by washing *T. reesei* spores from the PDA plates incubated for 4-5 days at 30° C. with sterile water. About $1\times10^7$ washed spores were plated on 60 mm diameter plates containing MM agar lacking uridine. After particle delivery all transformation plates were incubated at 30° C. for 5-10 days. Isolated transformants were transferred to secondary selective media plates and then to PDA plates to allow for growth and sufficient sporulation to inoculate the microcultures.

14.5 Production of Modified Cellulases in *Trichoderma reesei* Microcultures

Individual colonies of *Trichoderma* were transferred to PDA plates for the propagation of each culture. Sporulation was necessary for the uniform inoculation micro-cultures which were used in testing the ability of the culture to produce cellulase. The culture media was composed of the following:

| Component | g/L |
|---|---|
| $(NH_4)_2SO_4$ | 12.7 |
| $KH_2PO_4$ | 8.00 |
| $MgSO_4•7H_2O$ | 4.00 |
| $CaCl_2•2H_2O$ | 1.02 |
| CSL | 5.00 |
| $CaCO_3$ | 20.00 |
| Carbon source** | 30-35 |
| Trace elements* | 2 mL/L |

*Trace elements solution contains 5 g/L $FeSO_4*7H_20$; 1.6 g/L $MnSO_4*H_20$; 1.4 g/L1 $ZnSO_4*7H_20$.
**glucose, Solka floc, lactose, cellobiose, sophorose, corn syrup, or Avicel. The carbon source can be sterilized separately as an aqueous solution at pH 2 to 7 and added to the remaining media initially or through the course of the fermentation.

Individual transformants were grown in the above media in 1 mL cultures in 24-well micro-plates. The initial pH was 5.5 and the media sterilized by steam autoclave for 30 minutes at 121° C. prior to inoculation. For both native and transformed cells, spores were isolated from the PDA plates, suspended in water and $10^4$-$10^6$ spores per mL are used to inoculate each culture. The cultures were shaken at 250 rpm at a temperature of 30° C. for a period of 6 days. The biomass was separated from the filtrate containing the secreted protein by centrifugation at 12000 rpm. The protein concentration was determined using the Bio-Rad Protein Assay (Cat. No. 500-0001).

The relative abundance (in weight % of total secreted protein) of TrCel7A or TrCel6A in the microculture filtrates was determined by ELISA. Culture supernatants and purified component standards were diluted to 0.01-10 μg/mL in phosphate-buffered saline, pH 7.2 (PBS) and incubated overnight at 4° C. in microtitre plates (Costar EIA #9018). These plates were washed with PBS containing 0.1% Tween-20 (PBS/Tween) and then incubated in PBS containing 1% bovine serum albumin (PBS/BSA) for 1 hr at room temperature. Blocked microtitre wells were washed with PBS/Tween. Rabbit polyclonal antisera specific for TrCel6A or TrCel7A was diluted in PBS/BSA, added to separate microtitre plates and incubated for 2 hrs at room temperature. Plates were washed and incubated with a goat anti-rabbit antibody coupled to horseradish peroxidase (Sigma #A6154), diluted 1/2000 in PBS/BSA, for 1 hr at room temperature. After washing, tetramethylbenzidine was added to each plate and incubated for 30 min at room temperature. The absorbance at 360 nm was measured in each well and converted into protein concentration using a TrCel6A or TrCel7A standard curve.

Figure 16:
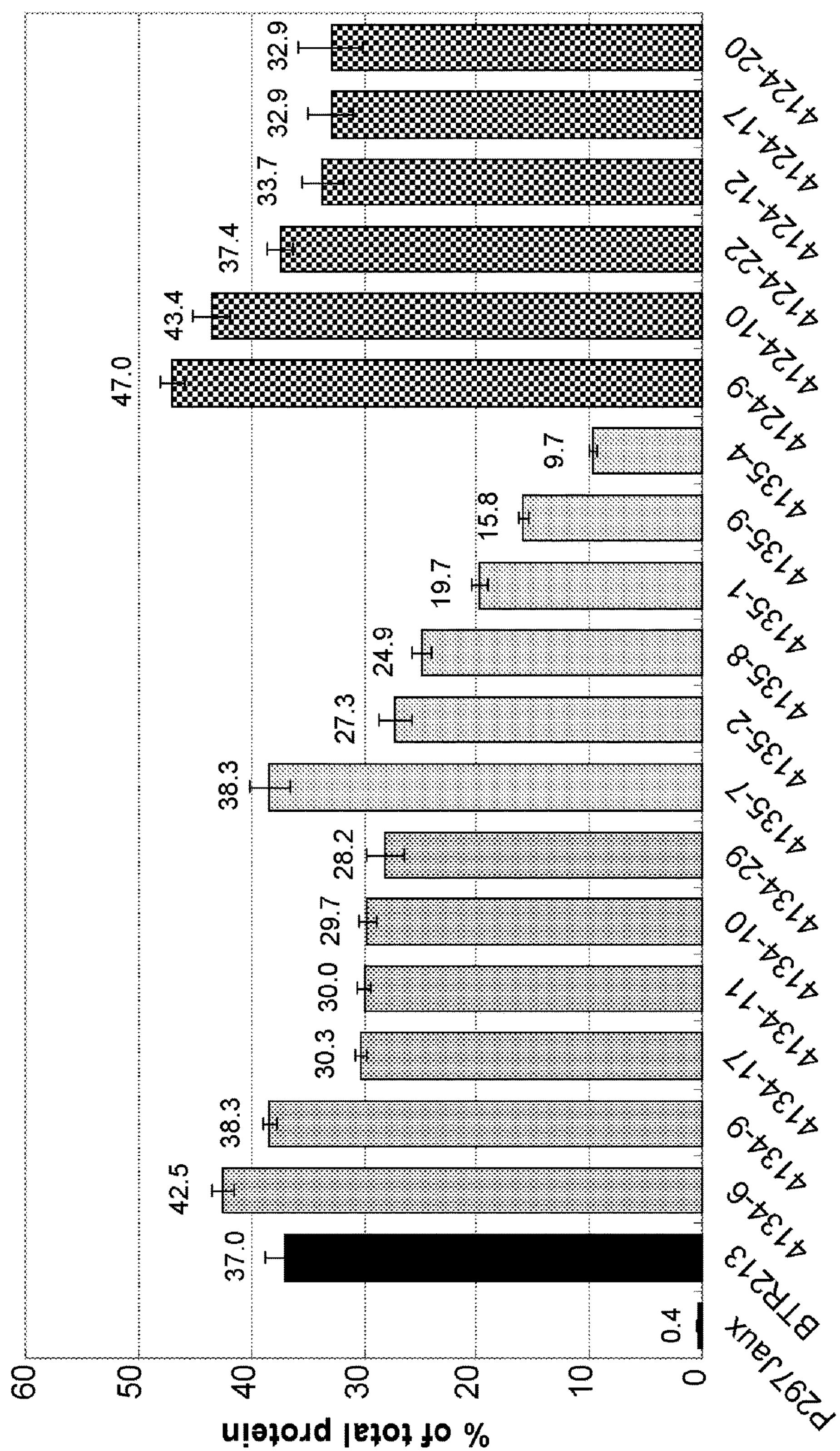
FIG. 16 shows the TrCel7A content (in % of total protein) of microculture filtrates produced by strains BTR213, P297Jaux and transformant strains expressing modified or wild type TrCel7A cellulases. Black bars—parental P297Jaux strain with disrupted cel7a gene and BTR213, parental strain of P297Jaux4. Grey bars—P297Jaux4 transformants expressing TrCel7A-LR017. Striped bars—P297Jaux4 transformants expressing TrCel7A-LR018. Checked bars—P297Jaux4 transformants expressing wild type TrCel7A.

Strains P667A (expressing TrCel6A-Δ1-S413P), P668D (expressing TrCel6A-Δ2-S413P), P671B (expressing TrCel6A-$^{R\rightarrow E}$-S143P) and P673B (expressing TrCel6A-$^{R\rightarrow E/S\rightarrow T}$-S143P) were selected for further analysis as they produce highest amounts of Cel6A protein. Strains 4124-9 (expressing wild type Cel7A), 4134-6 (expressing Cel7A-LR017) and 4135-7 (expressing Cel7A-LR018) were selected for further analysis as they produce highest amounts of Cel7A protein. The cel7a gene was amplified by PCR using genomic DNA isolated from all three selected transformants and the presence of modifications was confirmed by sequencing. The concentration of TrCel7A in the microculture filtrates (expressed as the mass percent of the component as a fraction of total secreted protein) is shown in FIG. 16.

14.6 Production of Modified Cellulases in 14 L *Trichoderma reesei* Fermentations For purification and characterization of modified cellulases, the selected transformants expressing modified TrCel6A or TrCel7A cellulases were grown in 14 L pilot fermentation. *T. reesei* strains were grown on Potato Dextrose Agar at 28-30° C. until a confluent lawn of spores was obtained. Spores were collected and used to inoculate 750 ml of Berkeley media (10 g/l glucose, 1.4 g/L $(NH_4)_2SO_4$, 2.0 g/L $KH_2PO_4$, 0.31 g/L $MgSO_4.7H_2O$, 0.53 g/L $CaCl_2$, 5.1 g/L dry corn steep, 5 mg/L $FeSO_4.7H_2O$, 0.8 mg/L $MnSO_4.H_2O$, 0.7 mg/L $ZnSO_4.7H_2O$) in a 2 L baffled flask.

After 3 days of growth at 28° C. and 150 rpm, this culture was used to inoculate 10 L of fermentation medium with the following initial composition: 13 g/L glucose, 2.2 g/L $(NH_4)_2SO_4$, 1.39 g/L $KH_2PO_4$, 0.7 g/l $MgSO_4.7H_2O$, 0.185 g/L $CaCl_2$, 6 g/l dry corn steep, 1.75 mg/L $FeSO_4.7H_2O$, 0.56 mg/L $MnSO_4.H_2O$, 0.49 g/L $ZnSO_4.7H_2O$. The vessel was run in batch mode until glucose in the media was depleted. At this point, the carbon source containing cellulase inducing carbohydrates was added, on a continuous basis, from a stock that was 35.5% w/v of solids dissolved in water. Peristaltic pumps were used to deliver the carbon source at a feed at a rate of 0.4 grams of carbon per liter culture per hour. Operational parameters during both the batch and fed-batch portions of the run were: mixing by impeller agitation at 500 rpm, air sparging at 8 standard liters per minute, and a temperature of 28° C. Culture pH was maintained at 4.0-4.5 during batch growth and pH 3.5 during cellulase production using an automated controller connected to an online pH probe and a pump enabling the addition of a 10% ammonium hydroxide solution. Periodically, 100 mL samples of broth were drawn for biomass and protein analysis.

The biomass content of the culture broth was determined using aliquots of 5-10 mL that had been weighed, vacuum filtered through glass microfiber filters, and oven dried at 100° C. for 4 to 24 hours. The concentration of biomass was determined according to the equation below.

$$\text{Biomass(g/L)} = \frac{\text{dry filter paper and cake (g)} - \text{filter mass (g)}}{\text{wet sample mass (g)}} \times \text{broth density (g/mL)} \times 1000\ \text{(mL/L)}$$

The protein concentration of culture filtrate was determined using the Bradford assay. Colour intensity changes in the Coomassie Brilliant Blue G-250 dye, that forms the basis of this assay, were quantified spectrophotometrically using absorbance measurements at 595 nm. The standard assay control used was a cellulase mixture of known composition and concentration. The final filtrates for enzyme analysis were collected after 162-170 hours.

Figure 11:
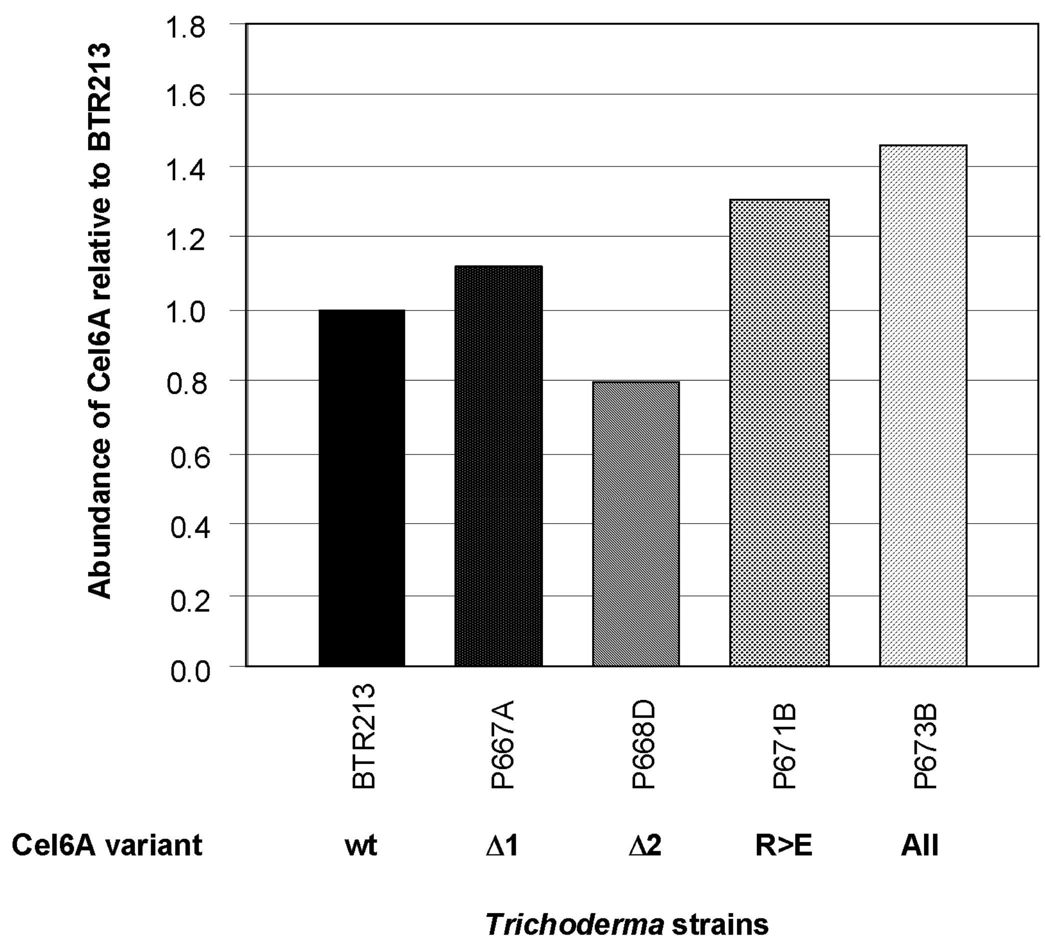
FIG. 11 shows the relative abundance of TrCel6A (from strain BTR213) and Novel TrCel6A Linker Variants (from strains P667A, P668D, P671B and P673B) produced in micro-culture with cellulase inducing carbohydrates, as detected by immunoassay using TrCel6A-specific polyclonal antibodies.

The concentration of parental or modified TrCel6A cellulases in the filtrates from the *Trichoderma reesei* 14 L fermentation cultures was determined by ELISA as describe above and the results are shown in FIG. 11.

Example 15

Assaying the Modified Cellulases Expressed from *Trichoderma*

Figure 10A:
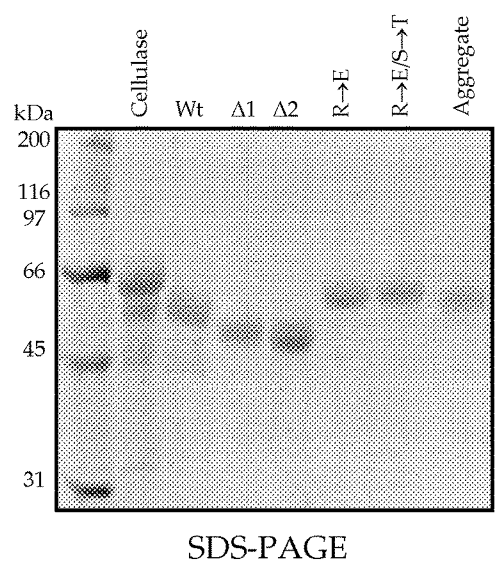
FIG. 10 shows SDS- (panel A) and IEF-PAGE (panel B) gels of the purified TrCel6A parental and modified cellulases expressed from *Trichoderma.*
Figure 10B:
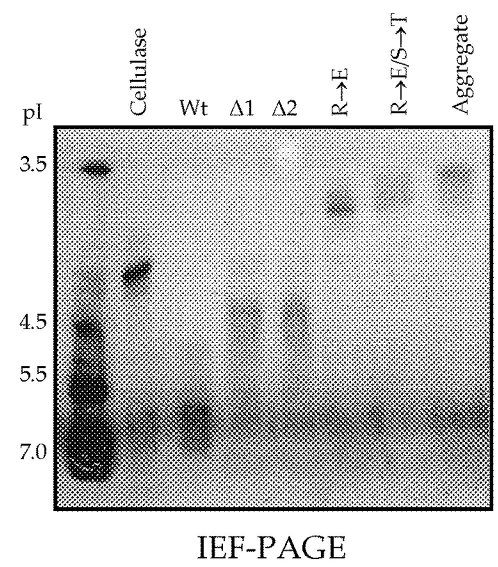

The cellulase protein collected from the filtrate of each of the fermentation broths described in Example 14.6 was separated by anion exchange chromatography using a DEAE-Sepharose column as described by Bhikhabhai et al. (1984). Each of the parental or modified TrCel6A cellulases was then further purified by p-aminophenyl-1-thio-beta-D-cellobioside affinity chromatography as reported by Piyachomkwan et al. (1997, 1998). The purified TrCel6A cellulases were concentrated and buffer exchanged into 50 mM sodium citrate, pH 5.0 using a stirred ultrafiltration cell (Amicon) and a 10 kDa NMWL polyethersulfone membrane. Protein concentrations were determined chemically using the method of Bradford et al. (1976). Samples of each purified protein were separated by SDS- and IEF-PAGE and visualized post-electrophoretically by Coomassie Blue staining as shown in FIG. 10.

Figure 9A:
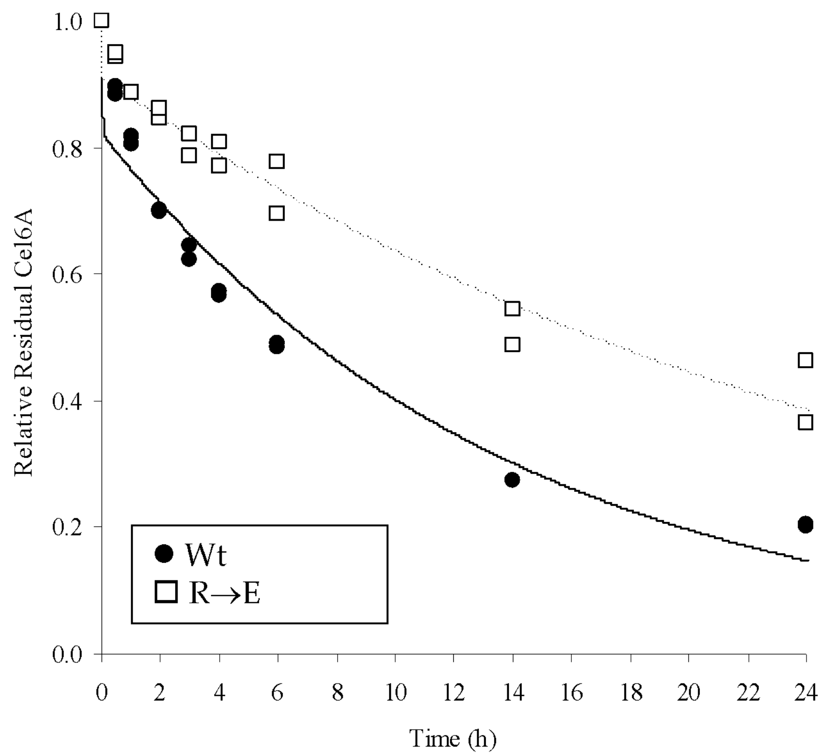
FIG. 9 shows the lignin binding profiles of the TrCel6A$^{R \rightarrow E}$ and TrCel6A$^{R \rightarrow E/S \rightarrow T}$ linker variants vs. the lignin binding profile of parental cellulase TrCel6A-S413P (Wt).
Figure 9B:
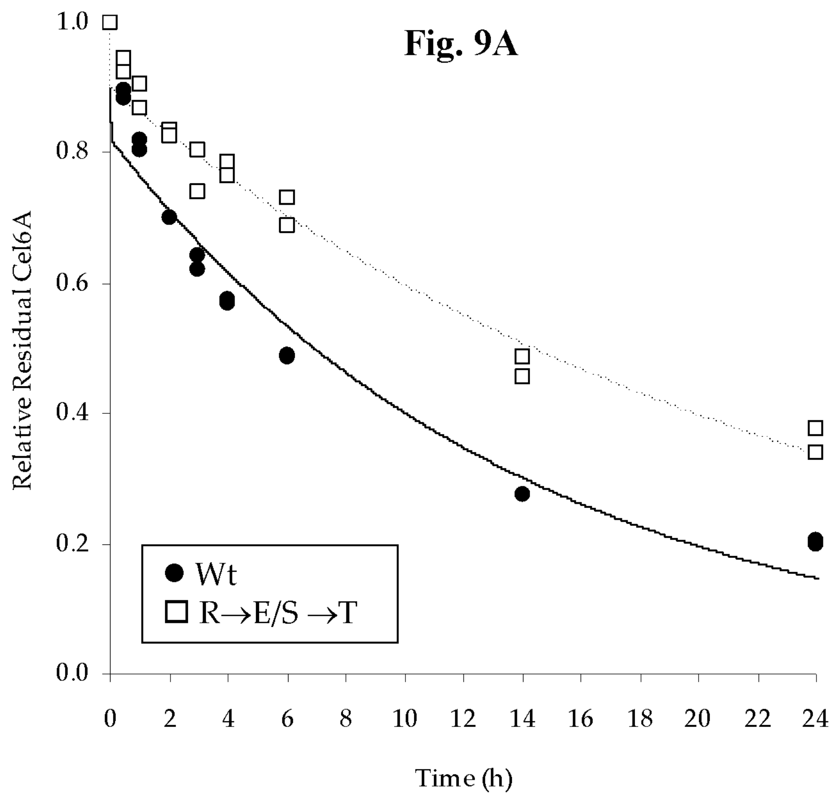

The Novel Linker Variants secreted from *Trichoderma* were assayed for lignin resistance as described in Example 9. The results are shown in Table 11 and FIG. 9. The TrCel6A$^{R\rightarrow E}$ and the TrCel6A$^{R\rightarrow E/S\rightarrow T}$ cellulases exhibited 2.4 and 2.2-fold higher $K_L$ values compared to the TrCel6A$^{Wt}$ control. The TrCel6A$^{\Delta 1}$ cellulase had a more modest, but significant, improvement in lignin resistance.

TABLE 11

Relative $K_L$ values of Novel Cel6A Linker Variants

| TrCel6A variant | Linker Peptide Sequence | Relative $K_L$ | Standard Error | P-value | Relative Specific Activity |
|---|---|---|---|---|---|
| TrCel6A$^{Wt}$ | PGAASSSSSTRAASTTSRVSPT TSRSSSATPPPGSTTTRVPPVG (SEQ ID NO: 9) | 1.0 | 0.06 | — | 1.00 |
| TrCel6A$^{\Delta 1}$ | PGAASSSSSTRAASTTSRVSPT TS (SEQ ID NO: 35) | 1.2 | 0.09 | 0.03 | 0.82 |
| TrCel6A$^{\Delta 2}$ | PTTSRSSSATPPPGSTTTRVPP VG (SEQ ID NO: 36) | 1.1 | 0.06 | 0.85 | 0.87 |
| TrCel6A$^{R\rightarrow E}$ | PGAASSSSST**E**AASTTS**E**VSPT TS**E**SSSATPPPGSTTT**E**VPPVG (SEQ ID NO: 33) | 2.4 | 0.14 | <0.001 | 0.86 |
| TrCel6A$^{R\rightarrow E/S\rightarrow T}$ | PGAA**TTTTTTE**AA**T**TTT**E**V**T** PTTT**ETTT**ATPPPG**T**TTT**E**VP PVG (SEQ ID NO: 38) | 2.2 | 0.13 | <0.001 | 0.86 |

Example 16

Assaying the Modified TrCel7A Cellulases Expressed from *Trichoderma*

Figure 13:
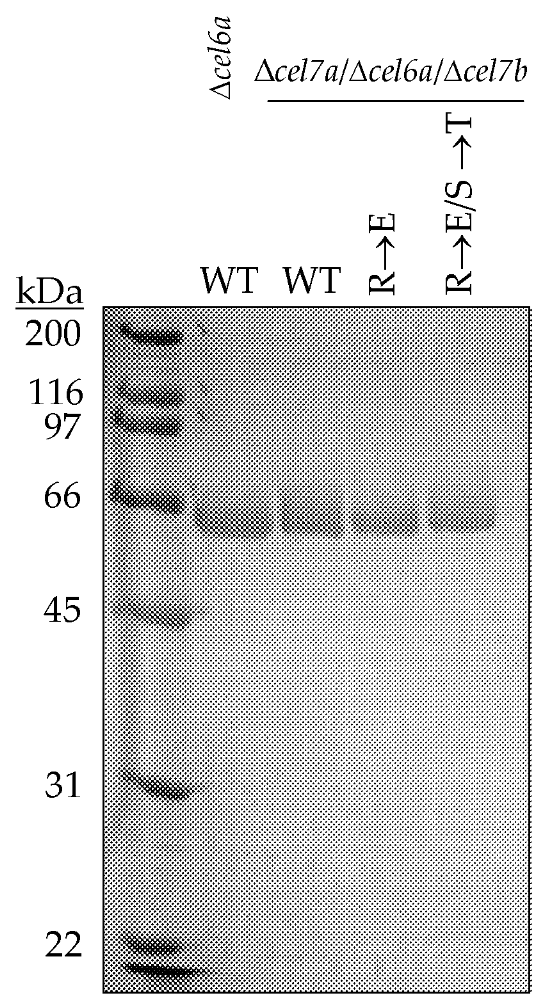
FIG. 13 shows an SDS-PAGE gel of the purified TrCel7A variant proteins expressed from *Trichoderma.*

The cellulase protein collected from the filtrate of each of the fermentation broths described in Example 14 was separated by anion exchange chromatography using a DEAE-Sepharose column as described by Bhikhabhai et al. (1984). Each of the TrCel7A variants was then further purified by p-aminophenyl-1-thio-β-D-cellobioside affinity chromatography as reported by Piyachomkwan et al. (1997, 1998). The purified Cel7As were concentrated and buffer exchanged into 50 mM sodium citrate, pH 5.0 using a stirred ultrafiltration cell (Amicon) and a 10 kDa NMWL polyethersulfone membrane. Protein concentrations were determined chemically using the method of Bradford et al. (1976). Samples of each purified TrCel7A protein were separated by SDS-PAGE and visualized post-electrophoretically by Coomassie Blue staining as shown in FIG. 13.

Figure 12A:
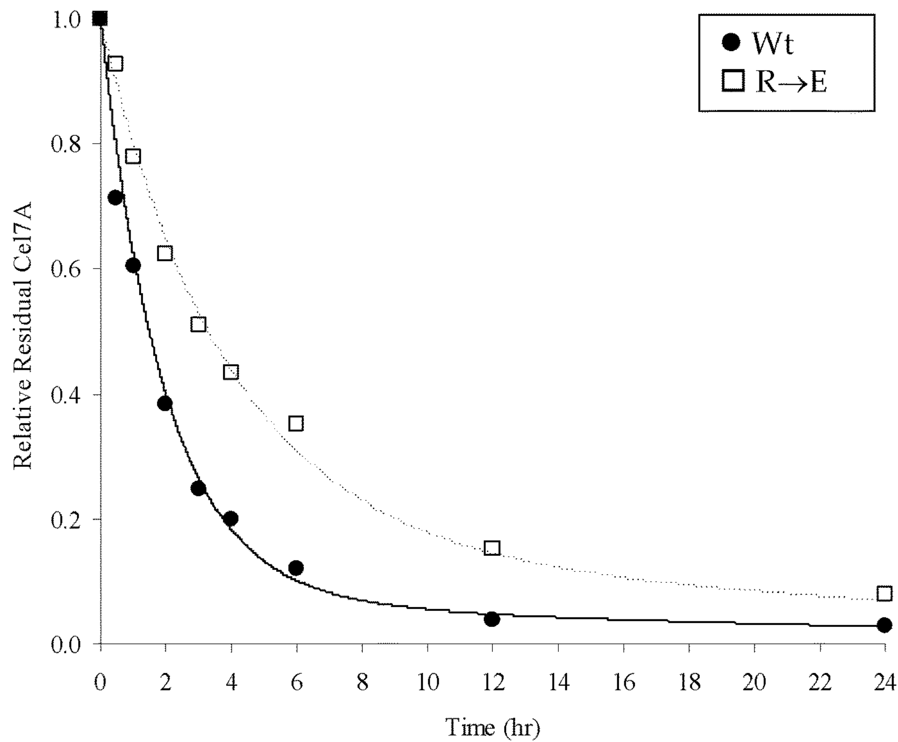
FIG. 12 shows the lignin binding profiles of the TrCel7A$^{R \rightarrow E}$ and TrCel7A$^{R \rightarrow E/S \rightarrow T}$ linker variants vs the lignin binding profile of parental cellulase TrCel7A (Wt).
Figure 12B:
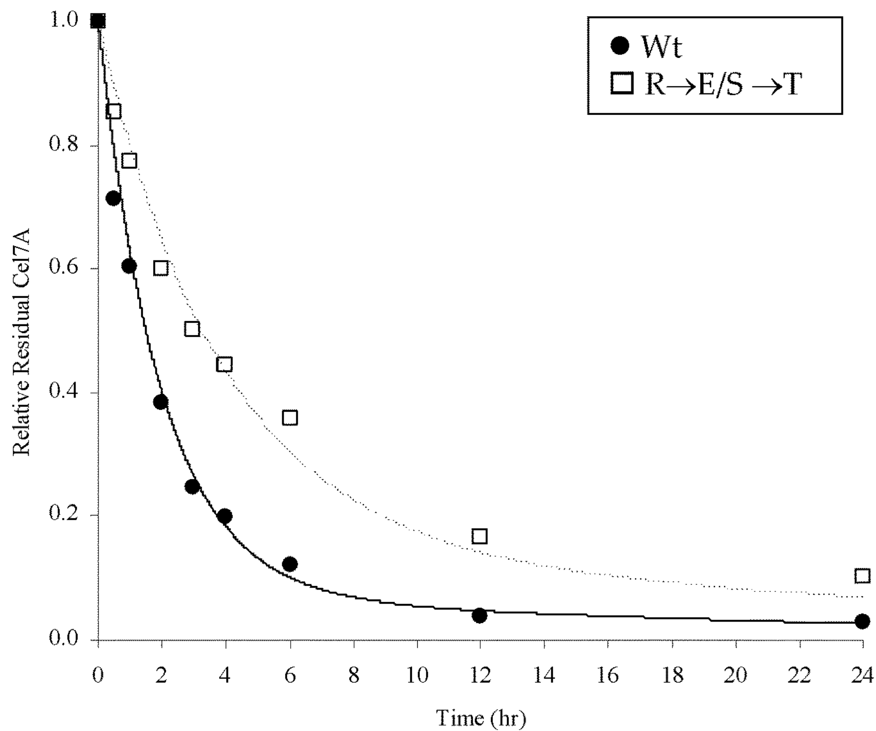

The TrCel7A$^{R\rightarrow E}$ and TrCel7A$^{R\rightarrow E/S\rightarrow T}$ secreted from *Trichoderma* were assayed for lignin resistance as described in Example 9. The results are shown in Table 12 and FIG. 12. The TrCel7A$^{R\rightarrow E}$ and the TrCel7A$^{R\rightarrow E/S\rightarrow T}$ mutants had 2.2 and 2.1-fold higher $K_L$ values compared to the TrCel7A$^{Wt}$ control.

TABLE 12

Relative $K_L$ values of TrCel7A Linker Variants

| TrCel6A variant | Linker Peptide Sequence | Relative $K_L$ | Standard Error | P-value | Relative Specific Activity |
|---|---|---|---|---|---|
| TrCel7A$^{Wt}$ | PPGGNRGTTTTRRPATTTGSSP GP (SEQ ID NO: 39) | 1.0 | 0.06 | — | 1.00 |
| TrCel7A$^{R\rightarrow E}$ | PPGGNEGTTTT**EE**PATTTGSSP GP (SEQ ID NO: 40) | 2.2 | 0.20 | <0.001 | 0.97 |
| TrCel7A$^{R\rightarrow E/S\rightarrow T}$ | PPGGNEGTTTT**EE**PATTTG**TT**P GP (SEQ ID NO: 41) | 2.1 | 0.13 | <0.001 | 0.95 |

REFERENCES

Altschul, S. F., Madden, T. L., Schïffer, A. A., Zhang, J., Zhang, Z., Miller, W. and Lipman, D. J. (1997) Gapped BLAST and PSI-BLAST: a new generation of protein database search programs. *Nucleic Acids Research,* 25:3389-3402.

Altschul, S. F., Gish, W., Miller, W., Myers, E. W. and Lipman, D. J. (1990) Basic local alignment search tool. *Journal of Molecular Biology,* 215:403-10.

Bae, K., Mallick, B. K and Elsik, C. G. (2008) Prediction of Protein Interdomain Linker Regions by a Nonstationary Hidden Markov Model. *Journal of the American Statistical Association,* 103 (483): 1085-99

Berlin, A., Gilkes, N., Kurabi, A., Bura, R., Tu, Maobing, Kilburn, D. and Saddler, J. (2005) Weak Lignin-Binding Enzymes. *Applied Biochemistry and Biotechnology,* Spring (121-124):163-170.

Bhikhabhai, R., et al. (1984) "Isolation of Cellulolytic Enzymes from *Trichoderma reesei* QM 9414", Journal of Applied Biochemistry, 6:336-345.

Bradford, M. M., et al. (1976) "A rapid and sensitive method for quantitation of microgram quantities of protein utilizing the principle of protein-dye binding", Analytical Biochemistry, 72:248-254.

Boisset, C., Borsali, R., Schulein, M. and Henrissat, B. (1995) Dynamic light scattering study of a two-domain structure of *Humicola insolens* endoglucanase V. *FEBS Letters,* 376(1-2):49-52.

Butler, T. and Alcalde, M. (2003) In Methods in Molecular Biology, vol. 231: (F. H. Arnold and G. Georgiou, editors), Humana Press Inc. Totowa (New Jersey), pages 17-22.

Chernoglazov, V. M., Ermolova, O. V. and Klyosov, A. A. (1988) Adsorption of high-purity endo-1,4-beta-glucanases from *Trichoderma reesei* on components of lignocellulosic materials: Cellulose, lignin, and xylan, *Enzyme and Microbial Technology,* 10(8):503-507.

Davies, G and Henrissat, B. (1995) Structures and mechanisms of glycosyl hydrolases. *Structure.* 3(9):853-9.

Escoffier, G., Toussaint, B. and Vignon, M. R. (1991) Saccharification of steam-exploded poplarwood. *Biotechnology and Bioengineering,* 38(11): 1308-1317.

Fagerstam, L. G., Pettersson, G. and Engstrom, J. A. (1984) The primary structure of a 1,4-β-glucan cellobiohydrolase from the fungus *Trichoderma reesei* QM 9414. *FEBS Letters,* 167:309-315.

Foreman, P. K., Brown, D., Dankmeyer, L., Dean, R., Diener, S., Dunn-Coleman, N. S., Goedegebuur, F., Houfek, T. D., England, G. J., Kelley, A. S., Meerman, H. J., Mitchell, T., Mitchinson, C., Olivares, H. A., Teunissen, P. J., Yao, J. and Ward, M. (2003) Transcriptional regulation of biomass-degrading enzymes in the filamentous fungus *Trichoderma reesei, Journal of Biological Chemistry,* 278(34) 31988-97.

Gietz, R. D. and Woods, R. A. (2002) Transformation of yeast by the Liac/ss carrier DNA/PEG method. *In Methods in Enzymology,* 350:87-96.

Gilkes, N. R., Henrissat, B., Kilburn, D. G., Miller, R. C. Jr. and Warren R. A. (1991) Domains in microbial beta-1,4-glycanases: sequence conservation, function, and enzyme families. *Microbiology Reviews,* 55(2):303-315.

Goto, M. (2007) Protein O-glycosylation in fungi: diverse structures and multiple functions. *Bioscience, Biotechnology and Biochemistry,* 71(6):1415-1427.

Holtzapple, M. T., Jun, J., Ashok, G., Patibanadala, S. L and Dale, B. E. (1991) The ammonia freeze explosion (AFEX) process: A practical lignocellulosic pretreatment. *Applied Biochemistry and Biotechnology,* 28/29:59-74.

Hoffman, C. S., and Winston, F. (1987) A ten-minute DNA preparation from yeast efficiently releases autonomous plasmids for transformation of *Escherichia coli. Gene,* 57: 267-272.

Kaya, F., Heitmann, J. A. and Joyce, T. W. (2000) Influence of lignin and its degradation products on enzymatic hydrolysis of xylan. *Journal of Biotechnology,* 80(3):241-247.

Kong, F., Engler, C. R. and Soltes, E. J. (1992) Effects of cell-wall acetate, xylan backbone, and lignin on enzymatic hydrolysis of aspen. *Applied Biochemistry and Biotechnology,* 34/35:23-25.

Kraulis, J., Clore, G. M., Nilges, M., Jones, T. A., Pettersson, G., Knowles, J. and Gronenborn, A. M. (1989) Determination of the three-dimensional solution structure of the C-terminal domain of cellobiohydrolase I from *Trichoderma reesei*. A study using nuclear magnetic resonance and hybrid distance geometry-dynamical simulated annealing. *Biochemistry,* 28:7241-7257.

Mattinen, M. L., Linder, M., Teleman, A. and Annila, A. (1997) Interaction between cellohexaose and cellulose binding domains from *Trichoderma reesei* cellulases. *FEBS Letters,* 407(3):291-296.

Meunier-Goddik, L. and Penner, M. H. (1999) Enzyme-catalyzed saccharification of model celluloses in the presence of lignacious residues. *Journal of Agricultural and Food Chemistry,* 47(1):346-351.

Montenecourt, B. S. and Eveleigh, D. E, (1979) Selective screening methods for the isolation of high yielding cellulase mutants of *Trichoderma reesei*. Adv. Chem. Ser. 181: 289-301.

Mooney, C. A., Mansfield, S. D., Touhy, M. G. and Saddler, J. N. (1998) The effect of initial pore volume and lignin content on the enzymatic hydrolysis of softwoods. *Bioresource Technology,* 64:113-119.

Motulsky, H., and A. Christopoulos. (2004). Fitting Models to Biological Data Using Linear and Nonlinear Regression: A Practical Guide to Curve Fitting. Oxford University Press, Inc., New York.

Needleman, S. B. and Wunsch, C. D. (1970) A general method applicable to the search for similarities in the amino acid sequence of two proteins. *Journal of Molecular Biology,* 48:443-53.

Ossowski, I. von, Eaton, J. T., Czjzek, M., Perkins, S. J., Frandsen, T. P., Schulein, M., Panine, P., Henrissat, B., Receveur-Brechot, V. (2005) Protein Disorder: Conformational distribution of a flexible linker in a chimeric double cellulase. *Biophysical Journal,* 88:2823-2832.

Palonen, H., Tjerneld, F., Zacchi, G. and Tenkanen, M. (2004) Adsorption of *Trichoderma reesei* CBH I and EG II and their catalytic domains on steam pretreated softwood and isolated lignin. *Journal of Biotechnology,* 107: 65-72.

Pearson, W. R. and Lipman, D. J. (1988) Improved tools for biological sequence comparison. *Proceedings of the National Academy of Sciences of the United States of America,* 85:2444-8.

Piyachomkwan, K., Gable, K. P. and Penner, M. H. (1997) p-Aminophenyl 1-thio-β-D-cellobioside: Synthesis and application in affinity chromatography of exo-type cellulases. *Carbohydrate Research,* 303:255-259.

Piyachomkwan, K., et al. (1998) "Aryl Thioglycoside-Based Affinity Purification of Exo-Acting Cellulases", Analytical Biochemistry, 255:223-235.

Receveur, V., Czjzek, M., Schulein, M., Panine, P. and Henrissat, B. (2002) Dimension, Shape, and Conformational Flexibility of a Two Domain Fungal Cellulase in Solution Probed by Small Angle X-Ray Scattering. *Journal of Biological Chemistry,* 277(43):40887-40892.

Reinikainen, T., Ruohonen, L., Nevanen, T., Laaksonen, L., Kraulis, P., Jones, T. A., Knowles, J. K. and Teeri, T. T. (1992) Investigation of the function of mutated cellulose-binding domains of *Trichoderma reesei* cellobiohydrolase I. *Proteins,* 14(4):475-482.

Saloheimo, M., Paloheimo, M., Hakola, S., Pere, J., Swanson, B., Nyyssonen, E., Bhatia, A., Ward, M. and Penttila, M. (2002) Swollenin, a *Trichoderma reesei* protein with sequence similarity to the plant expansins, exhibits disruption activity on cellulosic materials. *European Journal of Biochemistry,* 269:4202-11.

Shen, H., Schmuck, M., Pilz, I., Gilkes, N. R., Kilburn, D. G., Miller, R. C. Jr. and Warren, A. J. (1991) Deletion of the Linker Connecting the Catalytic and Cellulose-Binding Domains of Endoglucanase A (CenA) of *Cellulomonas fimi* Alters Its Conformation and Catalytic Activity. *Journal of Biological Chemistry,* 266(17): 11335-11340.

Smith, T. F. and Waterman, M. S. (1981) Comparison of biosequences. *Advances in Applied Mathematics,* 2:482-89.

Srisodsuk, M., Reinikainen, T., Penttila, M. and Teeri, T. T. (1993) Role of the interdomain linker peptide of *Trichoderma reesei* cellobiohydrolase I in its interaction with crystalline cellulose. *Journal of Biological Chemistry,* 268(28):20756-20761.

Suyama, M. and Ohara, O. (2003) DomCut: prediction of inter-domain linker regions in amino acid sequences. *Bioinformatics,* 19(5):673-4, (2003)

Tormo, J., Lamed, R., Chirino, A. J., Morag, E., Bayer, E. A., Shoham, Y. and Steitz, T. A. (1996) Crystal structure of a bacterial family-III cellulose-binding domain: a general mechanism for attachment to cellulose. *EMBO Journal,* 15(21):5739-5751.

Trinder, P. (1969) Determination of glucose in blood using glucose oxidase with an alternative oxygen accepter. *Annals of Clinical Biochemistry,* 6:24-27.

Tu, M., Chandra, R. P. and Saddler, J. N. (2007) Evaluating the distribution of cellulases and the recycling of free cellulases during the hydrolysis of lignocellulosic substrates. *Biotechnology Progress,* 23 (2): 398-406.

Vallejo, A. N., Pogulis, R. J. and Pease, L. R. (1994) In vitro synthesis of novel genes: mutagenesis and recombination by PCR. *PCR Methods Appl.,* 4:123-130.

Yang, B. and Wyman, C. E. (2006) BSA treatment to enhance enzymatic hydrolysis of cellulose in lignin containing substrates. *Biotechnology and Bioengineering,* 94(4):611-617.

The invention claimed is:

1. A modified cellulase enzyme comprising a cellulase catalytic domain, a modified linker peptide, and a carbohydrate binding module, wherein the amino acid sequence of the modified linker peptide is:

(a) a variant of the amino acid sequence of SEQ ID NO: 83 consisting of one or more amino acid substitutions of SEQ ID NO: 83, wherein the one or more amino acid substitutions is selected from the group consisting of G2D, S5T, S6T, S7T, S7N, S8T, S9T, S14T, S17T, S20T, S24T, S26T, S27T, S28T, G34D, S35T, T38A, and V43D of SEQ ID NO: 83, wherein the variant confers at least a 1.2-fold reduction in lignin binding to the modified cellulase enzyme relative to a cellulase enzyme comprising the same cellulase catalytic domain, a linker peptide consisting of the amino acid sequence of SEQ ID NO: 83, and the same carbohydrate binding module, or (b) a variant of the amino acid sequence of SEQ ID NO: 39 consisting of one or more amino acid substitutions of SEQ ID NO: 39, wherein the one or more amino acid substitutions is selected from the group consisting of R12E and R13E of SEQ ID NO: 39, wherein the variant confers at least a 1.2-fold reduction in lignin binding to the modified cellulase enzyme relative to a cellulase enzyme comprising the same cellulase catalytic domain, a linker peptide consisting of the amino acid sequence of SEQ ID NO: 39, and the same carbohydrate binding module, and wherein the modified linker peptide is positioned between the cellulase catalytic domain and the carbohydrate binding module and the modified cellulase enzyme exhibits cellulose-hydrolyzing activity.

2. The modified cellulase enzyme of claim 1, which exhibits at least a 1.2-fold reduction in lignin binding relative to the cellulase enzyme comprising the same cellulase catalytic domain, the linker peptide consisting of the amino acid sequence of SEQ ID NO: 83, and the same carbohydrate binding module.

3. The modified cellulase enzyme of claim 1, wherein the cellulase catalytic domain and carbohydrate binding module are derived from a fungal cellulase.

4. The modified cellulase enzyme of claim 3, wherein the fungal cellulase is derived from a fungus selected from the group consisting of *Trichoderma* ssp., *Aspergillus* ssp., *Hypocrea* ssp., *Humicola* ssp., *Neurospora* ssp., *Orpinomyces* ssp., *Gihberella* ssp., *Emericella* ssp., *Chaetomium* ssp., *Chrysosporium* ssp., *Myceliophthora* ssp., *Fusarium* ssp., *Penicillium* ssp., *Magnaporthe* ssp., *Phanerochaete* ssp., *Trametes* ssp., *Lentinula edodes, Gleophyllum trabeiu, Ophiostoma piliferum, Corprinus cinereus, Geomyces pannorum, Cryptococcus laurentii, Aureobasidium pullulans, Amorphotheca resinae, Leucosporidium scotti, Cunninghamella elegans, Thermomyces lanuginose*, and *Sporotrichum thermophile.*

5. The modified cellulase enzyme of claim 1, wherein the cellulase catalytic domain comprises an amino acid sequence that is at least 90% identical to an amino acid sequence selected from the group consisting of: amino acids 1 to 375 of SEQ ID NO: 4, amino acids 71 to 397 of SEQ ID NO: 2, amino acids 1 to 165 of SEQ ID NO: 5, amino acids 1 to 235 of SEQ ID NO: 6, amino acids 1-437 of SEQ ID NO: 3, and amino acids 83-447of SEQ ID NO: 1, and wherein the carbohydrate binding module comprises an amino acid sequence that is at least 90% identical to the amino acid sequence of SEQ ID NO: 49 or SEQ ID NO: 50.

6. The modified cellulase enzyme of claim 5, wherein the cellulase catalytic domain comprises an amino acid sequence that is at least 90% identical to amino acids 1-437 of SEQ ID NO: 3 or amino acids 83-447 of SEQ ID NO: 1.

7. The modified cellulase enzyme of claim 5, wherein the amino acid sequence that is at least 90% identical to amino acids 83-447 of SEQ ID NO: 1 comprises one or more amino acid substitutions of the amino acid sequence of amino acids 83-447 of SEQ ID NO: 1 selected from the group consisting of: Y103H, Y103K, Y103R, Y103A, Y103V, Y103L, Y103P, M134I, M134Q, M134T, M134V, M134Y, L136V, L136I, S186K, S186T, S186Y, Q204K, G213D, A322D, Q363E, G365D, G365E, G365Q, G365S, R410A, R410F, R410L, R410Q, R410S and S413P.

8. The modified cellulase enzyme of claim 1, wherein the cellulase catalytic domain comprises an amino acid sequence selected from the group consisting of: amino acids 1 to 375 of SEQ ID NO: 4, amino acids 71 to 397 of SEQ ID NO: 2, amino acids 1 to 165 of SEQ ID NO: 5, amino acids 1 to 235 of SEQ ID NO: 6, amino acids 1-437 of SEQ ID NO: 3, and amino acids 83-447 of SEQ ID NO: 1.

9. The modified cellulase enzyme of claim 1, further comprising at least one additional functional domain selected from the group consisting of a glycosyl hydrolase domain, a carbohydrate binding module, a cohesin domain, a dockerin domain and a fibronectin like domain.

10. A process for hydrolyzing a cellulose substrate comprising contacting the substrate with the modified cellulase enzyme of claim 1 in the presence of lignin to thereby hydrolyze the substrate.

11. A process for the production of fermentable sugars comprising contacting a pretreated lignocellulosic substrate with the modified cellulase enzyme of claim 1 to hydrolyze the substrate and thereby produce fermentable sugars.

* * * * *